United States Patent
Aldous et al.

(10) Patent No.: US 8,202,863 B2
(45) Date of Patent: Jun. 19, 2012

(54) PYRIMIDINE AMIDE COMPOUNDS AS PGDS INHIBITORS

(75) Inventors: Suzanne C. Aldous, Gillette, NJ (US); John Ziqi Jiang, Hillsborough, NJ (US); Jinqi Lu, Somerville, NJ (US); Liang Ma, Hillsborough, NJ (US); Lan Mu, Bedminster, NJ (US); Harry Randall Munson, Annandale, NJ (US); Jeffrey Stephen Sabol, Bridgewater, NJ (US); Sukanthini Thurairatnam, Bedminster, NJ (US); Christopher Loren Vandeusen, East Windsor, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 181 days.

(21) Appl. No.: 12/062,641

(22) Filed: Apr. 4, 2008

(65) Prior Publication Data

US 2008/0227782 A1 Sep. 18, 2008

Related U.S. Application Data

(63) Continuation of application No. PCT/US2006/038841, filed on Oct. 4, 2006.

(60) Provisional application No. 60/723,570, filed on Oct. 4, 2005.

(51) Int. Cl.
*C07D 239/28* (2006.01)
*C07D 403/12* (2006.01)
*A61K 31/506* (2006.01)

(52) U.S. Cl. ............ 514/235.8; 514/252.14; 514/256; 544/122; 544/295; 544/296; 544/333; 544/335

(58) Field of Classification Search ............ 544/122, 544/295, 296, 333, 335; 514/235.8, 252.14, 514/256
See application file for complete search history.

(56) References Cited

U.S. PATENT DOCUMENTS

2005/0165028 A1* 7/2005 Norman et al. ............ 514/256

FOREIGN PATENT DOCUMENTS

| EP | 1471057 | 10/2004 |
|---|---|---|
| EP | 1553089 | 7/2005 |
| JP | 03/112985 | 5/1991 |
| JP | 2000/226372 | 8/2000 |
| WO | WO 95/25723 | 9/1995 |
| WO | WO 01/70671 | 9/2001 |
| WO | WO 2004/011430 | 2/2004 |
| WO | WO 2004/072069 | 8/2004 |
| WO | WO 2005/032493 | 4/2005 |
| WO | WO 2007/041634 A1 | 4/2007 |

OTHER PUBLICATIONS

Kato et al., CAPLUS Abstract 134:266103 (2001).*
Morimoto, CAPLUS Abstract 58:20724 (1963).*
Ulrich, Chapter 4: Crystallization, Kirk-Othmer Encyclopedia of Chemical Technology, Aug. 2002.*
Vippagunta et al., Crystalline Solids, Advanced Drug Delivery Reviews, 48, pp. 3-26, 2001.*
West, Solid Solutions, Solid State Chemistry and its applications, pp. 358 & 365, 1988.*
Palanki, et al., Inhibitors of NF-κB and AP-1 Gene Expression: SAR studies on the pyrimidine portion of 2-Chloro-4-Trifluoromethylpyrimidine-5-[N-(3',5'-bis(Trifluoromethyl)-Phenyl)Carboxamide], J. of Med. Chem; ,vol. 43, (2000); pp. 3995-4004.

* cited by examiner

*Primary Examiner* — Deepak Rao
(74) *Attorney, Agent, or Firm* — Ronald G. Ort; Barbara E. Kurys

(57) ABSTRACT

This invention is directed to a compound of formula (I):

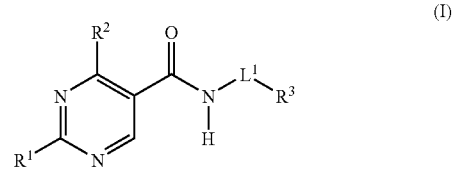

wherein $R^1$, $R^2$, $R^3$ and $L^1$ are as defined herein, a pharmaceutical composition comprising the compound, and the use of the compound to treat allergic and/or inflammatory disorders, particularly disorders such as allergic rhinitis, asthma and/or chronic obstructive pulmonary disease (COPD).

28 Claims, No Drawings

PYRIMIDINE AMIDE COMPOUNDS AS PGDS INHIBITORS

This application is a Continuation of International Application No. PCT/US2006/038841, filed Oct. 4, 2006, which claims the benefit of Provisional Application No. 60/723,570, filed Oct. 4, 2005.

FIELD OF THE INVENTION

The present invention is directed to pyrimidine amide compounds, their preparation, pharmaceutical compositions containing these compounds, and their pharmaceutical use in the treatment of disease states capable of being modulated by the inhibition of the prostaglandin D synthase.

BACKGROUND OF THE INVENTION

Allergic rhinitis, the most common atopic disease, has an estimated prevalence ranging from about 5 to about 22 percent of the general human population and is characterized by the symptoms of sneezing, nasal discharge, and nasal congestion. These symptoms are believed to be triggered by multiple mediators released from mast cells and other inflammatory cells. Current therapies, such as antihistamines, deal effectively with the sneezing and nasal discharge, but have little effect on congestion, which is a key symptom affecting the quality of life of patients.

Local allergen challenge in patients with allergic rhinitis, bronchial asthma, allergic conjunctivitis and atopic dermatitis has been shown to result in rapid elevation of prostaglandin D2 "(PGD2)" levels in nasal and bronchial lavage fluids, tears and skin chamber fluids. PGD2 has many inflammatory actions, such as increasing vascular permeability in the conjunctiva and skin, increasing nasal airway resistance, airway narrowing and eosinophil infiltration into the conjunctiva and trachea. PGD2 is the major cyclooxygenase product of arachidonic acid produced from mast cells on immunological challenge [Lewis, R A, Soter N A, Diamond P T, Austen K F, Oates J A, Roberts L J II, Prostaglandin D2 generation after activation of rat and human mast cells with anti-IgE, *J. Immunol.* 129, 1627-1631, 1982]. Activated mast cells, a major source of PGD2, are one of the key players in driving the allergic response in conditions such as asthma, allergic rhinitis, allergic conjunctivitis, allergic dermatitis and other diseases [Brightling C E, Bradding P, Pavord I D, Wardlaw A J, New Insights into the role of the mast cell in asthma, *Clin. Exp. Allergy* 33, 550-556, 2003].

In the presence of sulfhydryl compounds, PGD2 is formed by the isomerization of PGH2, a common precursor of prostanoids, by catalytic action of prostaglandin D synthase "(PGDS)". There are two isoforms of the PGDS enzyme: L-PGDS; and H-PGDS. H-PGDS is a cytosolic enzyme, which is distributed in the peripheral tissues, and which is localized in the antigen-presenting cells, mast cells, megakaryocytes, and Th2 lymphocytes. The action of the product PGD2 is mediated by G-protein coupled receptors: D prostaglandin "(DP)" and crTH2. See (1) Prostaglandin D Synthase: Structure and Function. T. Urade and O. Hayaishi, *Vitamin and Hormones*, 2000, 58, 89-120, (2) J. J. Murray, *N. Eng. J. Med.*, 1986 September. 25; 315(13):800, and (3) Urade et. al, *J. Immunology* 168: 443-449, 2002.

We believe that inhibiting the formation of PGD2 should have an effect on nasal congestion and, therefore, be of therapeutic benefit in allergic rhinitis. In addition, we believe that a PGDS inhibitor should be of therapeutic benefit in a number of other indications such as bronchial asthma.

PGDS inhibitors have been reported. The compound, HQL-79, is reported to be a weak PGDS inhibitor, and is antiasthmatic in guinea pig and rat models (Matsusshita, et al., Jpn. J. Pharamcol. 78: 11, 1998). The compound Tranilast is described as a PGDS inhibitor. (Inhibitory Effect of Tranilast on Prostaglandin D Synthesase. K. Ikai, M. Jihara, K. Fujii, and Y. Urade. *Biochemical Pharmacology,* 1989, 28, 2773-2676).

SUMMARY OF THE INVENTION

The present invention is directed to a compound of formula (I):

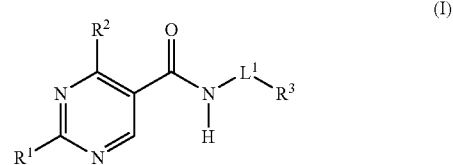

wherein:
$R^1$ is aryl, heteroaryl or $(C_5-C_6)$-cycloalkyl, each of which is optionally substituted by halo, $(C_1-C_6)$-alkyl, hydroxy, $(C_1-C_6)$-alkoxy, $(C_1-C_4)$-haloalkyl or $(C_1-C_4)$-haloalkoxy;
$R^2$ is hydrogen or $(C_1-C_4)$-alkyl;
$R^3$ is —P(=O)-(alkoxy)$_2$, or $Y^1Y^2N$—SO$_2$—, cycloalkyl, cycloalkenyl, aryl, heteroaryl, heterocyclyl, heterocyclenyl, or multicyclic alkaryl, each of which is optionally substituted by:
acyl, cyano, nitro, halo, hydroxy, carboxy, amidino, $R^5O$—C(=O)—C(=N—OR$^4$)—, $Y^1Y^2N$—, $Y^1Y^2N$—C(=O)—, $Y^1Y^2N$—C(=O)—O—, $Y^1Y^2N$—SO$_2$—, $R^7$—SO$_2$—NR$^6$—, $R^7$—C(=O)—NR$^6$—, $Y^1Y^2N$—(C$_1$-C$_4$)-alkylene-SO$_2$—(C$_1$-C$_4$)-alkylene-, or
alkyl, alkenyl, alkynyl, alkoxy, alkoxycarbonyl, alkylthio, alkylsulfinyl, or alkylsulfonyl, each of which is optionally substituted by:
halo, alkoxy, haloalkoxy, hydroxy, carboxy, alkoxycarbonyl, —P(=O)-(alkoxy)$_2$, $Y^1Y^2N$—, $Y^1Y^2N$—SO$_2$—, $R^7$—SO$_2$—NR$^6$—,
aryl or heteroaryl, each of which is optionally substituted by alkyl, halo, haloalkyl, alkoxy, haloalkoxy, hydroxy, amino, alkylamino, dialkylamino, carboxy, or alkoxycarbonyl, or heterocyclyl or arylheterocyclyl, each of which is optionally substituted by oxo or alkyl, or
aryl, heteroaryl, aroyl, heteroaroyl, aryloxy, heteroaryloxy, or heterocyclyl, each of which is optionally substituted by alkyl, haloalkyl, halo, alkoxy, haloalkoxy, hydroxy, carboxy, alkoxycarbonyl, —P(=O)-(alkoxy)$_2$, $Y^1Y^2N$—, or $Y^1Y^2N$—SO$_2$—, and
when $R^3$ is cycloalkyl, cycloalkenyl, heterocyclyl, heterocyclenyl or multicyclic alkaryl, it is also optionally substituted by oxo;
$L^1$ is a bond, or $(C_1-C_6)$-alkylene optionally substituted by hydroxy or when $R^3$ is optionally substituted cycloalkyl, cycloalkenyl, aryl, heteroaryl, heterocyclyl, heterocyclenyl or multicyclic alkaryl, then the $(C_1-C_6)$-alkylene is also optionally substituted by —P(=O)-(alkoxy)$_2$;
$R^4$, $R^5$ and $R^6$ are each independently hydrogen or alkyl,
$R^7$ is alkyl optionally substituted by hydroxy, halo or alkoxy, or
aryl, heteroaryl, arylalkyl or heteroarylalkyl, wherein the aryl, heteroaryl or the aryl or heteroaryl moiety of the arylalkyl or heteroarylalkyl is optionally substituted by alkyl, haloalkyl, hydroxy, carboxy, alkoxycarbonyl, amino, alkylamino, dialkylamino, halo, alkoxy or haloalkoxy; and $Y^1$ and $Y^2$ are each independently:

hydrogen, alkyl optionally substituted by:
hydroxy, carboxy, halo, amino, alkylamino, dialkylamino, cycloalkylamino, aminocarbonyl, alkylaminocarbonyl, dialkylaminocarbonyl, cycloalkylaminocarbonyl,
alkoxy optionally substituted with hydroxy, cycloalkyl, heterocyclyl, aryl or heteroaryl, each of which is optionally substituted by alkyl, halo or haloalkyl, or
cycloalkyl optionally substituted by carboxy, or $Y^1$ and $Y^2$ together with the nitrogen atom to which they are attached form a heterocyclyl optionally containing another heteroatom selected from oxygen, nitrogen or sulfur, wherein the heterocyclyl is optionally substituted with alkyl or oxo;
or a hydrate, solvate or N-oxide thereof, or a pharmaceutically acceptable salt thereof Another aspect of the present invention is a pharmaceutical composition comprising a pharmaceutically effective amount of a compound according to formula (I), or a hydrate, solvate or N-oxide thereof, or a pharmaceutically acceptable salt thereof, in admixture with a pharmaceutically acceptable carrier.

Another aspect of the present invention is directed to a method of treating allergic and/or inflammatory disorders, particularly disorders such as allergic rhinitis, asthma and/or chronic obstructive pulmonary disease (COPD) in a patient in need thereof by administering to the patient a compound according to formula (I), or a hydrate, solvate or N-oxide thereof, or a pharmaceutically acceptable salt thereof.

DETAILED DESCRIPTION OF THE INVENTION

Definition of Terms

As used above, and throughout the description of the invention, the following terms unless otherwise indicated, shall be understood to have the following meanings: "Acyl" means H—CO— or (aliphatic or cyclyl)-CO—. Particular acyl includes lower alkanoyl that contains a lower alkyl. Exemplary acyl includes formyl, acetyl, propanoyl, 2-methylpropanoyl, butanoyl, palmitoyl, acryloyl, propanoyl, and cyclohexylcarbonyl.

"Alkenyl" means a straight or branched aliphatic hydrocarbon group containing a carbon-carbon double bond and having 2 to about 15 carbon atoms. Particular alkenyl has 2 to about 12 carbon atoms. More particular alkenyl has 2 to about 4 carbon atoms. Branched means that one or more lower alkyl groups such as methyl, ethyl or propyl are attached to a linear alkenyl chain. "Lower alkenyl" means about 2 to about 4 carbon atoms in the chain that may be straight or branched. Exemplary alkenyl includes ethenyl, propenyl, n-butenyl, i-butenyl, 3-methylbut-2-enyl, n-pentenyl, heptenyl, octenyl, cyclohexylbutenyl, and decenyl.

"Alkoxy" means alkyl-O—. Exemplary alkoxy includes methoxy, ethoxy, n-propoxy, i-propoxy, n-butoxy, and heptoxy.

"Alkoxycarbonyl" means alkyl-O—CO—. Exemplary alkoxycarbonyl includes methoxycarbonyl, ethoxycarbonyl, and t-butyloxycarbonyl.

"Alkyl" means straight or branched aliphatic hydrocarbon having 1 to about 20 carbon atoms. Particular alkyl has 1 to about 12 carbon atoms. More particular alkyl is lower alkyl. Branched means that one or more lower alkyl groups such as methyl, ethyl or propyl are attached to a linear alkyl chain. "Lower alkyl" means 1 to about 4 carbon atoms in a linear alkyl chain that may be straight or branched.

"Alkylamino" means alkyl-NH—. Particular alkylamino is $(C_1-C_6)$-alkylamino. Exemplary alkylamino includes methylamino and ethylamino.

"Alkylene" means a straight or branched bivalent hydrocarbon having from 1 to about 15 carbon atoms. Particular alkylene is the lower alkylene having from 1 to about 6 carbon atoms. Exemplary alkenylene includes methylene, ethylene, propylene, and butylenes.

"Alkylsulfonyl" means alkyl-$SO_2$—. Particular alkylsulfonyl is $(C_1-C_6)$-alkylsulfonyl. Exemplary alkylsulfonyl includes $CH_3$—$SO_2$—, and $CH_3CH_2$—$SO_2$—.

"Alkylthio" means an alkyl-S—. Exemplary alkylthio includes $CH_3$—S—.

"Alkynyl" means straight or branched aliphatic hydrocarbon containing a carbon-carbon triple bond and having 2 to about 15 carbon atoms. Particular alkynyl has 2 to about 12 carbon atoms. More particular alkynyl has 2 to about 6 carbon atoms. Branched means that one or more lower alkyl such as methyl, ethyl or propyl are attached to a linear alkynyl chain.

"Lower alkynyl" means 2 to about 4 carbon atoms in a linear alkynyl chain that may be straight or branched. Exemplary alkynyl includes ethynyl, propynyl, n-butynyl, 2-butynyl, 3-methylbutynyl, n-pentynyl, heptynyl, octynyl, and decynyl.

"Aroyl" means aryl-CO—. Exemplary aroyl includes benzoyl, and 1- and 2-naphthoyl.

"Aryl" means an aromatic monocyclic or multicyclic ring system of about 6 to about 14 carbon atoms. Particular aryl include about 6 to about 10 carbon atoms. Exemplary aryl include phenyl and naphthyl.

"Arylalkoxy" means arylalkyl-O—. Exemplary arylalkoxy includes benzyloxy and 1- or 2-naphthylenemethoxy.

"Arylalkoxycarbonyl" means arylalkyl-O—CO—. Exemplary arylalkoxycarbonyl includes phenoxycarbonyl and naphthoxycarbonyl.

"Arylalkyl" means aryl-alkyl-. Particular arylalkyl contains a $(C_1-C_6)$-alkyl moiety. Exemplary arylalkyl includes benzyl, 2-phenethyl and naphthylenemethyl.

"Arylalkylsulfonyl" means aryl-alkyl-$SO_2$—. Particular arylalkylsulfonyl contains a $(C_1-C_6)$-alkyl moiety. Exemplary arylalkylsulfonyl includes benzylsulfonyl.

"Arylcycloalkenyl" means a fused aryl and cycloalkenyl. Particular arylcycloalkenyl is one wherein the aryl thereof is phenyl and the cycloalkenyl consists of about 5 to about 7 ring atoms. An arylcycloalkenyl is bonded through any atom of the cycloalkenyl moiety thereof capable of such bonding. Exemplary arylcycloalkenyl includes 1,2-dihydronaphthalene and indene.

"Arylcycloalkyl" means a fused aryl and cycloalkyl. Particular arylcycloalkyl is one wherein the aryl thereof is phenyl and the cycloalkyl consists of about 5 to about 6 ring atoms. An arylcycloalkyl is bonded through any atom of the cycloalkyl moiety thereof capable of such bonding. Exemplary arylcycloalkyl includes 1,2,3,4-tetrahydro-naphthylene.

"Arylheterocyclenyl" means a fused aryl and heterocyclenyl. Particular arylheterocyclenyl is one wherein the aryl thereof is phenyl and the heterocyclenyl consists of about 5 to about 6 ring atoms. An arylheterocyclenyl is bonded through any atom of the heterocyclenyl thereof capable of such bonding. The designation of the aza, oxa or thio as a prefix before the heterocyclenyl portion of the arylheterocyclenyl defines that at least a nitrogen, oxygen or sulfur atom is present, respectively, as a ring atom. The nitrogen atom of an arylheterocyclenyl may be a basic nitrogen atom. The nitrogen or sulfur atom of the heterocyclenyl portion of the arylheterocyclenyl may also be optionally oxidized to the corresponding N-oxide, S-oxide or S,S-dioxide. Exemplary arylheterocyclenyl includes 3H-indolinyl, 1H-2-oxoquinolyl, 2H-1-oxoisoquinolyl, 1,2-di-hydroquinolinyl, 3,4-dihydroquinolinyl, 1,2-dihydroisoquinolinyl, and 3,4-dihydroisoquinolinyl.

"Arylheterocyclyl" means a fused aryl and heterocyclyl. Particular heterocyclylacyl is one wherein the aryl thereof is phenyl and the heterocyclyl consists of about 5 to about 6 ring atoms. An arylheterocyclyl is bonded through any atom of the heterocyclyl moiety thereof capable of such bonding. The designation of the aza, oxa or thio as a prefix before heterocyclyl portion of the arylheterocyclyl defines that at least a nitrogen, oxygen or sulfur atom is present, respectively, as a ring atom. The nitrogen atom of an arylheterocyclyl may be a basic nitrogen atom. The nitrogen or sulfur atom of the heterocyclyl portion of the arylheterocyclyl may also be optionally oxidized to the corresponding N-oxide, S-oxide or S,S-dioxide. Exemplary arylheterocyclyl includes indolinyl, 1,2,3,4-tetrahydroisoquinoline, 1,2,3,4-tetrahydroquinoline, 1H-2,3-dihydroisoindol-2-yl, 2,3-dihydrobenz[f]isoindol-2-yl, and 1,2,3,4-tetrahydrobenz[g]-isoquinolin-2-yl.

"Aryloxy" means an aryl-O—. Exemplary aryloxy includes phenoxy and naphthoxy.

"Aryloxycarbonyl" means aryl-O—CO—. Exemplary aryloxycarbonyl includes phenoxycarbonyl and naphthoxycarbonyl.

"Compounds of the present invention", and equivalent expressions, are meant to embrace compounds of Formula (I) as hereinbefore described, the hydrates, solvates and N-oxides thereof, and the pharmaceutically acceptable salts thereof, where the context so permits. Similarly, reference to intermediates, whether or not they themselves are claimed, is meant to embrace their salts, N-oxides and solvates, where the context so permits.

"Cycloalkenyl" means a non-aromatic mono- or multicyclic ring system of about 3 to about 10 carbon atoms, particularly of about 5 to about 10 carbon atoms, and which contains at least one carbon-carbon double bond. Particular rings of the ring system include about 5 to about 6 ring atoms; and such particular ring sizes are also referred to as "lower". Exemplary monocyclic cycloalkenyl includes cyclopentenyl, cyclohexenyl, and cycloheptenyl. An exemplary multicyclic cycloalkenyl is norbornylenyl.

"Cycloalkenylaryl" means a fused aryl and cycloalkenyl. Particular cycloalkenylaryl is one wherein the aryl thereof is phenyl and the cycloalkenyl consists of about 5 to about 6 ring atoms. A cycloalkenylaryl is bonded through any atom of the aryl moiety thereof capable of such bonding. Exemplary cycloalkenylaryl includes 1,2-dihydronaphthalene and indene.

"Cycloalkenylheteroaryl" means a fused heteroaryl and cycloalkenyl. Particular cycloalkenylheteroaryl is one wherein the heteroaryl thereof consists of about 5 to about 6 ring atoms and the cycloalkenyl consists of about 5 to about 6 ring atoms. A cycloalkenylheteroaryl is bonded through any atom of the heteroaryl thereof capable of such bonding. The designation of the aza, oxa or thio as a prefix before heteroaryl portion of the cycloalkenylheteroaryl defines that at least a nitrogen, oxygen or sulfur atom is present, respectively, as a ring atom. The nitrogen atom of a cycloalkenylheteroaryl may be a basic nitrogen atom. The nitrogen atom of the heteroaryl portion of the cycloalkenylheteroaryl may also be optionally oxidized to the corresponding N-oxide. Exemplary cycloalkenylheteroaryl includes 5,6-dihydroquinolyl, 5,6-dihydroisoquinolyl, 5,6-dihydroquinoxalinyl, 5,6-dihydroquinazolinyl, 4,5-dihydro-1H-benzimidazolyl, and 4,5-dihydrobenzoxazolyl.

"Cycloalkyl" means a non-aromatic mono- or multicyclic saturated ring system of about 3 to about 10 carbon atoms, particularly of about 5 to about 10 carbon atoms. Particular ring systems include about 5 to about 7 ring atoms; and such particular ring systems are also referred to as "lower". Exemplary monocyclic cycloalkyl includes cyclopentyl, cyclohexyl, and cycloheptyl. Exemplary multicyclic cycloalkyl includes 1-decalin, norbornyl, and adamant-(1- or 2-)yl.

"Cycloalkylaryl" means a fused aryl and cycloalkyl. Particular cycloalkylaryl is one wherein the aryl thereof is phenyl and the cycloalkyl consists of about 5 to about 6 ring atoms. A cycloalkylaryl is bonded through any atom of the cycloalkyl moiety thereof capable of such bonding. Exemplary cycloalkylaryl includes 1,2,3,4-tetrahydro-naphthylene.

"Cycloalkylene" means a bivalent cycloalkyl group having about 4 to about 8 carbon atoms. Particular cycloalkylene includes about 5 to about 7 ring atoms; and such particular ring systems are also referred to as "lower". The points of binding on the cycloalkylene group include 1,1-, 1,2-, 1,3-, or 1,4-binding patterns, and where applicable the stereochemical relationship of the points of binding is either cis or trans. Exemplary monocyclic cycloalkylene includes (1,1-, 1,2-, or 1,3-)cyclohexylene and (1,1- or 1,2-)cyclopentylene.

"Cycloalkylheteroaryl" means a fused heteroaryl and cycloalkyl. Particular cycloalkylheteroaryl is one wherein the heteroaryl thereof consists of about 5 to about 6 ring atoms and the cycloalkyl consists of about 5 to about 6 ring atoms. A cycloalkylheteroaryl is bonded through any atom of the heteroaryl thereof capable of such bonding. The designation of the aza, oxa or thio as a prefix before heteroaryl portion of the fused cycloalkylheteroaryl defines that at least a nitrogen, oxygen or sulfur atom is present, respectively, as a ring atom. The nitrogen atom of a cycloalkylheteroaryl may be a basic nitrogen atom. The nitrogen atom of the heteroaryl portion of the cycloalkylheteroaryl may also be optionally oxidized to the corresponding N-oxide. Exemplary cycloalkylheteroaryl includes 5,6,7,8-tetrahydroquinolinyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, and 4,5,6,7-tetrahydrobenzoxazolyl.

"Cyclyl" means cycloalkyl, cycloalkenyl, heterocyclyl or heterocyclenyl.

"Dialkylamino" means (alkyl)$_2$-N—. Particular dialkylamino is (C$_1$-C$_6$alkyl)$_2$-N—. Exemplary dialkylamino groups include dimethylamino, diethylamino and methylethylamino.

"Halo" or "halogen" means fluoro, chloro, bromo, or iodo. Particular halo or halogen is fluoro or chloro.

"Haloalkoxy" means alkoxy substituted by one to three halo groups. Particular haloalkoxy are loweralkoxy substituted by one to three halogens. Most particular haloalkoxy are loweralkoxy substituted by one halogen.

"Haloalkyl" means alkyl substituted by one to three halo groups. Particular haloalkyl are loweralkyl substituted by one to three halogens. Most particular haloalkyl are loweralkyl substituted by one halogen.

"Heteroaroyl" means heteroaryl-CO—. Exemplary heteroaroyl includes thiophenyl, nicotinoyl, pyrrol-2-ylcarbonyl, and pyridinoyl.

"Heteroaryl" means an aromatic monocyclic or multicyclic ring system of about 5 to about 14 carbon atoms, in which one or more of the carbon atoms in the ring system is/are hetero element(s) other than carbon, for example nitrogen, oxygen or sulfur. Particular aromatic ring systems include about 5 to about 10 carbon atoms, and include 1 to 3 heteroatoms. More particular ring sizes of rings of the ring system include about 5 to about 6 ring atoms. The designation of the aza, oxa or thio as a prefix before heteroaryl defines that at least a nitrogen, oxygen or sulfur atom is present, respectively, as a ring atom. A nitrogen atom of a heteroaryl may be a basic nitrogen atom and may also be optionally oxidized to the corresponding N-oxide. When a heteroaryl is substituted by a hydroxy group, it also includes its corresponding tautomer. Exemplary heteroaryl includes pyrazinyl, thienyl, isothiazolyl, oxazolyl, pyrazolyl, furanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofuranyl, azaindolyl, benzimidazolyl, benzothienyl, thienopyridyl, thienopyrimidyl, pyrrolopyridyl, imidazopyridyl, benzoazaindolyl, 1,2,4-triazinyl, benzothiazolyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl, and triazolyl.

"Heteroarylalkyl" means heteroaryl-alkyl-. Particular heteroarylalkyl contains a $(C_1-C_4)$-alkyl moiety. Exemplary heteroarylalkyl includes tetrazol-5-ylmethyl.

"Heteroarylcycloalkenyl" means a fused heteroaryl and cycloalkenyl. Particular heteroarylcycloalkenyl is one wherein the heteroaryl thereof consists of about 5 to about 6 ring atoms and the cycloalkenyl consists of about 5 to about 6 ring atoms. A heteroarylcycloalkenyl is bonded through any atom of the cycloalkenyl thereof capable of such bonding. The designation of the aza, oxa or thio as a prefix before heteroaryl portion of the heteroarylcycloalkenyl defines that at least a nitrogen, oxygen or sulfur atom is present, respectively, as a ring atom. The nitrogen atom of a heteroarylcycloalkenyl may be a basic nitrogen atom. The nitrogen atom of the heteroaryl portion of the heteroarylcycloalkenyl may also be optionally oxidized to the corresponding N-oxide. Exemplary heteroarylcycloalkenyl includes 5,6-dihydroquinolyl, 5,6-dihydroisoquinolyl, 5,6-dihydroquinoxalinyl, 5,6-dihydroquinazolinyl, 4,5-dihydro-1H-benzimidazolyl, and 4,5-di-hydrobenzoxazolyl.

"Heteroarylcycloalkyl" means a fused heteroaryl and cycloalkyl. Particular heteroarylcycloalkyl is one wherein the heteroaryl thereof consists of about 5 to about 6 ring atoms and the cycloalkyl consists of about 5 to about 6 ring atoms. A heteroarylcycloalkyl is bonded through any atom of the cycloalkyl thereof capable of such bonding. The designation of the aza, oxa or thio as a prefix before heteroaryl portion of the fused heteroarylcycloalkyl defines that at least a nitrogen, oxygen or sulfur atom is present, respectively, as a ring atom. The nitrogen atom of a heteroarylcycloalkyl may be a basic nitrogen atom. The nitrogen atom of the heteroaryl portion of the heteroarylcycloalkyl may also be optionally oxidized to the corresponding N-oxide. Exemplary heteroarylcycloalkyl includes 5,6,7,8-tetrahydroquinolinyl, 5,6,7,8-tetra-hydroisoquinolyl, 5,6,7,8-tetrahydroquinoxalinyl, 5,6,7,8-tetrahydroquinazolyl, 4,5,6,7-tetrahydro-1H-benzimidazolyl, and 4,5,6,7-tetrahydrobenzoxazolyl "Heteroarylheterocyclenyl" means a fused heteroaryl and heterocyclenyl. Particular heteroarylheterocyclenyl is one wherein the heteroaryl thereof consists of about 5 to about 6 ring atoms and the heterocyclenyl consists of about 5 to about 6 ring atoms. A heteroarylheterocyclenyl is bonded through any atom of the heterocyclenyl thereof capable of such bonding. The designation of the aza, oxa or thio as a prefix before the heteroaryl or heterocyclenyl portion of the heteroarylheterocyclenyl defines that at least a nitrogen, oxygen or sulfur atom is present, respectively, as a ring atom. The nitrogen atom of a heteroarylazaheterocyclenyl may be a basic nitrogen atom. The nitrogen or sulfur atom of the heteroaryl or heterocyclyl portion of the heteroarylheterocyclyl may also be optionally oxidized to the corresponding N-oxide, S—oxide or S,S-dioxide. Exemplary heteroarylheterocyclenyl includes 7,8-dihydro[1,7]naphthyridinyl, 1,2-dihydro[2,7]-naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyridinyl, and 1,2-dihydro-2,6-naphthyridinyl.

"Heteroarylheterocyclyl" means a fused heteroaryl and heterocyclyl. Particular heteroarylheterocyclyl is one wherein the heteroaryl thereof consists of about 5 to about 6 ring atoms and the heterocyclyl consists of about 5 to about 6 ring atoms. A heteroarylheterocyclyl is bonded through any atom of the heterocyclyl thereof capable of such bonding. The designation of the aza, oxa or thio as a prefix before the heteroaryl or heterocyclyl portion of the fused heteroarylheterocyclyl defines that at least a nitrogen, oxygen or sulfur atom is present, respectively, as a ring atom. The nitrogen atom of a fused heteroarylheterocyclyl may be a basic nitrogen atom. The nitrogen or sulfur atom of the heteroaryl or heterocyclyl portion of the heteroarylheterocyclyl may also be optionally oxidized to the corresponding N-oxide, S-oxide or S,S-dioxide. Exemplary heteroarylheterocyclyl includes 2,3-dihydro-1H-pyrrol[3,4-b]quinolin-2-yl, 1,2,3,4-tetrahydrobenz[b][1,7]naphthyridin-2-yl, 1,2,3,4-tetrahydrobenz[b][1,6]naphthyridin-2-yl, 1,2,3,4-tetra-hydro-9H-pyrido[3,4-b]indol-2-yl, 1,2,3,4-tetrahydro-9H-pyrido[4,3-b]indol-2-yl, 2,3-dihydro-1H-pyrrolo[3,4-b]indol-2-yl, 1H-2,3,4,5-tetrahydroazepino[3,4-b]indol-2-yl, 1H-2,3,4,5-tetra-hydroazepino[4,3-b]indol-3-yl, 1H-2,3,4,5-tetrahydroazepino[4,5-b]indol-2yl, 5,6,7,8-tetra-hydro[1,7]naphthyridyl, 1,2,3,4-tetrhydro[2,7]naphthyridyl, 2,3-dihydro[1,4]dioxino[2,3-b]pyridyl, 2,3-dihydro-[1,4]dioxino[2,3-b]pyridyl, 3,4-dihydro-2H-1-oxa[4,6]diazanaphthalenyl, 4,5,6,7-tetrahydro-3H-imidazo[4,5-c]pyridyl, 6,7-dihydro[5,8]diazanaphthalenyl, 1,2,3,4-tetrahydro[1,5]-naphthyridinyl, 1,2,3,4-tetrahydro[1,6]naphthyridinyl, 1,2,3,4-tetrahydro[1,7]naphthyridinyl, 1,2,3,4-tetrahydro[1,8]naphthyridinyl, and 1,2,3,4-tetra-hydro[2,6]naphthyridinyl.

"Heteroaryloxy" means heteroaryl-O—. Exemplary heteroaryloxy includes pyridyloxy.

"Heterocyclenyl" means a non-aromatic monocyclic or multicyclic hydrocarbon ring system of about 3 to about 10 carbon atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. A particular non-aromatic ring system includes about 5 to about 10 carbon atoms, and 1 to 3 heteroatoms. More particular ring sizes of rings of the ring system include about 5 to about 6 ring atoms; and such particular ring sizes are also referred to as "lower". The designation of the aza, oxa or thio as a prefix before heterocyclenyl defines that at least a nitrogen, oxygen or sulfur atom is present, respectively, as a ring atom. The nitrogen atom of a heterocyclenyl may be a basic nitrogen atom. The nitrogen or sulfur atom of the heterocyclenyl may also be optionally oxidized to the corresponding N-oxide, S-oxide or S,S-dioxide. Exemplary monocyclic azaheterocyclenyl includes 1,2,3,4-tetrahydrohydropyridyl, 1,2-dihydropyridyl, 1,4-dihydropyridyl, 1,2,3,6-tetra-hydropyridyl, 1,4,5,6-tetrahydropyrimidine, 2-pyrrolinyl, 3-pyrrolinyl, 2-imidazolinyl, and 2-pyrazolinyl. Exemplary oxaheterocyclenyl includes 3,4-dihydro-2H-pyran, dihydrofuranyl, and fluorodihydro-furanyl. An exemplary multicyclic oxaheterocyclenyl is 7-oxabicyclo[2.2.1]heptenyl. Exemplary monocyclic thioheterocyclenyl includes dihydrothiophenyl and dihydrothiopyranyl.

"Heterocyclenylaryl" means a fused aryl and heterocyclenyl. Particular heterocyclenylaryl is one wherein the aryl thereof is phenyl and the heterocyclenyl consists of about 5 to about 6 ring atoms. A heterocyclenylaryl is bonded through any atom of the aryl thereof capable of such bonding. The designation of the aza, oxa or thio as a prefix before heterocyclenyl portion of the fused heterocyclenylaryl defines that at least a nitrogen, oxygen or sulfur atom is present, respectively, as a ring atom. The nitrogen atom of a heterocyclenylaryl may be a basic nitrogen atom. The nitrogen or sulfur atom of the heterocyclenyl portion of the heterocyclenylaryl may also be optionally oxidized to the corresponding N-oxide, S-oxide or S,S-dioxide. Exemplary heterocyclenylaryl include 3H-indolinyl, 1H-2-oxoquinolyl, 2H-1-oxoisoquinolyl, 1,2-di-hydroquinolinyl, 3,4-dihydroquinolinyl, 1,2-dihydroisoquinolinyl, and 3,4-dihydroisoquinolinyl.

"Heterocyclenylheteroaryl" means a fused heteroaryl and heterocyclenyl. Particular heterocyclenylheteroaryl is one wherein the heteroaryl thereof consists of about 5 to about 6 ring atoms and the heterocyclenyl consists of about 5 to about 6 ring atoms. A heterocyclenylheteroaryl is bonded through any atom of the heteroaryl thereof capable of such bonding. The designation of the aza, oxa or thio as a prefix before the heteroaryl or heterocyclenyl portion of the heterocyclenylheteroaryl define that at least a nitrogen, oxygen or sulfur atom is present, respectively, as a ring atom. The nitrogen atom of an azaheterocyclenylheteroaryl may be a basic nitrogen atom. The nitrogen or sulfur atom of the heteroaryl or heterocyclyl portion of the heterocyclenylheteroaryl may also be optionally oxidized to the corresponding N-oxide, S-oxide or S,S-dioxide. Exemplary heterocyclenylheteroaryl includes 7,8-dihydro[1,7]naphthyridinyl, 1,2-dihydro[2,7]-naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyridinyl and 1,2-dihydro-2,6-naphthyridinyl.

"Heterocyclyl" means a non-aromatic saturated monocyclic or multicyclic ring system of about 3 to about 10 carbon atoms, in which one or more of the atoms in the ring system is/are hetero element(s) other than carbon, for example nitrogen, oxygen or sulfur. A particular ring system contains about 5 to about 10 carbon atoms, and from 1 to 3 heteroatoms. Particular ring sizes of the ring system include about 5 to about 6 ring atoms; and such particular ring sizes are also referred to as "lower". The designation of the aza, oxa or thio as a prefix before heterocyclyl define that at least a nitrogen, oxygen or sulfur atom is present respectively as a ring atom. The nitrogen atom of a heterocyclyl may be a basic nitrogen atom. The nitrogen or sulfur atom of the heterocyclyl may also be optionally oxidized to 20 the corresponding N-oxide, S-oxide or S,S-dioxide. Exemplary monocyclic heterocyclyl includes piperidyl, pyrrolidinyl, piperazinyl, morpholinyl, thiomorpholinyl, thiazolidinyl, 1,3-dioxolanyl, 1,4-dioxanyl, THFyl, tetrahydrothiophenyl, and tetrahydrothiopyranyl.

"Heterocyclylaryl" means a fused aryl and heterocyclyl. Particular heterocyclylaryl is one wherein the aryl thereof is phenyl and the heterocyclyl consists of about 5 to about 6 ring atoms. A heterocyclylaryl is bonded through any atom of the aryl moiety thereof capable of such bonding. The designation of the aza, oxa or thio as a prefix before heterocyclyl portion of the heterocyclylaryl defines that at least a nitrogen, oxygen or sulfur atom is present, respectively, as a ring atom. The nitrogen atom of a heterocyclylaryl may be a basic nitrogen atom. The nitrogen or sulfur atom of the heterocyclyl portion of the heterocyclylaryl may also be optionally oxidized to the corresponding N-oxide, S-oxide or S,S-dioxide. Exemplary heterocyclylaryl includes indolinyl, 1,2,3,4-tetrahydroisoquinoline, 1,2,3,4-tetrahydroquinoline, 1H-2,3-dihydroisoindol-2-yl, and 2,3-dihydrobenz[f]isoindol-2-yl, and 1,2,3,4-tetrahydrobenz[g]-isoquinolin-2-yl.

"Heterocyclylheteroaryl" means a fused heteroaryl and heterocyclyl. Particular heterocyclylheteroaryl is one wherein the heteoraryl thereof consists of about 5 to about 6 ring atoms and the heterocyclyl consists of about 5 to about 6 ring atoms. A heterocyclylheteroaryl is bonded through any atom of the heterocyclyl thereof capable of such bonding. The designation of the aza, oxa or thio as a prefix before the heteroaryl or heterocyclyl portion of the heterocyclylheteroaryl defines that at least a nitrogen, oxygen or sulfur atom is present, respectively, as a ring atom. The nitrogen atom of a heterocyclylheteroaryl may be a basic nitrogen atom. The nitrogen or sulfur atom of the heteroaryl or heterocyclyl portion of the heterocyclylheteroaryl may also be optionally oxidized to the corresponding N-oxide, S-oxide or S,S-dioxide. Exemplary heterocyclylheteroaryl includes 2,3-dihydro-1H-pyrrol[3,4-b]quinolin-2-yl, 1,2,3,4-tetrahydrobenz[b][1,7]naphthyridin-2-yl, 1,2,3,4-tetrahydrobenz[b][1,6]naphthyridin-2-yl, 1,2,3,4-tetra-hydro-9H-pyrido[3,4-b]indol-2-yl, 1,2,3,4-tetrahydro-9H-pyrido[4,3-b]indol-2-yl, 2,3-dihydro-1H-pyrrolo[3,4-b]indol-2-yl, 1H-2,3,4,5-tetrahydroazepino[3,4-b]indol-2-yl, 1H-2,3,4,5-tetra-hydroazepino[4,3-b]indol-3-yl, 1H-2,3,4,5-tetrahydroazepino[4,5-b]indol-2-yl, 5,6,7,8-tetra-hydro[1,7]naphthyridyl, 1,2,3,4-tetrhydro[2,7]naphthyridyl, 2,3-dihydro[1,4]dioxino[2,3-b]pyridyl, 2,3-dihydro-[1,4]dioxino[2,3-b]pyridyl, 3,4-dihydro-2H-1-oxa[4,6]diazanaphthalenyl, 4,5,6,7-tetrahydro-3H-imidazo[4,5-c]pyridyl, 6,7-dihydro[5,8]diazanaphthalenyl, 1,2,3,4-tetrahydro[1,5]-naphthyridinyl, 1,2,3,4-tetrahydro[1,6]naphthyridinyl, 1,2,3,4-tetrahydro[1,7]naphthyridinyl, 1,2,3,4-tetrahydro[1,8]naphthyridinyl, and 1,2,3,4-tetra-hydro[2,6]naphthyridinyl.

"Multicyclic alkaryl" means a multicyclic ring system including at least one aromatic ring fused to at least one non-aromatic ring that may be saturated or unsaturated, and may also contain in the ring system one or more heteroatoms, such as nitrogen, oxygen or sulfur. Exemplary multicyclic alkaryl includes arylcycloalkenyl, arylcycloalkyl, arylheterocyclenyl, arylheterocyclyl, cycloalkenylaryl, cycloalkylaryl, cycloalkenylheteroaryl, cycloalkylheteroaryl, heteroarylcycloalkenyl, heteroarylcycloalkyl, heteroarylheterocyclenyl, heteroarylheterocyclyl, heterocyclenylaryl, heterocyclenylheteroaryl, heterocyclylaryl, and heterocyclylheteroaryl. Particular multicyclic alkaryl groups are bicyclic rings that include one aromatic ring fused to one non-aromatic ring and that also may contain in the ring system one or more heteroatoms, such as nitrogen, oxygen or sulfur.

"Patient" includes human and other mammals.

"Pharmaceutically acceptable salts" refers to the non-toxic, inorganic and organic acid addition salts, and base addition salts, of compounds of the present invention. These salts may be prepared in situ during the final isolation and purification of the compounds or by separately reacting the purified compound in its free base form with a suitable organic or inorganic acid and isolating the salt thus formed. In some cases, the compounds themselves are capable of self-protonating basic sites on the molecule and forming an internal amphoteric salt.

Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-β-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts. See, for example S. M. Berge, et al., "Pharmaceutical Salts," *J. Pharm. Sci* 66, 1-19 (1977) that is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. A particular base addition salt is sodium salt or potassium salt. Suitable inorganic base addition salts are prepared from metal bases which include sodium hydride, sodium hydroxide, potassium hydroxide, calcium hydroxide, aluminum hydroxide, lithium hydroxide, magnesium hydroxide, and zinc hydroxide. Suitable amine base addition salts are prepared from amines which have sufficient basicity to form a stable salt, and particularly include those amines which are frequently used in medicinal chemistry because of their low toxicity and acceptability for medical use. Exemplary amine includes ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine.

"Solvate" means a physical association of a compound of the present invention with one or more solvent molecules. This physical association includes hydrogen bonding. In certain instances, the solvate will be capable of isolation, for example when one or more solvent molecules are incorporated in the crystal lattice of the crystalline solid. "Solvate" encompasses both solution-phase and insoluble solvates. Particular solvates include hydrates, ethanolates, and methanolates.

PARTICULAR EMBODIMENTS OF THE INVENTION

One particular embodiment of the invention is a compound of formula (I) wherein $R^1$ is phenyl, five or six membered heteroaryl, or $(C_5-C_6)$-cycloalkyl, each of which is optionally substituted by halo, $(C_1-C_6)$-alkyl, hydroxy, $(C_1-C_6)$-alkoxy, $(C_1-C_4)$-haloalkyl or $(C_1-C_4)$-haloalkoxy, or a hydrate, solvate or N-oxide thereof, or a pharmaceutically acceptable salt thereof.

Another particular embodiment of the invention is a compound of formula (I) wherein $R^1$ is phenyl or five or six membered heteroaryl, each of which is optionally substituted by halo, $(C_1-C_6)$-alkyl, hydroxy, $(C_1-C_6)$-alkoxy, $(C_1-C_4)$-haloalkyl or $(C_1-C_4)$-haloalkoxy, or a hydrate, solvate or N-oxide thereof, or a pharmaceutically acceptable salt thereof.

Another particular embodiment of the invention is a compound of formula (I) wherein $R^1$ is phenyl or five or six membered heteroaryl, each of which is optionally substituted by halo, $(C_1-C_6)$-alkyl, hydroxy, $(C_1-C_6)$-alkoxy, $(C_1-C_4)$-haloalkyl or $(C_1-C_4)$-haloalkoxy, or a hydrate, solvate or N-oxide thereof, or a pharmaceutically acceptable salt thereof, provide that when $R^1$ is phenyl or six membered heteroaryl, then it is only optionally substituted at the ortho or meta position.

Another particular embodiment of the invention is a compound of formula (I) wherein $R^1$ is phenyl, pyridyl, thiazolyl, imidazolyl or oxdiazolyl, each of which is optionally substituted by halo, $(C_1-C_6)$-alkyl, hydroxy, $(C_1-C_6)$-alkoxy, $(C_1-C_4)$-haloalkyl or $(C_1-C_4)$-haloalkoxy, or a hydrate, solvate or N-oxide thereof, or a pharmaceutically acceptable salt thereof.

Another particular embodiment of the invention is a compound of formula (I) wherein $R^1$ is phenyl or pyridyl, each of which is optionally substituted at the ortho or meta position by halo, $(C_1-C_6)$-alkyl, hydroxy, $(C_1-C_6)$-alkoxy, $(C_1-C_4)$-haloalkyl or $(C_1-C_4)$-haloalkoxy, or a hydrate, solvate or N-oxide thereof, or a pharmaceutically acceptable salt thereof.

Another particular embodiment of the invention is a compound of formula (I) wherein $R^1$ is phenyl optionally substituted by halo, $(C_1-C_6)$-alkyl, hydroxy, $(C_1-C_6)$-alkoxy, $(C_1-C_4)$-haloalkyl or $(C_1-C_4)$-haloalkoxy, or a hydrate, solvate or N-oxide thereof, or a pharmaceutically acceptable salt thereof.

Another particular embodiment of the invention is a compound of formula (I) wherein $R^1$ is phenyl optionally substituted at the ortho or meta position by halo, $(C_1-C_6)$-alkyl, hydroxy, $(C_1-C_6)$-alkoxy, $(C_1-C_4)$-haloalkyl or $(C_1-C_4)$-haloalkoxy, or a hydrate, solvate or N-oxide thereof, or a pharmaceutically acceptable salt thereof.

Another particular embodiment of the invention is a compound of formula (I) wherein $R^1$ is phenyl optionally substituted by halo, or a hydrate, solvate or N-oxide thereof, or a pharmaceutically acceptable salt thereof.

Another particular embodiment of the invention is a compound of formula (I) wherein $R^1$ is phenyl optionally substituted at the ortho or meta position by halo, or a hydrate, solvate or N-oxide thereof, or a pharmaceutically acceptable salt thereof.

Another particular embodiment of the invention is a compound of formula (I) wherein $R^1$ is 2-fluorophenyl or 3-fluorophenyl, or a hydrate, solvate or N-oxide thereof, or a pharmaceutically acceptable salt thereof.

Another particular embodiment of the invention is a compound of formula (I) wherein $R^2$ is hydrogen, or a hydrate, solvate or N-oxide thereof, or a pharmaceutically acceptable salt thereof.

Another particular embodiment of the invention is a compound of formula (I) wherein $R^2$ is methyl, or a hydrate, solvate or N-oxide thereof, or a pharmaceutically acceptable salt thereof.

Another particular embodiment of the invention is a compound of formula (I) wherein $L^1$ is a bond, or a hydrate, solvate or N-oxide thereof, or a pharmaceutically acceptable salt thereof.

Another particular embodiment of the invention is a compound of formula (I) wherein $L^1$ is $(C_1-C_3)$-alkylene, or a hydrate, solvate or N-oxide thereof, or a pharmaceutically acceptable salt thereof.

Another particular embodiment of the invention is a compound of formula (I) wherein $L^1$ is —$CH_2$—, or a hydrate, solvate or N-oxide thereof, or a pharmaceutically acceptable salt thereof.

Another particular embodiment of the invention is a compound of formula (I) wherein:

$R^3$ is cycloalkyl, cycloalkenyl, aryl, heteroaryl, heterocyclyl, heterocyclenyl, or multicyclic alkaryl, each of which is optionally substituted by:
  acyl, cyano, nitro, halo, hydroxy, carboxy, amidino, $R^5O-C(=O)-C(=N-OR^4)-$, $Y^1Y^2N-$, $Y^1Y^2N-C(=O)-$, $Y^1Y^2N-C(=O)-O-$, $Y^1Y^2N-SO_2-$, $R^7-SO_2-NR^6-$, $R^7-C(=O)-NR^6-$, $Y^1Y^2N-(C_1-C_4)$-alkylene-$SO_2-(C_1-C_4)$-alkylene-, or
  alkyl, alkenyl, alkynyl, alkoxy, alkoxycarbonyl, alkylthio, alkylsulfinyl, or alkylsulfonyl, each of which is optionally substituted by:
    halo, alkoxy, haloalkoxy, hydroxy, carboxy, alkoxycarbonyl, $-P(=O)$-(alkoxy)$_2$, $Y^1Y^2N-$, $Y^1Y^2N-SO_2-$, $R^7-SO_2-NR^6-$,
    aryl or heteroaryl, each of which is optionally substituted by alkyl, halo, haloalkyl, alkoxy, haloalkoxy, hydroxy, amino, alkylamino, dialkylamino, carboxy, or alkoxycarbonyl, or
    heterocyclyl or arylheterocyclyl, each of which is optionally substituted by oxo or alkyl, or
  aryl, heteroaryl, aroyl, heteroaroyl, aryloxy, heteroaryloxy, or heterocyclyl, each of which is optionally substituted by alkyl, haloalkyl, halo, alkoxy, haloalkoxy, hydroxy, carboxy, alkoxycarbonyl, $-P(=O)$-(alkoxy)$_2$, $Y^1Y^2N-$, or $Y^1Y^2N-SO_2-$, and
when $R^3$ is cycloalkyl, cycloalkenyl, heterocyclyl, heterocyclenyl or multicyclic alkaryl, it is also optionally substituted by oxo, or a hydrate, solvate or N-oxide thereof, or a pharmaceutically acceptable salt thereof.

Another particular embodiment of the invention is a compound of formula (I) wherein $R^3$ is phenyl, pyridyl, thiazolyl, imidazolyl, oxdiazolyl, imidazolyl, pyrimidinyl, thiophenyl, oxazolyl, cycloalkyl, benzooxazolyl, 1,2,4-thiadiazolyl, 1,3,4-thiadiazolyl, tetrahydropyranyl, piperidinyl, furanyl, benzo[1,3]dioxolyl, benzothiazolyl, imidazolidinyl, indazolyl, benzoimidazolyl, indolyl, benzofuranyl, or 1,3-dihydro-benzo[c]isothiazolyl, each of which is optionally substituted by:
  acyl, cyano, nitro, halo, hydroxy, carboxy, amidino, $R^5O-C(=O)-C(=N-OR^4)-$, $Y^1Y^2N-$, $Y^1Y^2N-C(=O)-$, $Y^1Y^2N-C(=O)-O-$, $Y^1Y^2N-SO_2-$, $R^7-SO_2-NR^6-$, $R^7-C(=O)-NR^6-$, $Y^1Y^2N-(C_1-C_4)$-alkylene-$SO_2-(C_1-C_4)$-alkylene-, or alkyl, alkenyl, alkynyl, alkoxy, alkoxycarbonyl, alkylthio, alkylsulfinyl, or alkylsulfonyl, each of which is optionally substituted by:
    halo, alkoxy, haloalkoxy, hydroxy, carboxy, alkoxycarbonyl, $-P(=O)$-(alkoxy)$_2$, $Y^1Y^2N-$, $Y^1Y^2N-SO_2-$, $R^7-SO_2-NR^6-$,
    aryl or heteroaryl, each of which is optionally substituted by alkyl, halo, haloalkyl, alkoxy, haloalkoxy, hydroxy, amino, alkylamino, dialkylamino, carboxy, or alkoxycarbonyl, or
    heterocyclyl or arylheterocyclyl, each of which is optionally substituted by oxo or alkyl, or
  aryl, heteroaryl, aroyl, heteroaroyl, aryloxy, heteroaryloxy, or heterocyclyl, each of which is optionally substituted by alkyl, haloalkyl, halo, alkoxy, haloalkoxy, hydroxy, carboxy, alkoxycarbonyl, $-P(=O)$-(alkoxy)$_2$, $Y^1Y^2N-$, or $Y^1Y^2N-SO_2-$, and
when $R^3$ is cycloalkyl, tetrahydropyranyl, piperidinyl, imidazolidinyl, or 1,3-dihydro-benzo[c]isothiazolyl, it is also optionally substituted by oxo, or a hydrate, solvate or N-oxide thereof, or a pharmaceutically acceptable salt thereof.

Another particular embodiment of the invention is a compound of formula (I) wherein:

$R^3$ is phenyl, pyridyl, thiazolyl, imidazolyl, oxodiazolyl, imidazolyl, pyrimidinyl, thiophenyl, oxazolyl, cycloalkyl, benzooxazolyl, 1,2,4-thiadiazolyl, 1,3,4-thiadiazolyl, tetrahydropyranyl, piperidinyl, furanyl, benzo[1,3]dioxolyl, benzothiazolyl, imidazolidinyl, indazolyl, benzoimidazolyl, indolyl, benzofuranyl, or 1,3-dihydro-benzo[c]isothiazolyl, each of which is optionally substituted by:
  nitro, halo, hydroxy, carboxy, amidino, $R^5O-C(=O)-C(=N-OR^4)-$, $Y^1Y^2N-$, $Y^1Y^2N-C(=O)-$, $Y^1Y^2N-SO_2-$, $R^7-SO_2-NR^6-$, $R^7-C(=O)-NR^6-$, alkoxy, alkoxycarbonyl, alkylthio, alkylsulfonyl, aryl, heteroaryl, or alkyl optionally substituted by:
    halo, carboxy, alkoxycarbonyl, aryl or heteroaryl, $-P(=O)$-(alkoxy)$_2$, $Y^1Y^2N-$, $Y^1Y^2N-SO_2-$, $R^7-SO_2-NR^6$ or
    heterocyclyl or arylheterocyclyl, each of which is optionally substituted by oxo, or
  heterocyclyl optionally substituted by $Y^1Y^2N-$, and
when $R^3$ is cycloalkyl, tetrahydropyranyl, piperidinyl, imidazolidinyl, or 1,3-dihydro-benzo[c]isothiazolyl, it is also optionally substituted by oxo; and
$Y^1$ and $Y^2$ are each independently hydrogen, cycloalkyl, or alkyl optionally substituted by hydroxy, alkoxy, amino, alkylamino, dialkylamino, heteroaryl, or heterocyclyl optionally substituted by alkyl, or a hydrate, solvate or N-oxide thereof, or a pharmaceutically acceptable salt thereof.

Another particular embodiment of the invention is a compound of formula (I) wherein $R^3$ is phenyl optionally substituted by:
  acyl, cyano, nitro, halo, hydroxy, carboxy, amidino, $R^5O-C(=O)-C(=N-OR^4)-$, $Y^1Y^2N-$, $Y^1Y^2N-C(=O)-$, $Y^1Y^2N-C(=O)-O-$, $Y^1Y^2N-SO_2-$, $R^7-SO_2-NR^6-$, $R^7-C(=O)-NR^6-$, $Y^1Y^2N-(C_1-C_4)$-alkylene-$SO_2-(C_1-C_4)$-alkylene-, or alkyl, alkenyl, alkynyl, alkoxy, alkoxycarbonyl, alkylthio, alkylsulfinyl, or alkylsulfonyl, each of which is optionally substituted by:
    halo, alkoxy, haloalkoxy, hydroxy, carboxy, alkoxycarbonyl, $-P(=O)$-(alkoxy)$_2$, $Y^1Y^2N-$, $Y^1Y^2N-SO_2-$, $R^7-SO_2-NR^6-$,
    aryl or heteroaryl, each of which is optionally substituted by alkyl, halo, haloalkyl, alkoxy, haloalkoxy, hydroxy, amino, alkylamino, dialkylamino, carboxy, or alkoxycarbonyl, or
    heterocyclyl or arylheterocyclyl, each of which is optionally substituted by oxo or alkyl, or
  aryl, heteroaryl, aroyl, heteroaroyl, aryloxy, heteroaryloxy, or heterocyclyl, each of which is optionally substituted by alkyl, haloalkyl, halo, alkoxy, haloalkoxy, hydroxy, carboxy, alkoxycarbonyl, $-P(=O)$-(alkoxy)$_2$, $Y^1Y^2N-$, or $Y^1Y^2N-SO_2-$ or a hydrate, solvate or N-oxide thereof, or a pharmaceutically acceptable salt thereof.

Another particular embodiment of the invention is a compound of formula (I) wherein:

$R^3$ is phenyl optionally substituted by:
  nitro, halo, hydroxy, carboxy, amidino, $R^5O-C(=O)-C(=N-OR^4)-$, $Y^1Y^2N-$, $Y^1Y^2N-C(=O)-$, $Y^1Y^2N-SO_2-$, $R^7-SO_2-NR^6-$, $R^7-C(=O)-NR^6-$, alkoxy, alkoxycarbonyl, alkylthio, alkylsulfonyl, aryl, heteroaryl, or
  alkyl optionally substituted by:
    halo, carboxy, alkoxycarbonyl, aryl or heteroaryl, $-P(=O)$-(alkoxy)$_2$, $Y^1Y^2N-$, $Y^1Y^2N-SO_2-$, R⁷—SO₂—NR⁶-, or heterocyclyl or arylheterocyclyl, each of which is optionally substituted by oxo, or
heterocyclyl optionally substituted by Y¹Y²N—, and
Y¹ and Y² are each independently hydrogen, cycloalkyl, or alkyl optionally substituted by hydroxy, alkoxy, amino, alkylamino, dialkylamino, heteroaryl, or heterocyclyl optionally substituted by alkyl,
or a hydrate, solvate or N-oxide thereof, or a pharmaceutically acceptable salt thereof.

Another particular embodiment of the invention is a compound of formula (I) wherein R³ is phenyl optionally substituted by:
Y¹Y²N—SO₂—, R⁷—SO₂—NR⁶-, alkylsulfonyl, or
alkyl substituted by Y¹Y²N—SO₂—, R⁷—SO₂—NR⁶—,
or a hydrate, solvate or N-oxide thereof, or a pharmaceutically acceptable salt thereof Another particular embodiment of the invention is a compound of formula (I) wherein:
R³ is phenyl optionally substituted by:
Y¹Y²N—SO₂—, R⁷—SO₂—NR⁶—, alkylsulfonyl, or
alkyl substituted by Y¹Y²N—SO₂—, R⁷—SO₂—NR⁶—; and
Y¹ and Y² are each independently hydrogen, cycloalkyl, or alkyl optionally substituted by hydroxy, alkoxy, amino, alkylamino, dialkylamino, heteroaryl, or heterocyclyl optionally substituted by alkyl,
or a hydrate, solvate or N-oxide thereof, or a pharmaceutically acceptable salt thereof.

Another particular embodiment of the invention is a compound of formula (I), which is
2-Phenyl-pyrimidine-5-carboxylic acid benzylamide,
2-Pyridin-4-yl-pyrimidine-5-carboxylic acid phenylamide,
2-Pyridin-3-yl-pyrimidine-5-carboxylic acid phenylamide,
2-Pyridin-2-yl-pyrimidine-5-carboxylic acid phenylamide,
2-(3-Fluoro-phenyl)-pyrimidine-5-carboxylic acid phenylamide,
2-(4-Fluoro-phenyl)-pyrimidine-5-carboxylic acid phenylamide,
2-(2-Fluoro-phenyl)-pyrimidine-5-carboxylic acid phenylamide,
2-Phenyl-pyrimidine-5-carboxylic acid (2,2-dioxo-2,3-dihydro-1H-2lamda*6*-benzo[c]isothiazol-5-yl)-amide,
2-Phenyl-pyrimidine-5-carboxylic acid [1-(1H-imidazol-2-ylmethyl-piperidin-4-yl]-amide,
2-Phenyl-pyrimidine-5-carboxylic acid (6-dimethylamino-pyridin-3-ylmethyl)-amide,
2-Phenyl-pyrimidine-5-carboxylic acid [2-(2-pyrrolidin-1-yl-ethyl)-benzooxazol-6-yl]-amide,
2-Phenyl-pyrimidine-5-carboxylic acid 4-sulfamoyl-benzylamide,
2-Phenyl-pyrimidine-5-carboxylic acid [2-(4-sulfamoyl-phenyl)-ethyl]-amide,
(R)-2-Phenyl-pyrimidine-5-carboxylic acid [4-(2-oxo-oxazolidin-4-ylmethyl)-phenyl]-amide,
2-Phenyl-pyrimidine-5-carboxylic acid (6-acetylamino-pyridin-3-yl)-amide,
2-Phenyl-pyrimidine-5-carboxylic acid (3-carbamoyl-phenyl)-amide,
2-Phenyl-pyrimidine-5-carboxylic acid (3-methylcarbamoyl-phenyl)-amide,
2-Phenyl-pyrimidine-5-carboxylic acid (4-hydroxy-cyclohexyl)-amide,
4-methyl-2-[(2-phenyl-pyrimidin-5-carbonyl)-amino]-thiazole-5-carboxylic acid ethyl ester,
{2-[(2-phenyl-pyrimidine-5-carbonyl)-amino]-thiazol-4-yl}-acetic acid ethyl ester,
4-methyl-2-[(2-phenyl-pyrimidin-5-carbonyl)-amino]-thiazole-5-carboxylic acid,
{2-[(2-phenyl-pyrimidine-5-carbonyl)-amino]-thiazol-4-yl}-acetic acid,
2-Phenyl-pyrimidine-5-carboxylic acid 4-methylsulfamoyl-benzylamide,
2-Phenyl-pyrimidine-5-carboxylic acid 4-dimethylsulfamoyl-benzylamide,
2-Phenyl-pyrimidine-5-carboxylic acid (3,5-difluoro-phenyl)-amide,
2-Phenyl-pyrimidine-5-carboxylic acid pyridin-2-ylamide,
2-Phenyl-pyrimidine-5-carboxylic acid thiazol-2-ylamide,
2-Phenyl-pyrimidine-5-carboxylic acid (3-sulfamoyl-phenyl)-amide,
2-Phenyl-pyrimidine-5-carboxylic acid (2-oxo-1,2-dihydro-pyrimidin-4-yl)-amide,
2-Phenyl-pyrimidine-5-carboxylic acid (4-sulfamoyl-phenyl)-amide,
2-Phenyl-pyrimidine-5-carboxylic acid pyrimidin-4-ylamide,
2-Phenyl-pyrimidine-5-carboxylic acid (1-pyridin-3-ylmethyl-piperidin-4-yl)-amide,
2-Phenyl-pyrimidine-5-carboxylic acid [2-(2-oxo-imidazolidin-1-yl)-ethyl]-amide,
2-Phenyl-pyrimidine-5-carboxylic acid [2-(1H-imidazol-4-yl)-ethyl]-amide,
2-Phenyl-pyrimidine-5-carboxylic acid (tetrahydro-pyran-4-ylmethyl)-amide,
2-Phenyl-pyrimidine-5-carboxylic acid (3-trifluoromethyl-phenyl)-amide,
2-Phenyl-pyrimidine-5-carboxylic acid (2H-pyrazol-3-yl)-amide,
2-Phenyl-pyrimidine-5-carboxylic acid (1-methyl-piperidin-4-yl)-amide,
2-Phenyl-pyrimidine-5-carboxylic acid pyrimidin-2-ylamide,
2-(3,5-difluoro-phenyl)-pyrimidine-5-carboxylic acid 3-methylsulfamoyl-benzylamide,
2-(2,5-difluoro-phenyl)-pyrimidine-5-carboxylic acid 3-methylsulfamoyl-benzylamide,
2-(4-difluorophenyl)-4-methylpyrimidine-5-carboxylic acid-3-methylsulfamoyl-benzylamide,
2-(2-pyridyl)-pyrimidine-5-carboxylic acid-3-methylsulfamoyl-benzylamide,
2-(3-pyridyl)-4-methyl-pyrimidine-5-carboxylic acid-3-methylsulfamoyl-benzylamide,
2-(3-Fluoro-phenyl)-pyrimidine-5-carboxylic acid 3-ethylsulfamoyl-benzylamide,
2-(3-Fluoro-phenyl)-pyrimidine-5-carboxylic acid 3-(2-ethoxy-ethylsulfamoyl)-benzylamide,
2-(3-Fluoro-phenyl)-pyrimidine-5-carboxylic acid 3-(2-hydroxy-propylsulfamoyl)-benzylamide,
2-(3-Fluoro-phenyl)-pyrimidine-5-carboxylic acid 3-cyclopropylsulfamoyl-benzylamide,
2-(3-Fluoro-phenyl)-pyrimidine-5-carboxylic acid 3-(3-hydroxy-propylsulfamoyl)-benzylamide,
2-(3-Fluoro-phenyl)-pyrimidine-5-carboxylic acid 3-(2-methoxy-ethylsulfamoyl)-benzylamide,
2-(3-Fluoro-phenyl)-pyrimidine-5-carboxylic acid 3-(3-methoxy-propylsulfamoyl)-benzylamide,
2-(3-Fluoro-phenyl)-pyrimidine-5-carboxylic acid 3-(4-methoxy-butylsulfamoyl)-benzylamide,
2-(3-Fluoro-phenyl)-pyrimidine-5-carboxylic acid 3-cyclohexylsulfamoyl-benzylamide,
2-(3-Fluoro-phenyl)-pyrimidine-5-carboxylic acid 3-(2-hydroxy-1,1-dimethyl-ethylsulfamoyl)-benzylamide, 2-(3-Fluoro-phenyl)-pyrimidine-5-carboxylic acid 3-sulfamoyl-benzylamide,
2-(3-Fluoro-phenyl)-pyrimidine-5-carboxylic acid 3-(2-morpholin-4-yl-ethylsulfamoyl)-benzylamide,
2-(3-Fluoro-phenyl)-pyrimidine-5-carboxylic acid 3-(2-piperidin-1-yl-ethylsulfamoyl)-benzylamide,
2-(3-Fluoro-phenyl)-pyrimidine-5-carboxylic acid 3-[2-(1-methyl-pyrrolidin-2-yl)-ethylsulfamoyl]-benzylamide,
2-(3-Fluoro-phenyl)-pyrimidine-5-carboxylic acid 3-[(1-ethyl-pyrrolidin-2-ylmethyl)-sulfamoyl]-benzylamide,
2-(3-Fluoro-phenyl)-pyrimidine-5-carboxylic acid 3-[2-(1H-imidazol-4-yl)-ethylsulfamoyl]-benzylamide,
2-(3-Fluoro-phenyl)-pyrimidine-5-carboxylic acid 3-[3-(2-methyl-piperidin-1-yl)-propylsulfamoyl]-benzylamide,
2-(3-Fluoro-phenyl)-pyrimidine-5-carboxylic acid 3-(3-pyrrolidin-1-yl-propylsulfamoyl)-benzylamide,
2-(3-Fluoro-phenyl)-pyrimidine-5-carboxylic acid 3-(2-dimethylamino-ethylsulfamoyl)-benzylamide,
2-(3-Fluoro-phenyl)-pyrimidine-5-carboxylic acid 3-(2-diethylamino-ethylsulfamoyl)-benzylamide,
2-(3-Fluoro-phenyl)-pyrimidine-5-carboxylic acid 3-(3-dimethylamino-2,2-dimethyl-propylsulfamoyl)-benzylamide,
2-(3-Fluoro-phenyl)-pyrimidine-5-carboxylic acid 3-(5-dimethylamino-pentylsulfamoyl)-benzylamide,
2-(3-Fluoro-phenyl)-pyrimidine-5-carboxylic acid 3-(2-diisopropylamino-ethylsulfamoyl)-benzylamide,
2-(3-Fluoro-phenyl)-4-methyl-pyrimidine-5-carboxylic acid 3-(methanesulfonylamino-methyl)-benzylamide,
2-(3-Fluoro-phenyl)-4-methyl-pyrimidine-5-carboxylic acid 3-[(propane-2-sulfonylamino)-methyl]-benzylamide,
2-(3-Fluoro-phenyl)-4-methyl-pyrimidine-5-carboxylic acid 3-methylsulfamoylmethyl-benzylamide,
2-(3-Fluoro-phenyl)-4-methyl-pyrimidine-5-carboxylic acid 3-(isopropylsulfamoyl-methyl)-benzylamide,
2-(3-Fluoro-phenyl)-pyrimidine-5-carboxylic acid 3-(methanesulfonylamino-methyl)-benzylamide,
2-(3-Fluoro-phenyl)-pyrimidine-5-carboxylic acid 3-[(propane-2-sulfonylamino)-methyl]-benzylamide,
2-(3-Fluoro-phenyl)-pyrimidine-5-carboxylic acid 3-methylsulfamoylmethyl-benzylamide,
2-(3-Fluoro-phenyl)-pyrimidine-5-carboxylic acid 3-(isopropylsulfamoyl-methyl)-benzylamide,
2-(3-Fluoro-phenyl)-pyrimidine-5-carboxylic acid (2-methanesulfonylamino-pyridin-4-ylmethyl)-amide,
2-(5-Methyl-[1,2,4]oxadiazole-3-yl)-pyrimidine-5-carboxylic acid (tetrahydro-pyran-4-yl)-amide,
2-(5-Methyl-[1,2,4]oxadiazole-3-yl)-pyrimidine-5-carboxylic acid 4-sulfamoyl-benzeneamide,
2-(5-Methyl-[1,2,4]oxadiazol-3-yl)-pyrimidine-5-carboxylic acid (3-phenyl-[1,2,4]thiadiazol-5-yl)-amide,
2-(3-Fluoro-phenyl)-pyrimidine-5-carboxylic acid 3-(morpholine-4-sulfonyl)-benzylamide,
2-Pheny-pyrimidine-5-carboxylic acid 3,4-dimethoxyl-benzylamide,
2-Pheny-pyrimidine-5-carboxylic acid (2-benzo[1,3]dioxol-5-yl-ethyl)-amide,
2-Pheny-pyrimidine-5-carboxylic acid (1H-indazol-5-yl)-amide,
2-Phenyl-pyrimidine-5-carboxylic acid 4-[1,2,3]thiadiazol-5-yl)-benzylamide,
2-(3-Fluoro-phenyl)-4-methyl-pyrimidine-5-carboxylic acid 3-methylsulfamoyl-benzylamide,
4-Methyl-2-pyridin-2-yl-pyrimidine-5-carboxylic acid 3-methylsulfamoyl-benzylamide,
2-Pheny-pyrimidine-5-carboxylic acid 4-morpholin-4-yl-benzylamide,
6-[(2-Phenyl-pyrimidin-5-carbonyl)-amino]-1H-benzoimidazole-2-carboxylic acid methyl ester,
6-[(2-Phenyl-pyrimidin-5-carbonyl)-amino]-1H-benzoimidazole-2-carboxylic acid,
2-Pheny-pyrimidine-5-carboxylic acid (benzofuran-5-ylmethyl)-amide,
2-Pheny-pyrimidine-5-carboxylic acid 4-methanesulfonylamino-benzylamide,
2-Pheny-pyrimidine-5-carboxylic acid 4-carbamoyl-benzylamide,
2-Pheny-pyrimidine-5-carboxylic acid 3-(2-hydroxy-ethylsulfamoyl)-benzylamide,
2-Pheny-pyrimidine-5-carboxylic acid 4-(morpholin-4-sulfonyl)-benzylamide,
2-Pheny-pyrimidine-5-carboxylic acid 3-methylsulfamoyl-benzylamide,
2-Pheny-pyrimidine-5-carboxylic acid [2-(2-amino-4-methyl-thiazol-5-yl)-ethyl]-amide,
2-(3-Fluoro-phenyl)-pyrimidine-5-carboxylic acid 3-methylsulfamoyl-benzylamide,
{4-{[(2-Phenyl-pyrimidine-5-carbonyl)-amino]-benzyl}-phosphonic acid diethyl ester,
{4-[(2-Phenyl-pyrimidine-5-carbonyl)-amino]-butyl)-phosphonic acid diethyl ester,
{4-[(2-Phenyl-pyrimidine-5-carbonyl)-amino]-ethyl)-phosphonic acid diethyl ester,
{Phenyl-[(2-phenyl-pyrimidine-5-carbonyl)-amino]-methyl)-phosphonic acid diethyl ester,
2-(3-Fluoro-phenyl)-pyrimidine-5-carboxylic acid 3-methanesulfonyl)-benzylamide,
2-(3-Fluoro-phenyl)-pyrimidine-5-carboxylic acid (1-methanesulfonyl-piperidin-3-ylmethyl)-amide,
2-(3-Fluoro-phenyl)-pyrimidine-5-carboxylic acid (1-dimethanesulfamoyl-piperidin-3-ylmethyl)-amide,
2-(Phenyl)-pyrimidine-5-carboxylic acid 3-methanesulfonylamino-benzylamide,
2-(3-Fluoro-phenyl)-pyrimidine-5-carboxylic acid 3-acetylsulfamoyl-benzylamide,
2-(3-Fluoro-phenyl)-pyrimidine-5-carboxylic acid 3-(3-oxo-piperazine-1-sulfonyl)-benzylamide,
2-Pheny-pyrimidine-5-carboxylic acid (2-sulfamoyl-ethyl)-amide,
2-Pheny-pyrimidine-5-carboxylic acid (2-dimethylsulfamoyl-ethyl)-amide,
2-Phenyl-pyrimidine-5-carboxylic acid (3-phenyl-[1,2,4]thiadiazol-5-yl)-amide,
4-Methyl-2-phenyl-pyrimidine-5-carboxylic acid (3-phenyl-[1,2,4]thiadiazol-5-yl)-amide
2-(3-Fluoro-phenyl)-pyrimidine-5-carboxylic acid (3-phenyl-[1,2,4]thiadiazol-5-yl)amide,
2-(3-Fluoro-phenyl)-pyrimidine-5-carboxylic acid (tetrahydro-pyran-4-yl)-amide,
2-Cyclohexyl-pyrimidine-5-carboxylic acid phenylamide,
2-Phenyl-pyrimidine-5-carboxylic acid 3-amino-benzylamide,
2-(3-Pyridyl)-pyrimidine-5-carboxylic acid-3-methylsulfamoyl-benzylamide,
2-Pyrazol-1-yl-pyrimidine-5-carboxylic acid 4-sulfamoyl-benzylamide,
2-(2-Methyl-thiazol-4-yl)-pyrimidine-5-carboxylic acid (tetrahydro-pyran-4-yl)-amide,
2-Phenyl-pyrimidine-5-carboxylic acid (thiophen-2-ylmethyl)-amide,
2-Phenyl-pyrimidine-5-carboxylic acid (4-methyl-oxazol-2-yl)-amide,
Methoxyimino-{2-[(2-phenyl-pyrimidine-5-carbonyl)-amino]-thiazol-4-yl}-acetic acid ethyl ester, 2-Phenyl-pyrimidine-5-carboxylic acid (5-methylsulfanyl-[1,3,4]thiadiazol-2-yl)-amide,
2-[(2-Phenyl-pyrimidine-5-carbonyl)-amino]-benzothiazole-5-carboxylic acid ethyl ester,
(R)-2-Phenyl-pyrimidine-5-carboxylic acid (1-phenyl-ethyl)-amide,
2-Phenyl-pyrimidine-5-carboxylic acid [3-(1H-tetrazol-5-yl)-phenyl]-amide,
2-Phenyl-pyrimidine-5-carboxylic acid (1-carbamimidoyl-piperidin-4-ylmethyl)-amide,
5-[(2-Phenyl-pyrimidine-5-carbonyl)-amino]-1H-indole-3-carboxylic acid amide,
2-Phenyl-pyrimidine-5-carboxylic acid [3-(2-amino-thiazol-4-yl)-phenyl]-amide,
2-Phenyl-pyrimidine-5-carboxylic acid {4-[2-(1,3-dioxo-1,3-dihydro-isoindol-2-yl)-ethyl]-thiazol-2-yl}-amide,
2-(3-Fluoro-phenyl)-pyrimidine-5-carboxylic acid [2-(pyrrolidine-1-sulfonyl)-ethyl]-amide,
[3-({[2-(3-Fluoro-phenyl)-4-methyl-pyrimidine-5-carbonyl]-amino}-methyl)-benzyl]-carbamic acid tert-butyl ester,
2-(3-Fluoro-phenyl)-pyrimidine-5-carboxylic acid 3-[(pyridin-2-ylmethyl)-sulfamoyl]-benzylamide,
2-(3-Fluoro-phenyl)-pyrimidine-5-carboxylic acid 3-(3-hydroxy-2,2-dimethyl-propylsulfamoyl)-benzylamide,
2-(3-Fluoro-phenyl)-pyrimidine-5-carboxylic acid 3-(2-hydroxy-2-methyl-propylsulfamoyl)-benzylamide,
2-(3-Fluoro-phenyl)-pyrimidine-5-carboxylic acid 3-[(tetrahydro-pyran-4-ylmethyl)-sulfamoyl]-benzylamide,
2-(3-Fluoro-phenyl)-pyrimidine-5-carboxylic acid 3-(4-hydroxy-butylsulfamoyl)-benzylamide,
2-(3-Fluoro-phenyl)-pyrimidine-5-carboxylic acid 3-[2-(2-hydroxy-ethoxy)-ethylsulfamoyl]-benzylamide,
2-(3-Fluoro-phenyl)-pyrimidine-5-carboxylic acid 3-[(tetrahydro-furan-2-ylmethyl)-sulfamoyl]-benzylamide,
2-(3-Fluoro-phenyl)-pyrimidine-5-carboxylic acid 3-isobutylsulfamoyl-benzylamide,
2-(3-Fluoro-phenyl)-pyrimidine-5-carboxylic acid (5-isopropylsulfamoyl-pyridin-3-ylmethyl)-amide,
2-(3-Fluoro-phenyl)-pyrimidine-5-carboxylic acid (5-methylsulfamoyl-pyridin-3-ylmethyl)-amide,
2-(3-Fluoro-phenyl)-pyrimidine-5-carboxylic acid (2-methylsulfamoyl-pyridin-4-ylmethyl)-amide,
2-(3-Fluoro-phenyl)-4-methyl-pyrimidine-5-carboxylic acid (2-methylsulfamoyl-pyridin-4-ylmethyl)-amide, or
2-(3-Fluoro-phenyl)-4-methyl-pyrimidine-5-carboxylic acid (5-isopropylsulfamoyl-pyridin-3-ylmethyl)-amide,
or a hydrate, solvate or N-oxide thereof, or a pharmaceutically acceptable salt thereof.

The present invention also includes within its scope a pharmaceutical composition comprising a pharmaceutically effective amount of a compound of the invention, in admixture with a pharmaceutically acceptable carrier.

Compounds of the present invention are PGDS inhibitors and thus, are useful for treating allergic and/or inflammatory disorders, particularly disorders such as allergic rhinitis, asthma and/or chronic obstructive pulmonary disease (COPD).

Accordingly, another aspect of the invention herein is directed to a method of treating a patient suffering from allergic rhinitis and/or asthma comprising administering to the patient a pharmaceutically effective amount of compound of formula (I).

References herein directed to treating should be understood to include prophylactic therapy to inhibit PGDS, as well as to treat an established acute or chronic or physiological conditions associated with PGDS to essentially cure a patient suffering therefrom, or ameliorate the physiological conditions associated therewith. Physiological conditions discussed herein include some, but not all, of the possible clinical situations where an anti-allergic rhinitis and/or asthma treatment is warranted. Those experienced in this field are well aware of the circumstances requiring treatment.

In practice, the compound of the present invention may be administered in pharmaceutically acceptable dosage form to humans and other mammals by topical or systemic administration, including oral, inhalational, rectal, nasal, buccal, sublingual, vaginal, colonic, parenteral (including subcutaneous, intramuscular, intravenous, intradermal, intrathecal and epidural), intracisternal and intraperitoneal. It will be appreciated that the particular route may vary with for example the physiological condition of the recipient.

"Pharmaceutically acceptable dosage forms" refers to dosage forms of the compound of the invention, and includes, for example, tablets, dragées, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington's Pharmaceutical Sciences, Mack Publishing Co., Easton, Pa., latest edition.

A particular aspect of the invention provides for the compound of the invention to be administered in the form of a pharmaceutical composition.

Pharmaceutically acceptable carriers include at least one component selected from the group comprising pharmaceutically acceptable carriers, diluents, coatings, adjuvants, excipients, or vehicles, such as preserving agents, fillers, disintegrating agents, wetting agents, emulsifying agents, emulsion stabilizing agents, suspending agents, isotonic agents, sweetening agents, flavoring agents, perfuming agents, coloring agents, antibacterial agents, antifungal agents, other therapeutic agents, lubricating agents, adsorption delaying or promoting agents, and dispensing agents, depending on the nature of the mode of administration and dosage forms.

Exemplary suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances.

Exemplary antibacterial and antifungal agents for the prevention of the action of microorganisms include parabens, chlorobutanol, phenol, sorbic acid, and the like.

Exemplary isotonic agents include sugars, sodium chloride, and the like.

Exemplary adsorption delaying agents to prolong absorption include aluminum monostearate and gelatin.

Exemplary adsorption promoting agents to enhance absorption include dimethyl sulfoxide and related analogs.

Exemplary diluents, solvents, vehicles, solubilizing agents, emulsifiers and emulsion stabilizers, include water, chloroform, sucrose, ethanol, isopropyl alcohol, ethyl carbonate, ethyl acetate, benzyl alcohol, tetrahydrofurfuryl alcohol, benzyl benzoate, polyols, propylene glycol, 1,3-butylene glycol, glycerol, polyethylene glycols, dimethylformamide, Tween® 60, Span®60, cetostearyl alcohol, myristyl alcohol, glyceryl mono-stearate and sodium lauryl sulfate, fatty acid esters of sorbitan, vegetable oils (such as cottonseed oil, groundnut oil, olive oil, castor oil and sesame oil) and injectable organic esters such as ethyl oleate, and the like, or suitable mixtures of these substances.

Exemplary excipients include lactose, milk sugar, sodium citrate, calcium carbonate and dicalcium phosphate.

Exemplary disintegrating agents include starch, alginic acids and certain complex silicates.

Exemplary lubricants include magnesium stearate, sodium lauryl sulfate, talc, as well as high molecular weight polyethylene glycols.

The choice of pharmaceutical acceptable carrier is generally determined in accordance with the chemical properties of the active compound such as solubility, the particular mode of administration and the provisions to be observed in pharmaceutical practice.

Pharmaceutical compositions of the present invention suitable for oral administration may be presented as discrete units such as a solid dosage form, such as capsules, cachets or tablets each containing a predetermined amount of the active ingredient, or as a powder or granules; as a liquid dosage form such as a solution or a suspension in an aqueous liquid or a non-aqueous liquid, or as an oil-in-water liquid emulsion or a water-in-oil liquid emulsion. The active ingredient may also be presented as a bolus, electuary or paste.

"Solid dosage form" means the dosage form of the compound of the invention is solid form, for example capsules, tablets, pills, powders, dragées or granules. In such solid dosage forms, the compound of the invention is admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, (i) lubricants, as for example, talc, calcium stearate, magnesium stearate, solid polyethylene glycols, sodium lauryl sulfate, (j) opacifying agents, (k) buffering agents, and agents which release the compound of the invention in a certain part of the intestinal tract in a delayed manner.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used. A mixture of the powdered compounds moistened with an inert liquid diluent may be molded in a suitable machine to make molded tablets. The tablets may optionally be coated or scored and may be formulated so as to provide slow or controlled release of the active ingredient therein.

Solid compositions may also be employed as fillers in soft and hard-filled gelatin capsules using such excipients as lactose or milk sugar as well as high molecular weight polyethylene glycols, and the like.

If desired, and for more effective distribution, the compound can be microencapsulated in, or attached to, a slow release or targeted delivery systems such as a biocompatible, biodegradable polymer matrices (e.g., poly(d,l-lactide co-glycolide)), liposomes, and microspheres and subcutaneously or intramuscularly injected by a technique called subcutaneous or intramuscular depot to provide continuous slow release of the compound(s) for a period of 2 weeks or longer. The compounds may be sterilized, for example, by filtration through a bacteria-retaining filter, or by incorporating sterilizing agents in the form of sterile solid compositions that can be dissolved in sterile water, or some other sterile injectable medium immediately before use.

"Liquid dosage form" means the dose of the active compound to be administered to the patient is in liquid form, for example, pharmaceutically acceptable emulsions, solutions, suspensions, syrups and elixirs. In addition to the active compound, the liquid dosage forms may contain inert diluents commonly used in the art, such solvents, solubilizing agents and emulsifiers.

When aqueous suspensions are used they can contain emulsifying agents or agents which facilitate suspension.

Pharmaceutical compositions suitable for topical administration mean formulations that are in a form suitable to be administered topically to a patient. The formulation may be presented as a topical ointment, salves, powders, sprays and inhalants, gels (water or alcohol based), creams, as is generally known in the art, or incorporated into a matrix base for application in a patch, which would allow a controlled release of compound through the transdermal barrier. When formulated in an ointment, the active ingredients may be employed with either a paraffinic or a water-miscible ointment base. Alternatively, the active ingredients may be formulated in a cream with an oil-in-water cream base. Formulations suitable for topical administration in the eye include eye drops wherein the active ingredient is dissolved or suspended in a suitable carrier, especially an aqueous solvent for the active ingredient. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

The oily phase of the emulsion pharmaceutical composition may be constituted from known ingredients, in a known manner. While the phase may comprise merely an emulsifier (otherwise known as an emulgent), it desirably comprises a mixture of at least one emulsifier with a fat or an oil or with both a fat and an oil. In a particular embodiment, a hydrophilic emulsifier is included together with a lipophilic emulsifier that acts as a stabilizer. Together, the emulsifier(s) with, or without, stabilizer(s) make up the emulsifying wax, and together with the oil and fat make up the emulsifying ointment base which forms the oily dispersed phase of the cream formulations.

If desired, the aqueous phase of the cream base may include, for example, a least 30% w/w of a polyhydric alcohol, i.e. an alcohol having two or more hydroxyl groups such as, propylene glycol, butane 1,3-diol, mannitol, sorbitol, glycerol and polyethylene glycol (including PEG 400) and mixtures thereof. The topical formulations may desirably include a compound that enhances absorption, or penetration of the active ingredient through the skin, or other affected areas.

The choice of suitable oils or fats for a composition is based on achieving the desired properties. Thus a cream should particularly be a non-greasy, non-staining and washable product with suitable consistency to avoid leakage from tubes or other containers. Straight or branched chain, mono- or dibasic alkyl esters such as di-isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used.

Pharmaceutical compositions suitable for rectal or vaginal administrations mean formulations that are in a form suitable to be administered rectally or vaginally to a patient and containing at least one compound of the invention. Suppositories are a particular form for such formulations that can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Pharmaceutical composition administered by injection may be by transmuscular, intravenous, intraperitoneal, and/or subcutaneous injection. The compositions of the present invention are formulated in liquid solutions, in particular in physiologically compatible buffers such as Hank's solution or Ringer's solution. In addition, the compositions may be formulated in solid form and redissolved or suspended immediately prior to use. Lyophilized forms are also included. The formulations are sterile and include emulsions, suspensions, aqueous and non-aqueous injection solutions, which may contain suspending agents and thickening agents and antioxidants, buffers, bacteriostats and solutes which render the formulation isotonic, and have a suitably adjusted pH, with the blood of the intended recipient.

Pharmaceutical composition of the present invention suitable for nasal or inhalational administration means compositions that are in a form suitable to be administered nasally or by inhalation to a patient. The composition may contain a carrier, in a powder form, having a particle size for example in the range 1 to 500 microns (including particle sizes in a range between 20 and 500 microns in increments of 5 microns such as 30 microns, 35 microns, etc.). Suitable compositions wherein the carrier is a liquid, for administration as for example a nasal spray or as nasal drops, include aqueous or oily solutions of the active ingredient. Compositions suitable for aerosol administration may be prepared according to conventional methods and may be delivered with other therapeutic agents. Inhalational therapy is readily administered by metered dose inhalers or any suitable dry powder inhaler, such as the Eclipse, Spinhaler®, or Ultrahaler® as described in patent application WO2004/026380, and U.S. Pat. No. 5,176,132.

Actual dosage levels of active ingredient(s) in the compositions of the invention may be varied so as to obtain an amount of active ingredient(s) that is (are) effective to obtain a desired therapeutic response for a particular composition and method of administration for a patient. A selected dosage level for any particular patient therefore depends upon a variety of factors including the desired therapeutic effect, on the route of administration, on the desired duration of treatment, the etiology and severity of the disease, the patient's condition, weight, sex, diet and age, the type and potency of each active ingredient, rates of absorption, metabolism and/or excretion and other factors.

Total daily dose of the compound of this invention administered to a patient in single or divided doses may be in amounts, for example, of from about 0.001 to about 100 mg/kg body weight daily and particularly 0.01 to 10 mg/kg/day. For example, in an adult, the doses are generally from about 0.01 to about 100, particularly about 0.01 to about 10, mg/kg body weight per day by inhalation, from about 0.01 to about 100, particularly 0.1 to 70, more especially 0.5 to 10, mg/kg body weight per day by oral administration, and from about 0.01 to about 50, particularly 0.01 to 10, mg/kg body weight per day by intravenous administration. The percentage of active ingredient in a composition may be varied, though it should constitute a proportion such that a suitable dosage shall be obtained. Dosage unit compositions may contain such amounts of such submultiples thereof as may be used to make up the daily dose. Obviously, several unit dosage forms may be administered at about the same time. A dosage may be administered as frequently as necessary in order to obtain the desired therapeutic effect. Some patients may respond rapidly to a higher or lower dose and may find much lower maintenance doses adequate. For other patients, it may be necessary to have long-term treatments at the rate of 1 to 4 doses per day, in accordance with the physiological requirements of each particular patient. It goes without saying that, for other patients, it will be necessary to prescribe not more than one or two doses per day.

The formulations can be prepared in unit dosage form by any of the methods well known in the art of pharmacy. Such methods include the step of bringing into association the pharmaceutically active ingredient with the carrier that constitutes one or more accessory ingredients. In general the formulations are prepared by uniformly and intimately bringing into association the active ingredient with liquid carriers or finely divided solid carriers or both, and then, if necessary, shaping the product.

The formulations may be presented in unit-dose or multi-dose containers, for example sealed ampoules and vials with elastomeric stoppers, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts, *Protecting Groups in Organic Synthesis*, 3rd edition, John Wiley & Sons, Inc., 1999.

A compound of formula (I), wherein $R^2$ is hydrogen, may be prepared, as shown in Scheme I below, by reacting an amidine compound, wherein $R^1$ is as defined herein, with a reagent of formula (A) to form a compound of formula (B), which directly or via its hydrolyzed product of formula (C), is coupled with an amine of formula (D), wherein $L^1$ and $R^3$ are as defined herein.

Scheme I

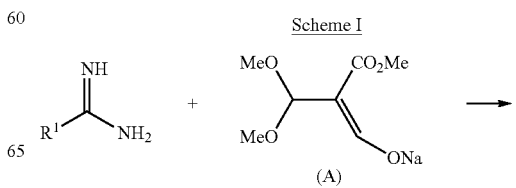

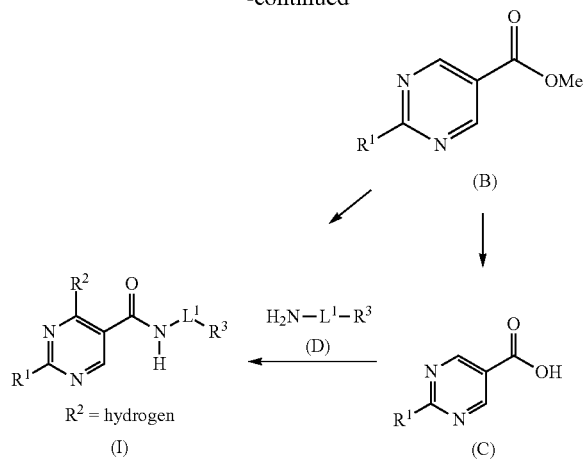

A compound of formula (I), wherein $R^2$ is $(C_1\text{-}C_4)$-alkyl, may be prepared, as shown in Scheme II below, by reacting an amidine compound, wherein $R^1$ is as defined herein, with a reagent of formula (E) to form a compound of formula (F), which directly or via its hydrolyzed product of formula (G), is coupled with an amine of formula (D), wherein $L^1$ and $R^3$ are as defined herein.

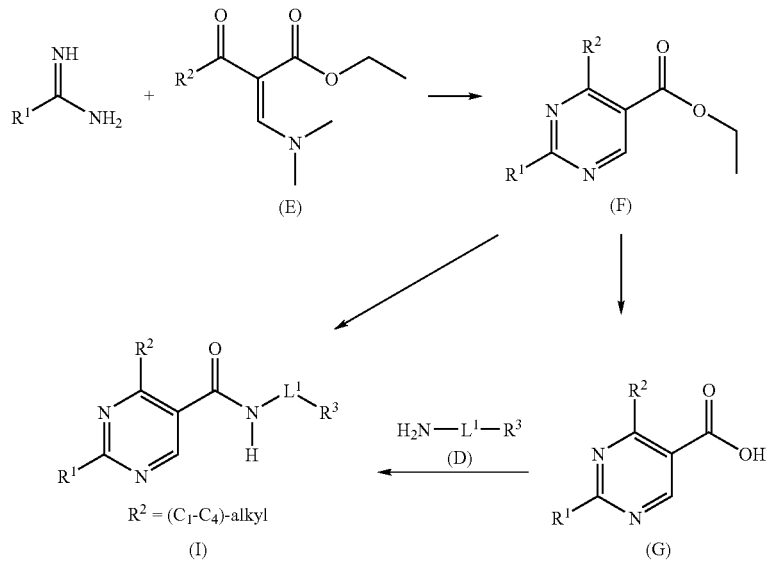

Compounds of the invention may also be prepared by interconversion of other compounds of the invention.

It will be appreciated that compounds of the present invention may contain asymmetric centers. These asymmetric centers may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of Formula (I) hereinabove. Such isomers can be separated from their mixtures, by the application or adaptation of known methods, for example chromatographic techniques and recrystallization techniques, or they are separately prepared from the appropriate isomers of their intermediates.

The compounds of the invention, their methods or preparation and their biological activity will appear more clearly from the examination of the following examples that are presented as an illustration only and are not to be considered as limiting the invention in its scope. Compounds of the invention are identified, for example, by the following analytical methods.

Mass Spectra (MS) are recorded using a Micromass LCT mass spectrometer. The method is positive electrospray ionization, scanning mass m/z from 100 to 1000.

300 MHz $^1$H nuclear magnetic resonance spectra ($^1$H NMR) are recorded at ambient temperature using a Varian Mercury (300 MHz) spectrometer with an ASW 5 mm probe. In the $^1$H NMR chemical shifts (δ) are indicated in parts per million (ppm) with reference to tetramethylsilane (TMS) as the internal standard.

As used in the examples and preparations that follow, as well as the rest of the application, the terms used therein shall have the meanings indicated: "kg" refers to kilograms, "g" refers to grams, "mg" refers to milligrams, "μg" refers to micrograms, "mol" refers to moles, "mmol" refers to millimoles, "M" refers to molar, "mM" refers to millimolar, "μM" refers to micromolar, "nM" refers to nanomolar, "L" refers to liters, "mL" or "ml" refers to milliliters, "μL" refers to microliters, "° C." refers to degrees Celsius, "1 mp" or "m.p." refers to melting point, "bp" or "b.p." refers to boiling point, "mm of Hg" refers to pressure in millimeters of mercury, "cm" refers to centimeters, "nm" refers to nanometers, "abs." refers to absolute, "conc." refers to concentrated, "c" refers to concentration in g/mL, "rt" refers to room temperature, "TLC" refers to thin layer chromatography, "HPLC" refers to high performance liquid chromatography, "i.p." refers to intraperitoneally, "i.v." refers to intravenously, "s"=singlet, "d"=doublet; "t"=triplet; "q"=quartet; "m"=multiplet, "dd"=doublet of doublets; "br"=broad, "LC"=liquid chromatograph, "MS"=mass spectrograph, "ESI/MS"=electrospray ionization/mass spectrograph, "$R_T$"=retention time, "M"=molecular ion, "PSI"=pounds per square inch, "DMSO"=dimethyl sulfoxide, "DMF"=N,N-dimethylformamide, "DCM"=dichloromethane, "HCl"=hydrochloric acid, "SPA"-Scintillatio Proximity Assay, "EtOAc"=ethyl acetate, "PBS"=Phosphate Buffered Saline, "IUPAC"=International Union of Pure and Applied Chemistry, "MHz"=megahertz, "MeOH"=methanol, "N"=normality, "THF"=tetrahydrofuran, "min"=minute(s), "$N_2$"=nitrogen gas, "MeCN" or "$CH_3CN$"=acetonitrile, "$Et_2O$"=ethyl ether, "TFA"=trifluoroacetic acid, "~"=approximately, "rt"=room temperature, "$MgSO_4$"=magnesium sulfate, "$Na_2SO_4$"=sodium sulfate, "$NaHCO_3$"=sodium bicarbonate, "$Na_2CO_3$"=sodium carbonate, "MCPBA"=3-Chloroperoxybenzoic acid, "NMP"=N-methylpyrrolidone, "PS-DCC"=polymer supported-dicyclohexylcarbodiimide, "LiOH"=Lithium hydroxide, "PS-trisamine"=polymer supported-trisamine, "PGH2"=prostaglandin H2, "PGD2"=prostaglandin D2; "PGE2"=prostaglandin E2, "hPGDS"=Hematopoietic PGD2 Synthase, "GSH"=glutathione (reduced), "EIA"=Enzyme immunoassay, "$KH_2PO_4$"=potassium phosphate, monobasic, "$K_2HPO_4$"=potassium phosphate, dibasic, "$FeCl_2$"=ferrous chloride, "MOX"=methoxylamine; "EtOH"=ethanol, "DMSO"=dimethylsulfoxide.

EXAMPLES

Example 1

2-Phenyl-pyrimidine-5-carboxylic acid benzylamide

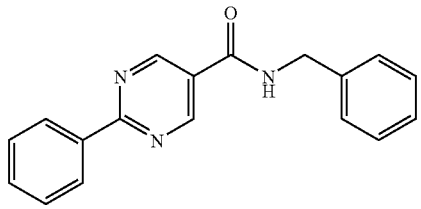

Step 1: A 250 mL, three-neck, round-bottom flask equipped with a magnetic stirrer and a reflux condenser is purged with $N_2$. The flask is charged sequentially with methyl 3,3-diethoxypropionate (5.22 g, 35.3 mmol), anhydrous 1,2-dimethoxyethane (25 mL), anhydrous methyl formate (5 mL), 60% sodium hydride (1.7 g, 42.5 mmol), and the mixture warmed to 40-50° C. until evolution of hydrogen gas stops. The reaction mixture is cooled in an ice/water bath and slowly allowed to reach room temperature overnight with stirring. Anhydrous ether (25 mL) is added, and the resulting suspension is filtered under $N_2$, washed with anhydrous ether (10 mL), and vacuum dried for 2 hours to yield sodium salt of 2-dimethoxymethyl-3-hydroxy-acrylic acid methyl ester (3.51 g, 50%) as a powder. $^1$H NMR ($CD_3OD$): δ 3.33 (s, 6H), 3.60 (s, 3H), 5.31 (s, 1H), 8.89 (s, 1H). (see: P. Zhichkin, D. J. Fairfax, S. A. Eisenbeis, Synthesis, 2002, 720-722.)

Step 2: To a solution of benzamidine hydrochloride hydrate (2 mmol) in anhydrous DMF (4 mL) is added sodium salt of 2-dimethoxymethyl-3-hydroxy-acrylic acid methyl ester (0.46 g, 2.32 mmol) and the reaction mixture heated at 100° C. under N2 for 1 hour. The reaction is cooled to room temperature and water (15 mL) is added. After addition of water, immediate precipitation of the product is observed. The solids are collected by filtration, washed with water (2.5 mL) and vacuum dried to yield 2-phenyl-pyrimidine-5-carboxylic acid methyl ester (0.32 g, 74%). (see: P. Zhichkin, D. J. Fairfax, S. A. Eisenbeis, Synthesis, 2002, 720-722.)

Step 3: A solution of 2-phenyl-pyrimidine-5-carboxylic acid methyl ester (3.15 g) and LiOH (0.71 g) in a mixture of MeOH, THF and water (1:1:1 in volume, 120 mL) is stirred at room temperature overnight. MeOH and THF are evaporated off to give an aqueous solution. The aqueous solution is acidified with 5% hydrochloric acid to adjust pH to between 2.5 and 3. The precipitate is filtered off and washed with water, dried in vacuo to yield 2.94 g (~100%) of 2-phenyl-pyrimidine-5-carboxylic acid as a solid. MS: 201 (M+H).

Step 4: A mixture of 2-phenyl-pyrimidine-5-carboxylic acid, (80 mg), 1-hydroxybenzotriazole (92 mg) and polymer supported-carbodiimide (640 mg, 1.25 mmol/g) in 8 mL of DCM is shaken at room temperature for 30 min and benzylamine (43 mg) is added. After shaking at room temperature for 1.5 days, PS-trisamine (295 mg, 4.08 mmol/g) is added. The mixture is continually shaken at room temperature for 16 hours. The solid is filtered and washed with DCM. The filtrate is concentrated to yield of 2-phenyl-pyrimidine-5-carboxylic acid benzylamide (98 mg, 85%) as a solid. MS: 290 (M+H); $^1$H NMR ($CDCl_3$): 9.17 (s, 2H), 8.50 (d, 2H), 7.52-7.55 (m, 3H), 7.36-7.40 (m, 5H), 6.54 (broad, H), 4.69-4.71 (d, 2H); $IC_{50}$=10 nM.

Example 2

2-Pyridin-4-yl-pyrimidine-5-carboxylic acid phenylamide

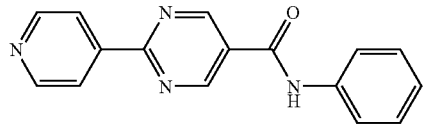

Step 1. To a solution of isonicotinamidine hydrochloride (1 g, 6.35 mmol) in anhydrous DMF (12 mL) is added sodium salt of 2-dimethoxymethyl-3-hydroxy-acrylic acid methyl ester (1.46 g, 7.36 mmol) and the reaction mixture is heated at 100° C. under nitrogen for 1 h. The reaction is cooled to room temperature and water (48 mL) is added. The precipitate is collected by filtration, washed with water and vacuum dried to afford 2-pyridin-4-yl-pyrimidine-5-carboxylic acid methyl ester (1.2 g, 88%). MS: 216 (M+H); $^1$H NMR (300 MHz, $CD_3OD$): δ 4.00 (s, 3H), 8.44 (d, 2H), 8.73 (d, 2H), 9.38 (s, 2H).

Step 2. A solution of 2-pyridin-4-yl-pyrimidine-5-carboxylic acid methyl ester (1.11 g, 5.18 mmol), and aqueous LiOH (1 M, 5.18 mL) in MeOH (7.25 mL) is stirred at room temperature overnight. MeOH is removed in vacuo, and the aqueous solution is treated with 3 N HCl to adjust the pH to between 2 and 3. The solid is filtered off and washed with water and dried in vacuo to yield 2-pyridin-4-yl-pyrimidine-5-carboxylic acid (1 g, 96%) as a solid. MS: 202 (M+H).

Step 3. A mixture of 2-pyridin-4-yl-pyrimidine-5-carboxylic acid (100 mg, 0.5 mmol), 1-hydroxybenzotriazole (76.1 mg, 0.56 mmol) and PS-DCC (539 mg, 1.25 mmol/g, 0.66 mmol) in DMF (8 mL) is shaken at room temperature for 15 min, and aniline (31 mg, 0.33 mmol) is added. After shaking at room temperature for 18 hours, PS-trisamine (398 mg, 3.75 mmol/g, 1.49 mmol) is added and the mixture is continually shaken at room temperature for 18 hours. The solid is filtered and washed with DCM. The filtrate is concentrated to yield 2-pyridin-4-yl-pyrimidine-5-carboxylic acid phenylamide (15 mg, 16%) as solid. MS: 277 (M+H).

Example 3

2-Pyridin-3-yl-pyrimidine-5-carboxylic acid phenylamide

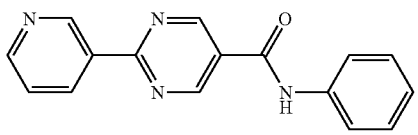

Step 1. To a solution of nicotinamidine hydrochloride (1 g, 6.35 mmol) in anhydrous DMF (12 mL) is added sodium salt of 2-dimethoxymethyl-3-hydroxy-acrylic acid methyl ester (1.46 g, 7.36 mmol) and the reaction mixture is heated at 100° C. under $N_2$ for 3 hours. After this time the reaction is cooled to room temperature and water (48 mL) is added. The precipitate is collected by filtration, washed with water and vacuum dried to afford 2-pyridin-3-yl-pyrimidine-5-carboxylic acid methyl ester (0.7 g, 51%). MS: 216 (M+H).

Step 2. A solution of 2-pyridin-3-yl-pyrimidine-5-carboxylic acid methyl ester (0.73 g, 3.32 mmol) and 1M aqueous LiOH (3.32 mL) in MeOH (5 mL) is stirred at room temperature overnight. The MeOH is removed in vacuo, and the aqueous solution is treated with 3 N HCl to adjust the pH ~2-3. The solid is filtered off and washed with water and dried in vacuum to yield 2-pyridin-3-yl-pyrimidine-5-carboxylic acid (0.2 g, 30%) as a solid. MS: 202 (M+H).

Step 3. A mixture of 2-pyridin-3-yl-pyrimidine-5-carboxylic acid (110 mg, 0.55 mmol) 1-hydroxybenzotriazole (83.5 mg, 0.62 mmol) and PS-DCC (568 mg, 1.28 mmol/g, 0.73 mmol) in DMF (8 mL) is shaken at room temperature for 15 min, and aniline (34 mg, 0.36 mmol) is added. After shaking at room temperature for 18 hours, PS-trisamine (436 mg, 3.75 mmol/g, 1.64 mmol) is added and the mixture is continually shaken at room temperature for 18 hours. The solid is filtered and washed with DCM. The filtrate is concentrated to yield 2-pyridin-3-yl-pyrimidine-5-carboxylic acid phenylamide (41.2 mg, 41%) as a solid. MS: 277 (M+H).

Example 4

2-Pyridin-2-yl-pyrimidine-5-carboxylic acid phenylamide

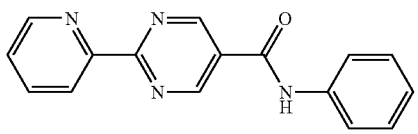

A mixture of 2-pyridin-2-yl-pyrimidine-5-carboxylic acid (100 mg, 0.5 mmol, prepared according to the general procedure described in Example 2, steps 1 and 2), 1-hydroxybenzotriazole (76.1 mg, 0.56 mmol) and PS-DCC (518 mg, 1.28 mmol/g, 0.66 mmol) in 8 mL of DMF is shaken at room temperature for 15 minutes, and aniline (31 mg, 0.33 mmol) is added. After shaking at room temperature for 18 hours, PS-trisamine (400 mg, 3.75 mmol/g, 1.5 mmol) is added and the mixture is continually shaken at room temperature for 18 hours. The solid is filtered and washed with DCM. The filtrate is concentrated to yield 2-pyridin-2-yl-pyrimidine-5-carboxylic acid phenylamide (21 mg, 23%) as a solid. MS: 277 (M+H).

Example 5

2-(3-Fluoro-phenyl)-pyrimidine-5-carboxylic acid phenylamide

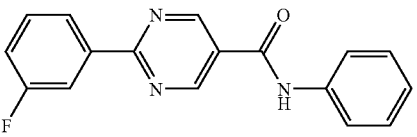

A mixture of 2-(3-fluoro-phenyl)-pyrimidine-5-carboxylic acid (107 mg, 0.49 mmol, prepared according to the general procedure described in Example 2, steps 1 and 2), 1-hydroxybenzotriazole (75 mg, 0.56 mmol) and PS-DCC (511 mg, 1.28 mmol/g, 0.65 mmol) in DMF (8 mL) is shaken at room temperature for 15 min. Aniline (30.4 mg, 0.33 mmol) is added. The mixture is shaken at room temperature for 18 hours. PS-trisamine (392 mg, 3.75 mmol/g, 1.47 mmol) is added and the mixture is continually shaken at room temperature for 18 hours. The solid is filtered and washed with EtOAc. The filtrate is concentrated to afford 2-(3-fluoro-phenyl)-pyrimidine-5-carboxylic acid phenylamide as a solid in quantitative yield. MS: 294 (M+H).

Example 6

2-(4-Fluoro-phenyl)-pyrimidine-5-carboxylic acid phenylamide

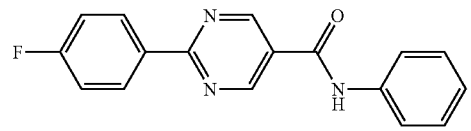

A mixture of 2-(4-fluoro-phenyl)-pyrimidine-5-carboxylic acid (107 mg, 0.49 mmol, prepared according to the general procedure described in Example 2, steps 1 and 2), 1-hydroxybenzotriazole (75 mg, 0.56 mmol) and PS-DCC (511 mg, 1.28 mmol/g, 0.65 mmol) in DMF (8 mL) is shaken at room temperature for 15 min. Aniline (30.4 mg, 0.33 mmol) is added. The mixture is shaken at room temperature for 18 hours. PS-trisamine (392 mg, 3.75 mmol/g, 1.47 mmol) is added and the mixture is continually shaken at room temperature for 18 hours. The solid is filtered and washed with EtOAc. The filtrate is concentrated to afford 2-(4-fluoro-phenyl)-pyrimidine-5-carboxylic acid phenylamide (83.4 mg, 86%) as a solid. MS: 294 (M+H).

Example 7

2-(2-Fluoro-phenyl)-pyrimidine-5-carboxylic acid phenylamide

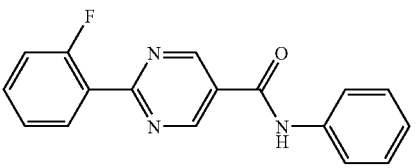

A mixture of 2-(2-fluoro-phenyl)-pyrimidine-5-carboxylic acid (105 mg, 0.48 mmol, prepared according to the general procedure described in Example 2, steps 1 and 2), 1-hydroxybenzotriazole (74 mg, 0.54 mmol) and PS-DCC (501 mg, 1.28 mmol/g, 0.64 mmol) in DMF (8 mL) is shaken at room temperature for 15 min. Aniline (29.9 mg, 0.32 mmol) is added. The mixture is shaken at room temperature for 18 hours. PS-trisamine (385 mg, 3.75 mmol/g, 1.44 mmol) is added and the mixture is continually shaken at room temperature for 18 hours. The solid is filtered and washed with EtOAc. The filtrate is concentrated to afford 2-(2-fluoro-phenyl)-pyrimidine-5-carboxylic acid phenylamide (60 mg, 63%) as a solid. MS: 294 (M+H).

Example 8

2-Phenyl-pyrimidine-5-carboxylic acid (2,2-dioxo-2,3-dihydro-1H-2lamda*6*-benzo[c]isothiazol-5-yl)-amide

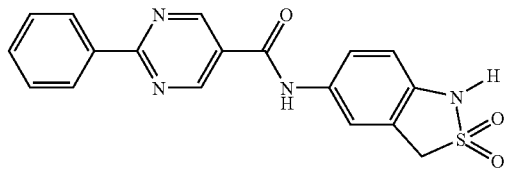

A mixture of 2-phenyl-pyrimidine-5-carboxylic acid (60 mg, 0.3 mmol), 1-hydroxybenzotriazole (69 mg, 0.51 mmol), and PS-DCC (469 mg, 1.21 mmol/g, 0.6 mmol in DMF (8 mL) is shaken at room temperature for 60 min. 2,2-Dioxo-2,3-dihydro-1H-2lamda*6*-benzo[c]isothiazol-5-ylamine (55 mg, 0.3 mmol) is added. The mixture is shaken at room temperature for 2 days. PS-trisamine (221 mg, 4.08 mmol/g, 0.9 mmol) is added and the mixture is continually shaken at room temperature for 18 hours. The solid is filtered and washed with MeOH. The filtrate is concentrated to yield 2-phenyl-pyrimidine-5-carboxylic acid (2,2-dioxo-2,3-dihydro-1H-2lamda*6*-benzo[c]isothiazol-5-yl)-amide (57 mg) as a solid. MS: 367 (M+H); $^1$H NMR (300 MHz, CD$_3$OD): δ 4.58 (s, 2H), 6.86 (d, H), 7.53-7.65 (m, 4H), 7.76 (s, H), 8.46 (t, 2H), 9.33 (d, 2H), 10.41 (broad, H), 10.54 (s, H); IC$_{50}$=2.5 nM.

Example 9

2-Phenyl-pyrimidine-5-carboxylic acid [1-(1H-imidazol-2-ylmethyl-piperidin-4-yl]-amide

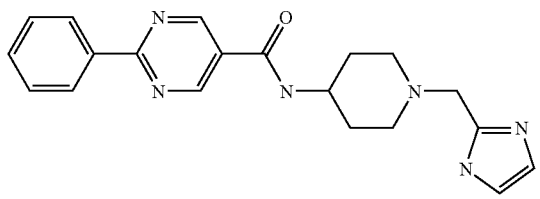

Following procedures similar to those of Example 8 but substituting 1-(1H-imidazol-2-ylmethyl)-piperidin-4-ylamine for 2,2-dioxo-2,3-dihydro-1H-2lamda*6*-benzo[c]isothiazol-5-ylamine, there is prepared 2-phenyl-pyrimidine-5-carboxylic acid [1-(1H-imidazol-2-ylmethyl-piperidin-4-yl]-amide (74 mg) as a solid. MS: 363 (M+H); $^1$H NMR (300 MHz, DMSO-d$_6$): δ 1.80-1.89 (m, 2H), 2.05-2.16 (m, 2H), 3.21-3.37 (m, 2H), 3.50-3.60 (m, 2H), 4.14 (m, H), 4.66 (s, 2H), 7.49-7.58 (m, 3H), 7.80 (s, 2H), 8.44 (m, 2H), 8.69 (d, H), 9.23 (s, 2H); IC$_{50}$=2 nM.

Example 10

2-Phenyl-pyrimidine-5-carboxylic acid (6-dimethylamino-pyridin-3-ylmethyl)-amide

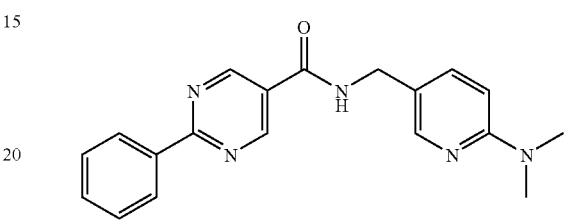

Following procedures similar to those of Example 8 but substituting 6-dimethylamino-pyridin-3-ylmethylamine (0.3 mmol) for 2,2-dioxo-2,3-dihydro-1H-2lamda*6*-benzo[c]isothiazol-5-ylamine, there is prepared 2-phenyl-pyrimidine-5-carboxylic acid (6-dimethylamino-pyridin-3-ylmethyl)-amide as a solid. MS: 334 (M+H).

Example 11

2-Phenyl-pyrimidine-5-carboxylic acid [2-(2-pyrrolidin-1-yl-ethyl)-benzooxazol-6-yl]-amide

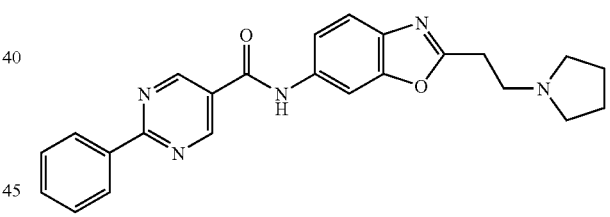

Step 1: A solution of 2-methyl-6-nitro-benzoxazole (30 mmol), dimethyl formamide dimethyl acetal (60 mmol) and pyrrolidine (60 mmol) in DMF (45 mL) is stirred at 100° C. for 16 hours. The reaction mixture is concentrated in vacuo. The residue is dissolved in EtOAc, washed with water and brine, dried (Na$_2$SO$_4$) and filtered. The filtrate is concentrated. The residue is washed with cooled EtOAc to afford 6-nitro-2-(2-pyrrolidin-1-yl-vinyl)-benzooxazole as a solid. $^1$H NMR (300 MHz, CDCl$_3$): δ 1.80-2.25 (broad, 4H), 3.10-3.80 (broad, 4H), 5.06 (d, H), 7.44 (d, H), 7.96 (d, H), 8.21 (m, 2H).

Step 2: A solution of 6-nitro-2-(2-pyrrolidin-1-yl-vinyl)-benzooxazole (8.5 mmol) and palladium/carbon (10%) (0.85 mmol) in ethanol (100 mL) is hydrogenated with the pressure of 50 psi at room temperature for 18 hours. The mixture is filtered and the filtrate is concentrated in vacuo to afford 2-(2-pyrrolidin-1-yl-vinyl)-benzooxazol-6-ylamine as a solid. $^1$H NMR (300 MHz, CDCl$_3$): δ 1.82 (m, 4H), 3.2 (broad, 4H), 3.65 (broad, 2H), 4.92 (d, H), 6.49 (d, H), 6.64 (d, H), 7.19 (d, H), 7.60 (d, H).

Step 3: To a solution of 2-(2-pyrrolidin-1-yl-vinyl)-benzooxazol-6-ylamine (3.2 mmol) in MeOH (40 mL) is added sodium cyanoborohydride (6.4 mmol) at room temperature. The reaction mixture is heated to reflux for 18 hours. The mixture is concentrated and the residue is dissolved in DCM. The solution is washed with water and brine, and dried (MgSO$_4$). A small amount of activated carbon is added to the solution, and the mixture is filtered. The filtrate is concentrated to afford 2-(2-pyrrolidin-1-yl-ethyl)-benzooxazol-6-ylamine as a solid. $^1$H NMR (300 MHz, CDCl$_3$): δ 1.79 (m, 4H), 2.61 (m, 4H), 3.00-3.18 (m, 4H), 4.78 (broad, 2N—H), 6.68 (q, H), 6.80 (d, H), 7.43 (d, H).

Step 4: Following procedures similar to those of Example 8, but substituting 2-(2-pyrrolidin-1-yl-ethyl)-benzooxazol-6-ylamine (0.3 mmol) for 2,2-dioxo-2,3-dihydro-1H-2lamda*6*-benzo[c]isothiazol-5-ylamine, there is prepared 2-phenyl-pyrimidine-5-carboxylic acid [2-(2-pyrrolidin-1-yl-ethyl)-benzooxazol-6-yl]-amide as a solid. MS: 414 (M+H); $^1$H NMR (300 MHz, DMSO-d$_6$): δ 1.70 (broad, 4H), 2.44-2.78 (m, 2H), 2.95-3.30 (m, 6H), 7.55-7.75 (m, 5H), 8.27 (s, H), 8.5 (q, 2H), 8.38 (s, 2H), 10.8 (s, H); IC$_{50}$=18 nM.

Example 12

2-Phenyl-pyrimidine-5-carboxylic acid 4-sulfamoyl-benzylamide

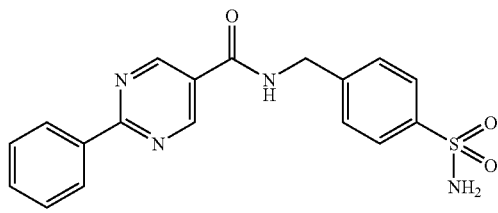

Following procedures similar to those of Example 8 but substituting 4-aminomethyl-benzenesulfonamide (0.3 mmol) for 2,2-dioxo-2,3-dihydro-1H-2lamda*6*-benzo[c]isothiazol-5-ylamine, there is prepared 2-phenyl-pyrimidine-5-carboxylic acid 4-sulfamoyl-benzylamide as a solid. MS: 369 (M+H); $^1$H NMR (300 MHz, DMSO-d$_6$): δ 4.60 (d, 2H), 7.34 (s, 2H), 7.54-7.64 (m, 5H), 7.78 (d, 2H), 8.45 (m, 2H), 9.30 (s, 2H), 9.46 (t, H).

Example 13

2-Phenyl-pyrimidine-5-carboxylic acid [2-(4-sulfamoyl-phenyl)-ethyl]-amide

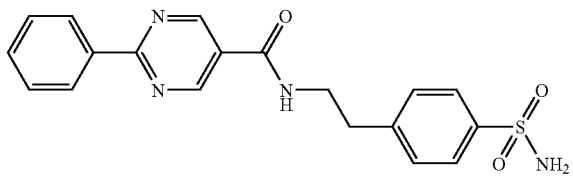

Following procedures similar to those of Example 8 but substituting 4-(2-amino-ethyl)-benzenesulfonamide (0.3 mmol) for 2,2-dioxo-2,3-dihydro-1H-2lamda*6*-benzo[c]isothiazol-5-ylamine, there is prepared 2-phenyl-pyrimidine-5-carboxylic acid [2-(4-sulfamoyl-phenyl-ethyl]-amide as a solid. MS: 383 (M+H).

Example 14

(R)-2-Phenyl-pyrimidine-5-carboxylic acid [4-(2-oxo-oxazolidin-4-ylmethyl)-phenyl]-amide

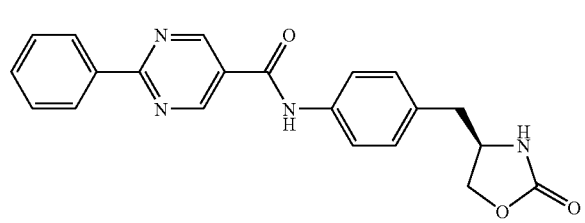

Following procedures similar to those of Example 8 but substituting 4-(4-amino-benzyl)-oxazolidin-2-one (0.3 mmol) for 2,2-dioxo-2,3-dihydro-1H-2lamda*6*-benzo[c]isothiazol-5-ylamine, there is prepared (R)-2-phenyl-pyrimidine-5-carboxylic acid [4-(2-oxo-oxazolidin-4-ylmethyl)-phenyl]-amide as a solid. MS: 375 (M+H); $^1$H NMR (300 MHz, CD$_3$OD): δ 2.85-2.94 (m, 2H), 4.13-4.24 (m, 2H), 4.36 (m, H), 7.30 (d, 2H), 7.46-7.60 (m, 3H), 7.70 (d, 2H), 8.44-8.56 (m, 2H), 9.23 (d, 2H).

Example 15

2-Phenyl-pyrimidine-5-carboxylic acid (6-acetylamino-pyridin-3-yl)-amid

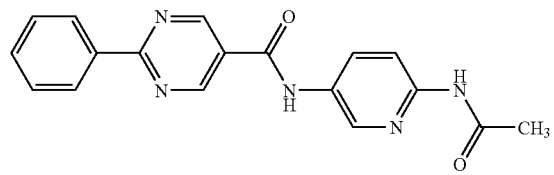

Following procedures similar to those of Example 8 but substituting N-(5-amino-pyridin-2-yl)-acetamide (0.3 mmol) for 2,2-dioxo-2,3-dihydro-1H-2lamda*6*-benzo[c]isothiazol-5-ylamine, there is prepared 2-phenyl-pyrimidine-5-carboxylic acid (6-acetylamino-pyridin-3-yl)-amide as a solid. MS: 334 (M+H); $^1$H NMR (300 MHz, DMSO-d$_6$): δ 2.09 (s, 3H), 7.47-7.66 (m, 3H), 8.09 (s, 2H), 8.40-8.53 (m, 2H), 8.72 (s, H), 9.36 (s, 2H), 10.29 (s N—H), 10.70 (s, N—H).

Example 16

2-Phenyl-pyrimidine-5-carboxylic acid (3-carbamoyl-phenyl)-amide

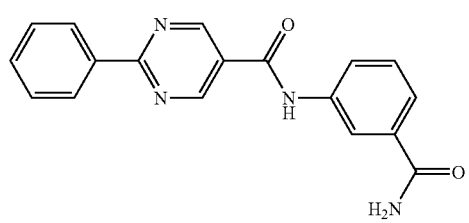

Following procedures similar to those of Example 8 but substituting 3-amino-benzamide (0.3 mmol) for 2,2-dioxo-2,3-dihydro-1H-2lamda*6*-benzo[c]isothiazol-5-ylamine, there is prepared 2-phenyl-pyrimidine-5-carboxylic acid (3-carbamoyl-phenyl)-amide as a solid. MS: 319 (M+H).

Example 17

2-Phenyl-pyrimidine-5-carboxylic acid (3-methylcarbamoyl-phenyl)-amide

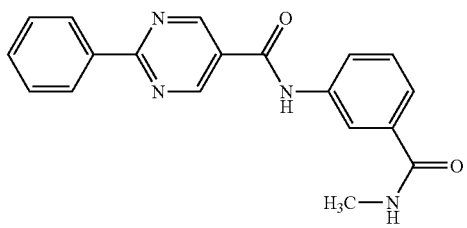

Following procedures similar to those of Example 8 but substituting 3-amino-N-methyl-benzamide (0.3 mmol) for 2,2-dioxo-2,3-dihydro-1H-2lamda*6*-benzo[c]isothiazol-5-ylamine, there is prepared 2-phenyl-pyrimidine-5-carboxylic acid (3-methylcarbamoyl-phenyl)-amide as a solid. MS: 333 (M+H); $^1$H NMR (300 MHz, DMSO-d$_6$): δ 2.79 (d, 3H), 7.47 (t, H), 7.54-7.65 (m, 3H), 7.96 (d, 2H), 8.23 (s, H), 8.37-8.54 (m, 3H), 9.37 (s, 2H), 10.70 (s, 1H).

Example 18

2-Phenyl-pyrimidine-5-carboxylic acid (4-hydroxy-cyclohexyl)-amide

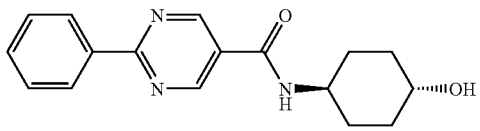

Following procedures similar to those of Example 8 but substituting 4-amino-cyclohexanol (0.3 mmol) for 2,2-dioxo-2,3-dihydro-1H-2lamda*6*-benzo[c]isothiazol-5-ylamine, there is prepared 2-phenyl-pyrimidine-5-carboxylic acid (4-hydroxy-cyclohexyl)-amide as a solid. MS: 298 (M+H).

Example 19

4-methyl-2-[(2-phenyl-pyrimidin-5-carbonyl)-amino]-thiazole-5-carboxylic acid ethyl ester

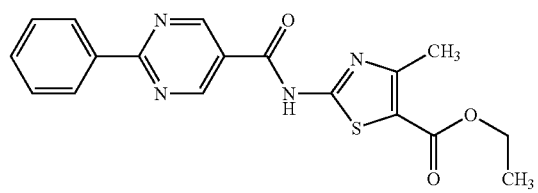

Following procedures similar to those of Example 8 but substituting 2-amino-4-methyl-thiazole-5-carboxylic acid ethyl ester (0.3 mmol) for 2,2-dioxo-2,3-dihydro-1H-2lamda*6*-benzo[c]isothiazol-5-ylamine, there is prepared 4-methyl-2-[(2-phenyl-pyrimidin-5-carbonyl)-amino]-thiazole-5-carboxylia acid ethyl ester as a solid. MS: 369 (M+H).

Example 20

{2-[(2-Phenyl-pyrimidine-5-carbonyl)-amino]-thiazol-4-yl}-acetic acid ethyl ester

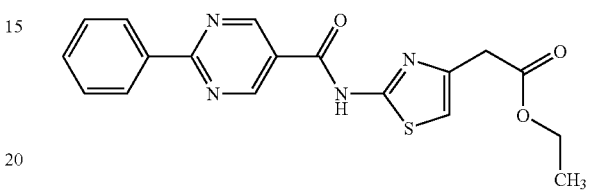

Following procedures similar to those of Example 8 but substituting (2-amino-thiazol-4-yl)-acetic acid ethyl ester (0.3 mmol) for 2,2-dioxo-2,3-dihydro-1H-2lamda*6*-benzo[c]isothiazol-5-ylamine, there is prepared {2-[(2-phenyl-pyrimidine-5-carbonyl)-amino]-thiazol-4-yl}-acetic acid ethyl ester as a solid. MS: 369 (M+H).

Example 21

4-Methyl-2-[(2-phenyl-pyrimidin-5-carbonyl)-amino]-thiazole-5-carboxylic acid

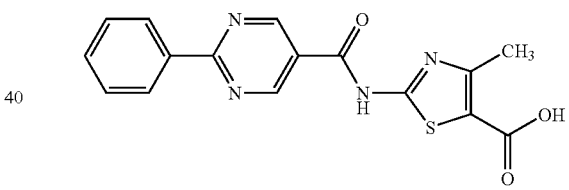

A mixture of 4-methyl-2-[(2-phenyl-pyrimidin-5-carbonyl)-amino]-thiazole-5-carboxylic acid ethyl ester (0.15 mmol) and 10% aqueous NaOH solution (4 mL) in THF (10 mL) is stirred at 60° C. for 18 hours. THF is evaporated and the residue is acidified with 5% hydrochloric acid to pH ~2.0-2.5. The precipitate is filtered and dried to afford 4-methyl-2-[(2-phenyl-pyrimidin-5-carbonyl)-amino]-thiazole-5-carboxylic acid as a solid. MS: 341 (M+H).

Example 22

{2-[(2-phenyl-pyrimidine-5-carbonyl)-amino]-thiazol-4-yl}-acetic acid

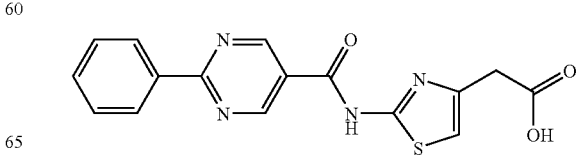

Following procedures similar to those of Example 21 but substituting {2-[(2-phenyl-pyrimidine-5-carbonyl)-amino]-thiazol-4-yl}-acetic acid ethyl ester for 4-methyl-2-[(2-phenyl-pyrimidin-5-carbonyl)-amino]-thiazole-5-carboxylic acid ethyl ester, there is prepared {2-[(2-phenyl-pyrimidine-5-carbonyl)-amino]-thiazol-4-yl}-acetic acid as a solid. MS: 341 (M+H).

Example 23

2-Phenyl-pyrimidine-5-carboxylic acid 4-methylsulfamoyl-benzylamide

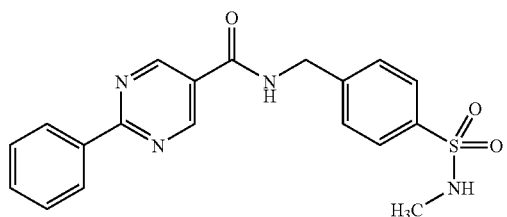

Following procedures similar to those of Example 8 but substituting 3-aminomethyl-N-methyl-benzenesulfonamide hydrochloride (1.5 mmol) for 2,2-dioxo-2,3-dihydro-1H-2lamda*6*-benzo[c]isothiazol-5-ylamine there is prepared 2-phenyl-pyrimidine-5-carboxylic acid 4-methylsulfamoyl-benzylamide as a solid. MS: 383 (M+H); $^1$H NMR (300 MHz, CD$^3$OD): δ 3.36 (s, 3H), 4.51 (s, 2H), 7.48-7.57 (m, 3H), 7.59 (d, 2H), 7.84 (d, 2H), 8.50 (m, 2H), 9.25 (s, 2H).

Example 24

2-Phenyl-pyrimidine-5-carboxylic acid 4-dimethylsulfamoyl-benzylamide

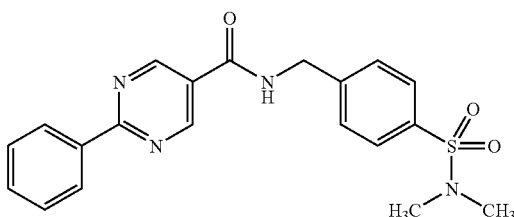

A mixture of 2-phenyl-pyrimidine-5-carboxylic acid sulfamoyl-benzylamide (Example 12, 0.3 mmol), iodomethane (0.3 mmol) and potassium carbonate (0.9 mmol) in DMF (8 mL) is stirred at room temperature for 18 hours. The mixture is concentrated in vacuo and the residue is dissolved in EtOAc (30 mL). The resulting solution is washed with water, brine, dried (Na$_2$SO$_4$), filtered and concentrated. The residue is purified by column chromatography eluting with 5-10% EtOAc in DCM to afford 2-phenyl-pyrimidine-5-carboxylic acid 4-dimethylsulfamoyl-benzylamide as a solid. MS: 397 (M+H); $^1$H NMR (300 MHz, CD$_3$OD): δ 2.70 (s, 6H), 4.74 (s, 2H), 7.46-7.57 (m, 3H), 7.65 (d, 2H), 7.77 (d, 2H), 8.43-8.56 (m, 2H), 9.25 (s, 2H).

Example 25

2-Phenyl-pyrimidine-5-carboxylic acid (3,5-difluoro-phenyl)-amide

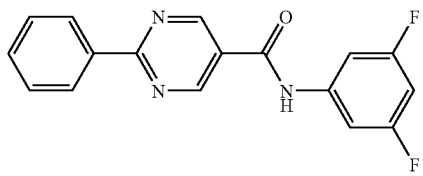

Following procedures similar to those of Example 8 but substituting 3,5-difluoroaniline (0.3 mmol) for 2,2-dioxo-2,3-dihydro-1H-2lamda*6*-benzo[c]isothiazol-5-ylamine, there is prepared 2-phenyl-pyrimidine-5-carboxylic acid (3,5-difluoro-phenyl)-amide as a solid. MS: 312 (M+H).

Example 26

2-Phenyl-pyrimidine-5-carboxylic acid pyridin-2-ylamide

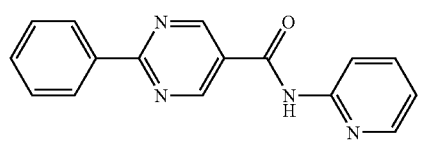

Following procedures similar to those of Example 8 but substituting 2-aminopyridine (0.3 mmol) for 2,2-dioxo-2,3-dihydro-1H-2lamda*6*-benzo[c]isothiazol-5-ylamine, there is prepared 2-phenyl-pyrimidine-5-carboxylic acid pyridin-2-ylamide as a solid. MS: 277 (M+H).

Example 27

2-Phenyl-pyrimidine-5-carboxylic acid thiazol-2-ylamide

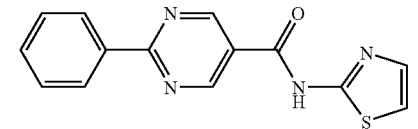

Following procedures similar to those of Example 8 but substituting 2-aminothiazole (0.3 mmol) for 2,2-dioxo-2,3-dihydro-1H-2lamda*6*-benzo[c]isothiazol-5-ylamine, there is prepared 2-phenyl-pyrimidine-5-carboxylic acid thiazol-2-ylamide as a solid. MS: 283 (M+H).

Example 28

2-Phenyl-pyrimidine-5-carboxylic acid (3-sulfamoyl-phenyl)-amide

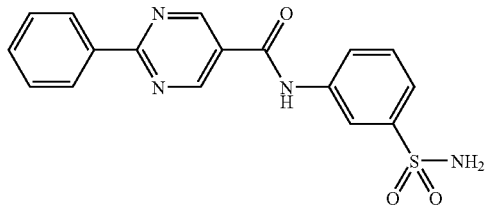

Following procedures similar to those of Example 8 but substituting 3-amino-benzenesulfonamide (0.3 mmol) for 2,2-dioxo-2,3-dihydro-1H-2lamda*6*-benzo[c]isothiazol-5-ylamine, there is prepared 2-phenyl-pyrimidine-5-carboxylic acid (3-sulfamoyl-phenyl-amide as a solid. MS: 355 (M+H).

Example 29

2-Phenyl-pyrimidine-5-carboxylic acid (2-oxo-1,2-dihydro-pyrimidin-4-yl)-amide

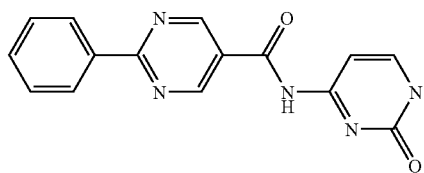

Following procedures similar to those of Example 8 but substituting 4-amino-1H-pyrimidin-2-one (0.3 mmol) for 2,2-dioxo-2,3-dihydro-1H-2lamda*6*-benzo[c]isothiazol-5-ylamine, there is prepared 2-phenyl-pyrimidine-5-carboxylic acid (2-oxo-1,2-dihydropyrimidine-4-yl)-amide as a solid. MS: 294 (M+H); $^1$H NMR (300 MHz, DMSO-d$_6$): δ 7.17 (bs, N—H), 7.47-7.68 (m, 4H), 7.90 (d, H), 8.46 (d, 2H), 9.35 (s, 2H), 11.65 (bs, N—H); IC$_{50}$=15 nM.

Example 30

2-Phenyl-pyrimidine-5-carboxylic acid (4-sulfamoyl-phenyl)-amide

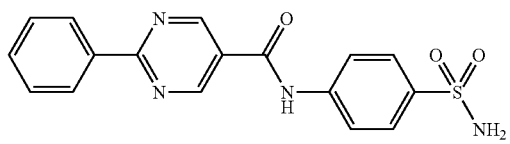

Following procedures similar to those of Example 8 but substituting 4-amino-benzenesulfonamide (0.3 mmol) for 2,2-dioxo-2,3-dihydro-1H-2lamda*6*-benzo[c]isothiazol-5-ylamine, there is prepared 2-phenyl-pyrimidine-5-carboxylic acid (4-sulfamoyl-phenyl-amide as a solid. MS: 355 (M+H). IC$_{50}$=5 nM.

Example 31

2-Phenyl-pyrimidine-5-carboxylic acid pyrimidin-4-ylamide

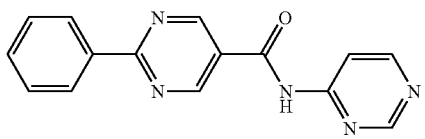

Following procedures similar to those of Example 8 but substituting 4-aminopyrimidine (0.3 mmol) for 2,2-dioxo-2,3-dihydro-1H-2lamda*6*-benzo[c]isothiazol-5-ylamine, there is prepared 2-phenyl-pyrimidine-5-carboxylic acid pyrimidin-4-ylamide as a solid. MS: 278 (M+H);

Example 32

2-Phenyl-pyrimidine-5-carboxylic acid (1-pyridin-3-ylmethyl-piperidin-4-yl)-amide

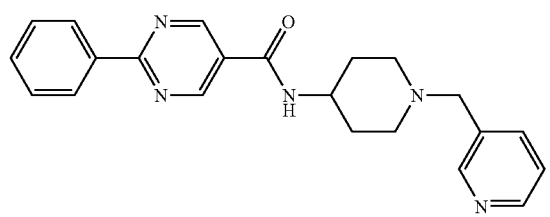

Following procedures similar to those of Example 8 but substituting 1-pyridin-3-ylmethyl-piperidin-4-ylamine (0.3 mmol) for 2,2-dioxo-2,3-dihydro-1H-2lamda*6*-benzo[c]isothiazol-5-ylamine, there is prepared 2-phenyl-pyrimidine-5-carboxylic acid (1-pyridin-3-ylmethyl-piperidin-4-yl)-amide as a solid. MS: 374 (M+H).

Example 33

2-Phenyl-pyrimidine-5-carboxylic acid [2-(2-oxo-imidazolidin-1-yl)-ethyl]-amide

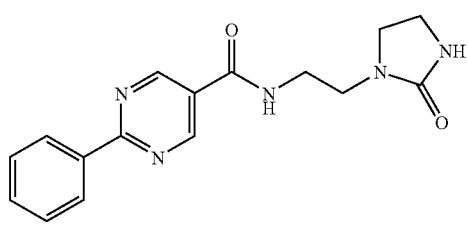

Following procedures similar to those of Example 8 but substituting 1-(2-amino-ethyl)-imidazolidin-2-one (0.3 mmol) for 2,2-dioxo-2,3-dihydro-1H-2lamda*6*-benzo[c]isothiazol-5-ylamine, there is prepared 2-phenyl-pyrimidine- 5-carboxylic acid [2-(2-oxo-imidazolidin-1-yl)-ethyl]-amide as a solid. MS: 312 (M+H); $^1$H NMR (300 MHz, CDCl$_3$): δ 3.47-3.58 (m, 4H), 4.60-4.73 (m, 4H), 4.52 (s, N—H), 7.46-7.57 (m, 3H), 8.02 (bs, N—H), 8.53 (m, 2H), 9.24 (s, 2H); IC$_{50}$=32 nM.

Example 34

2-Phenyl-pyrimidine-5-carboxylic acid [2-(1H-imidazol-4-yl)-ethyl]-amide

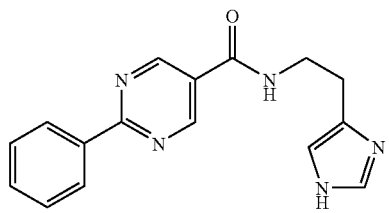

Following procedures similar to those of Example 8 but substituting 2-(1H-imidazol-4-yl)-ethylamine (0.3 mmol) for 2,2-dioxo-2,3-dihydro-1H-2lamda*6*-benzo[c]isothiazol-5-ylamine, there is prepared 2-phenyl-pyrimidine-5-carboxylic acid [2-(1H-imidazol-4-yl)-ethyl]-amide as a solid; MS: 294 (M+H); IC$_{50}$=35 nM.

Example 35

2-Phenyl-pyrimidine-5-carboxylic acid (tetrahydro-pyran-4-ylmethyl)-amide

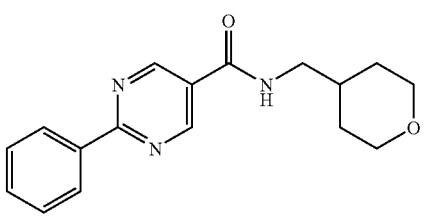

Following procedures similar to those of Example 8 but substituting (tetrahydro-pyran-4-yl)-methylamine (0.3 mmol) for 2,2-dioxo-2,3-dihydro-1H-2lamda*6*-benzo[c]isothiazol-5-ylamine, there is prepared 2-phenyl-pyrimidine-5-carboxylic acid (tetrahydro-pyran-4-ylmethyl)-amide as a solid. MS: 298 (M+H).

Example 36

2-Phenyl-pyrimidine-5-carboxylic acid (3-trifluoromethyl-phenyl)-amide

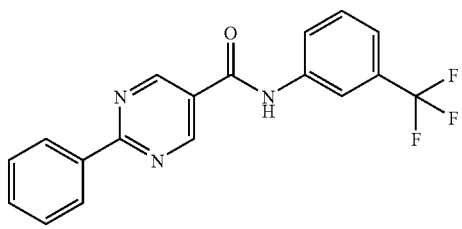

Following procedures similar to those of Example 8 but substituting 3-trifluoromethyl-aniline (0.3 mmol) for 2,2-dioxo-2,3-dihydro-1H-2lamda*6*-benzo[c]isothiazol-5-ylamine, there is prepared 2-phenyl-pyrimidine-5-carboxylic acid (3-trifluoromethyl-phenyl)-amide as a solid. MS: 344 (M+H).

Example 37

2-Phenyl-pyrimidine-5-carboxylic acid (2H-pyrazol-3-yl)-amide

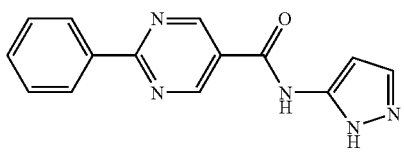

Following procedures similar to those of Example 8 but substituting 2H-pyrazol-3-ylamine (0.3 mmol) for 2,2-dioxo-2,3-dihydro-1H-2lamda*6*-benzo[c]isothiazol-5-ylamine, there is prepared 2-phenyl-pyrimidine-5-carboxylic acid (2H-pyrazol-3-yl)-amide as a solid. MS: 266 (M+H).

Example 38

2-Phenyl-pyrimidine-5-carboxylic acid (1-methyl-piperidin-4-yl)-amide

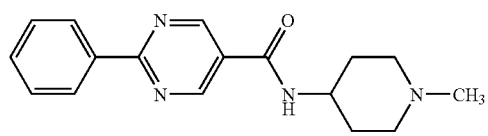

Following procedures similar to those of Example 8 but substituting 1-methyl-piperidin-4-ylamine (0.3 mmol) for 2,2-dioxo-2,3-dihydro-1H-2lamda*6*-benzo[c]isothiazol-5-ylamine, there is prepared 2-phenyl-pyrimidine-5-carboxylic acid (1-methyl-piperidin-4-yl)-amide as a solid. MS: 297 (M+H); IC$_{50}$=96 nM.

Example 39

2-Phenyl-pyrimidine-5-carboxylic acid pyrimidin-2-ylamide

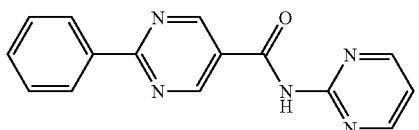

Following procedures similar to those of Example 8 but substituting 2-aminopyrimidine (0.3 mmol) for 2,2-dioxo-2,3-dihydro-1H-2lamda*6*-benzo[c]isothiazol-5-ylamine, there is prepared 2-phenyl-pyrimidine-5-carboxylic acid pyrimidin-2-ylamide as a solid. MS: 278 (M+H).

Example 40

2-(3,5-Difluoro-phenyl)-pyrimidine-5-carboxylic acid 3-methylsulfamoyl-benzylamide

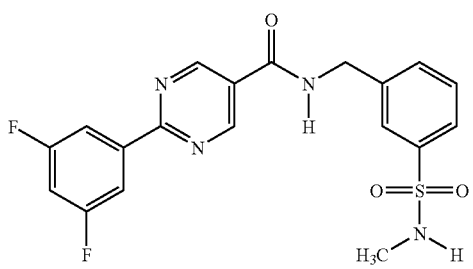

A mixture of 2-(3,5-difluoro-phenyl)-pyrimidine-5-carboxylic acid (118 mg, 0.5 mmol, prepared according to the general procedure described in Example 2, steps 1 and 2) and O-(7-azabenzotriazol-1-yl)-N,N,N,N-tetramethyluronium hexafluorophosphate (190 mg, 0.5 mmol) in dry DMF (5 mL) is treated with diisopropylethylamine (0.09 mL) and stirred at room temperature for 30 min. A solution of 3-methylsulfamoylbenzylamine (150 mg, 0.75 mmol.) in dry DMF (1 mL) is added and the mixture stirred at room temperature for 24 hours. The solvent is removed and the residue is partitioned between EtOAc and water. The organic phase is separated and washed with saturated NaHCO$_3$, water and brine, dried (MgSO$_4$), filtered and concentrated in vacuo. The residue is purified by column chromatography eluting with 30% EtOAc in DCM to afford 2-(3,5-difluorophenyl)-pyrimidine-5-carboxylic acid 3-methylsulfamoyl-benzylamide (125 mg, 62%) as a solid. MS: 419 (M+H); $^1$H NMR (300 MHz, DMSO-d$_6$): δ 2.41 (d, 3H), 4.64 (d, 2H), 7.43-7.75 (m, 5H), 7.80 (s, 1H), 8.05 (d, 2H), 9.37 (s, 2H), 9.60 (t, 1H); IC$_{50}$=49 nM.

Example 41

2-(2,5-Difluoro-phenyl)-pyrimidine-5-carboxylic acid 3-methylsulfamoyl-benzylamide

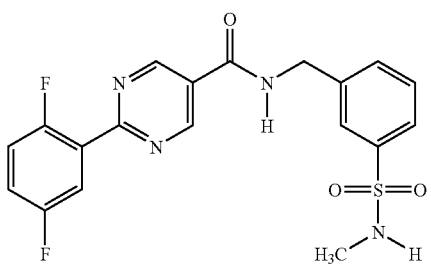

A mixture of 2-(2,5-difluoro-phenyl)-pyrimidine-5-carboxylic acid (118 mg, 0.5 mmol, prepared according to the general procedure described in Example 2, steps 1 and 2), and 0-(7-azabenzotriazol-1-yl)-N,N,N,N-tetramethyluronium hexafluorophosphate (190 mg, 0.5 mmol) in dry DMF (5 mL) is treated with 0.09 mL of diisopropylethylamine and stirred at room temperature for 30 minutes. A solution of 3-methylsulfamoylbenzylamine (150 mg, 0.75 mmol) in dry DMF (1 mL) is added and the mixture stirred at room temperature for 24 hours. The solvent is removed and the residue partitioned between EtOAc and saturated NaHCO$_3$. The organic phase is separated and washed with water and brine, dried (MgSO$_4$), filtered and concentrated in vacuo. The residue is purified by column chromatography eluting with 20% EtOAc in DCM to afford 2-(2,5-difluoro-phenyl)-pyrimidine-5-carboxylic acid 3-methylsulfamoyl-benzylamide (135 mg, 65%) as a solid. MS: 419 (M+H); $^1$H NMR (300 MHz, DMSO-d$_6$): δ 2.41 (d, 3H), 4.64 (d, 2H), 7.43-7.78 (m, 5H), 7.89 (s, 1H) 7.90 (t, 1H), 9.37 (s, 2H), 9.60 (t, 1H).

Example 42

2-(4-Difluorophenyl)-4-methylpyrimidine-5-carboxylic acid-3-methylsulfamoyl-benzylamide

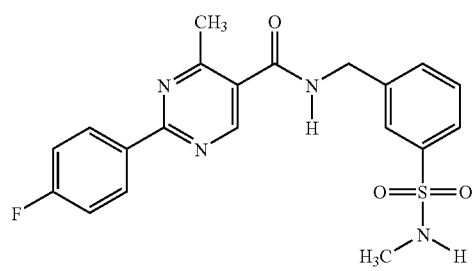

Step 1: 4-Fluorobenzamidine hydrochloride (1.25 g, 7.16 mmol) is added to a solution of sodium metal (0.17 g, 7.39 mmol) in dry ethanol (25 mL) and stirred at room temperature for 20 min. Ethyl-2-acetyl-3-(dimethylamino)acrylate (1.35 g, 7.16 mmol) is added. The mixture is heated to reflux for 3 hours. The solvent is removed in vacuo. The residue is dissolved in EtOAc, washed with water and brine, dried (MgSO$_4$), filtered and concentrated in vacuo to afford ethyl-2-(4-fluorophenyl)-4-methyl-pyrimidine-5-carboxylate (1.65 g, 87%) as a solid. MS: 261 (M+H) 261.

Step 2: A solution of ethyl-2-(4-fluorophenyl)-4-methylpyrimidine-5-carboxylate (1.65 g, 6.35 mmol) in MeOH (75 mL) is treated with 2 N aqueous sodium hydroxide (10 mL) and heated to reflux for 30 min. MeOH is removed in vacuo and the residue is diluted with water (50 mL). The solution is adjusted to pH ~2 with 2 M hydrochloric acid. The precipitated is collected by filtration, washed with water and vacuum dried to afford 2-(4-fluorophenyl)-4-methylpyrimidine-5-carboxylic acid (1.3 g, 88%) as a solid. MS: 233 (M+H).

Step 3: A mixture of 2-(4-fluorophenyl)-4-methylpyrimidine-5-carboxylic acid (232 mg, 1 mmol) and O-(7-azabenzotriazol-1-yl)-N,N,N,N-tetramethyluronium hexafluorophosphate (380 mg 1 mmol) in dry DMF (12 mL) is treated with diisopropylethylamine (0.18 mL) and stirred at room temperature for 30 min. A solution of 3-methylsulfamoylbenzylamine (300 mg, 1.5 mmol) in dry DMF (1.5 mL) is added and the mixture is stirred at room temperature for 24 hours. The solvent is removed and the residue is partitioned between EtOAc and water. The organic phase is separated, washed with saturated NaHCO$_3$, water and brine, dried (MgSO$_4$), filtered and concentrated in vacuo. The residue is purified by column chromatography eluting with 60% EtOAc in heptane to afford 2-(4-fluorophenyl)-4-methylpyrimidine-5-carboxylic acid 3-methylsulfamoyl-benzylamide (210 mg, 52%) as a solid. MS: 415 (M+H); $^1$H NMR (300 MHz, DMSO-d$_6$): δ 2.42 (s, 3H), 2.63 (s, 3H), 4.60 (d, 2H), 7.37-7.40 (t, 2H), 7.50 (s, 1H), 7.60-7.75 (m, 3H), 7.80 (s, 1H), 8.45-8.50 (dd, 2H), 8.88 (s, 1H), 9.30 (t, 1H).

Example 43

2-(2-Pyridyl)-pyrimidine-5-carboxylic acid-3-methylsulfamoyl-benzylamide

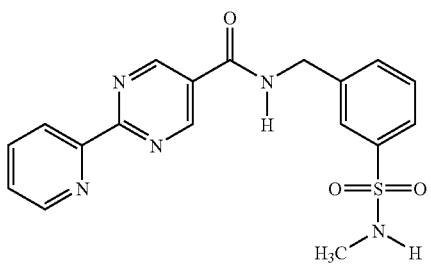

Following procedures similar to those of Example 40 but substituting 2-(2-pyridyl)-pyrimidine-5-carboxylic acid hydrochloride for 2-(3,5-difluoro-phenyl)-pyrimidine-5-carboxylic acid there is prepared 2-(2-pyridyl)-pyrimidine-5-carboxylic acid 3-methylsulfamoyl-benzylamide (183 mg, 48%) as a solid. MS: 384 (M+H); $^1$H NMR (300 MHz, DMSO-$d_6$): δ 2.42 (d, 3H), 4.64 (d, 2H), 7.46-7.54 (m, 1H), 7.51-7.70 (m, 4H), 7.80 (s, 1H), 8.00-8.07 (t, 1H), 8.44-8.50 (d, 1H), 8.80 (d, 1H), 9.37 (s, 2H), 9.55 (t, 1H).

Example 44

2-(3-Pyridyl)-4-methyl-pyrimidine-5-carboxylic acid-3-methylsulfamoyl-benzylamide

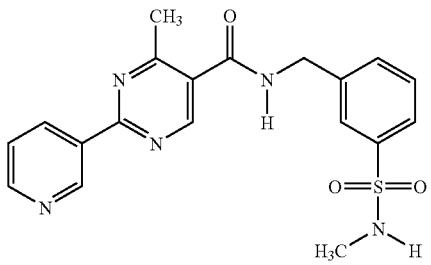

A mixture of 2-(3-pyridyl)-4-methylpyrimidine-5-carboxylic acid (215 mg, 1 mmol, prepared according to the general procedure described in Example 42, steps 1 and 2) and O-(7-azabenzotriazol-1-yl)-N,N,N,N-tetramethyluronium hexafluorophosphate (380 mg, 1 mmol) in dry DMF (12 mL) is treated with of diisopropylethylamine (0.18 mL) and stirred at room temperature for 30 min. 3-Methylsulfamoyl-benzylamine hydrochloride (355 mg, 1.5 mmol) is added and the mixture is stirred at room temperature for 24 hours. The solvent is removed and the residue partitioned between EtOAc and saturated NaHCO$_3$. The organic phase is separated, washed with water and brine, dried (MgSO$_4$), filtered and concentrated in vacuo. The residue is purified by column chromatography eluting with 2% MeOH in EtOAc to afford 2-(3-pyridyl)-4-methyl-pyrimidine-5-carboxylic-acid-3-methylsulfamoyl-benzylamide (180 mg, 45%) as a solid. MS: 398 (M+H); $^1$H NMR (300 MHz, DMSO-$d_6$): δ 2.43 (s, 3H), 2.65 (s, 3H), 4.60 (d, 2H), 7.57-7.71 (m, 4H), 7.79 (s, 1H), 8.68-8.72 (d, 1H), 8.72-8.78 (d, 1H), 8.93 (s, 1H), 9.34 (t, 1H), 9.53 (s, 1H).

General Procedures for Examples 45-67

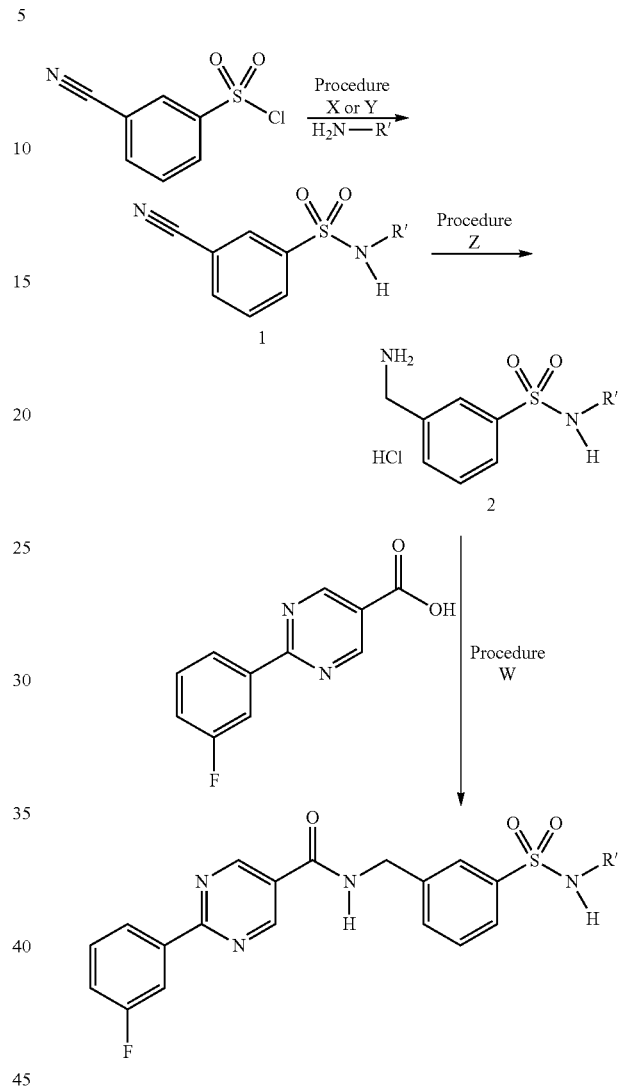

General Procedure X: Sulfonamide Formation

A vial is charged with amine H$_2$N—R' (1 mmol) followed by p-dioxane (5 mL) and piperidinomethyl polystyrene (375 mg, 1.5 mmol, 4 mmol/g resin). The vial is agitated in an orbital shaker for 20 min. 3-Cyano-benzenesulfonyl chloride is added (181 mg, 0.9 mmol) and the reaction vial is placed into the orbital shaker for 18 hours. The vial is removed from the orbital shaker, and MeOH (5 mL) is added followed by the addition of 4-benzyloxybenzaldehyde polystyrene resin (100 mg, 0.3 mmol, 3 mmol/g resin). Agitation is continued in the orbital shaker for 5 hours. The sample is filtered, the resin is washed with MeOH, and the combined organic fractions are concentrated to yield the sulfonamide compound 1.

General Procedure Y: Sulfonamide Formation

A vial is charged with amine H$_2$N—R' (1 mmol) followed by p-dioxane (5 mL) and triethylamine (202 mg, 2 mmol). 3-Cyano-benzenesulfonyl chloride is added (181 mg, 0.9 mmol) and the reaction vial is placed into an orbital shaker for 18 hours. The solvents are removed in vacuo. The residue is partitioned between 1N HCl in water (5 mL) and EtOAc (10 mL). The organic phase is separated, dried (Na$_2$SO$_4$), filtered, and concentrated in vacuo to yield the sulfonamide compound 1.

General Procedure Z: Hydrogenation,

To a solution of the sulfonamide compound (0.9 mmol) in MeOH (9 mL) is added palladium on carbon (200 mg, 10 wt % on carbon, 50 wt % water, ACROS) followed by concentrated HCl in water (1 mL). The reaction is alternately placed under vacuum and hydrogen (1 atm) for 3 cycles before being left under an atmosphere of hydrogen with magnetic stirring for 24 hours. The reaction is filtered through a plug of celite and the filtrate is concentrated in vacuo to yield the amine hydrochloride compound 2.

General Procedure W: Parallel Acylation

To a solution of 2-(3-fluoro-phenyl)-pyrimidine-5-carboxylic acid (196 mg, 0.9 mmol) in DCM (5 mL) is added oxalyl chloride (229 mg, 1.8 mmol) followed by DMF (2 µL). The reaction is stirred for 3 hours. Anhydrous toluene is added (0.5 mL) and the mixture is concentrated in vacuo. The residue is dissolved in EtOAc (7 mL) and the resulting solution is added to a mixture of the amine hydrochloride compound 2 (1 mmol), $Na_2CO_3$ (212 mg) in water (5 mL) a vial with rapid stirring. The reaction is stirred for 18 h, and the organic phase is separated and concentrated in vacuo. The residue is suspended in DMSO (3 mL), filtered, purified via reverse phase HPLC (water and acetonitrile mobile phase with 0.1% TFA buffer) to afford the desired product.

Example 45

2-(3-Fluoro-phenyl)-pyrimidine-5-carboxylic acid 3-ethylsulfamoyl-benzylamide

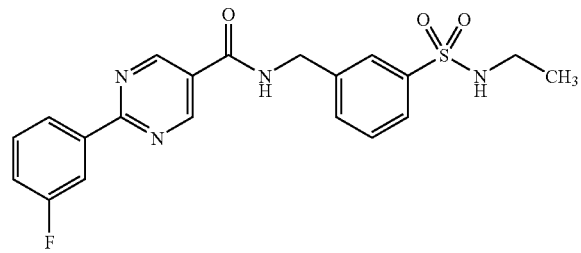

A solution of ethylamine (2 M in MeOH, 6 mmol) in DCM (40 mL) is cooled in an ice water bath and 3-cyano-benzenesulfonyl chloride (402 mg, 2 mmol) is added. The reaction is rapidly stirred for 2 hours. Water (40 mL) is added, and the reaction is acidified to approximately pH ~4 via the careful addition of concentrated HCl. The DCM is removed in vacuo. The precipitate is collected via filtration. The precipitate is hydrogenated using general method Z to afford the amine hydrochloride compound. The amine hydrochloride compound is acylated using acylation procedure W to prepare 2-(3-fluoro-phenyl)-pyrimidine-5-carboxylic acid 3-ethyl-sulfamoyl-benzylamide (449 mg) as a solid. MS: 415 (M+H); $^1$H NMR (300 MHz, $CDCl_3$): δ=0.95 (t, 3H), 2.75-2.9 (m, 2H), 4.65 (d, 2H), 7.47 (t, 1H), 7.55-7.75 (m, 4H), 7.81 (s, 1H), 8.17 (d, 1H), 8.32 (d, 1H), 9.27 (bs, 1H), 9.35 (s, 2H), 9.58 (t, 1H); $IC_{50}$=58 nM.

Example 46

2-(3-Fluoro-phenyl)-pyrimidine-5-carboxylic acid 3-(2-ethoxy-ethylsulfamoyl)-benzylamide

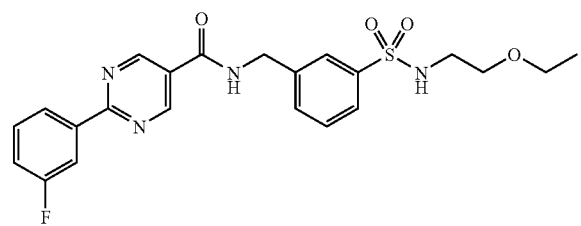

Following general procedures Y, Z, and W, but using 2-ethoxy-ethylamine as the amine in procedure Y, there is prepared 2-(3-fluoro-phenyl)-pyrimidine-5-carboxylic acid 3-(2-ethoxy-ethylsulfamoyl)-benzylamide (210 mg) as a powder. MS: 457 (M−H); $^1$H NMR (300 MHz, $CDCl_3$): δ 1.0 (t, 3H), 2.9 (t, 2H), 4.6 (s, 2H), 7.45 (t, 1H), 7.5-7.7 (m, 4H), 7.8 (s, 1H), 8.16 (d, 1H), 8.31 (d, 1H), 9.3 (s, 1H).

Example 47

2-(3-Fluoro-phenyl)-pyrimidine-5-carboxylic acid 3-(2-hydroxy-propylsulfamoyl)-benzylamide

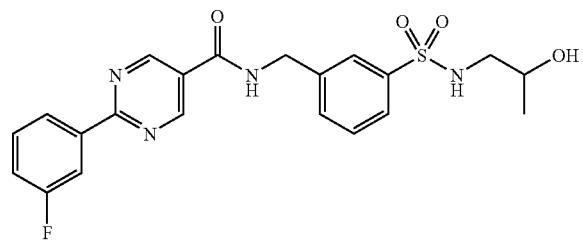

Following general procedures Y, Z, and W, but using 1-amino-propan-2-ol as the amine in procedure Y, there is prepared 2-(3-fluoro-phenyl)-pyrimidine-5-carboxylic acid 3-(2-hydroxy-propylsulfamoyl)-benzylamide (265 mg) as a solid. MS: 443 (M−H); $^1$H NMR (300 MHz, $CDCl_3$): δ 0.97 (d, 3H), 2.57-2.71 (m, 2H), 3.55-3.61 (q, 1H), 4.6 (s, 2H), 7.45 (t, 1H), 7.54-7.77 (m, 4H), 7.8 (s, 1H), 8.16 (d, 1H), 8.31 (d, 1H), 9.34 (s, 2H).

Example 48

2-(3-Fluoro-phenyl)-pyrimidine-5-carboxylic acid 3-cyclopropylsulfamoyl-benzylamide

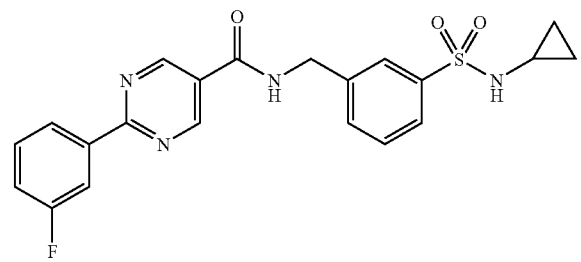

Following general procedures Y, Z, and W, but using cyclopropylamine as the amine in procedure Y, there is prepared 2-(3-fluoro-phenyl)-pyrimidine-5-carboxylic acid 3-cyclopropylsulfamoyl-benzylamide (265 mg) as a solid. MS: 425 (M−H); $^1$H NMR (300 MHz, $CDCl_3$): δ 0.35-0.49 (m, 4H), 2.07-2.14 (m, 1H), 4.65 (d, 2H), 7.46 (dt, 1H), 7.57-7.73 (m, 4H), 7.81 (s, 1H), 7.94 (d, 1H), 8.16 (d, 1H), 8.31 (d, 1H), 9.33 (s, 2H), 9.55 (t, 1H); $IC_{50}$=132 nM.

Example 49

2-(3-Fluoro-phenyl)-pyrimidine-5-carboxylic acid 3-(3-hydroxy-propylsulfamoyl)-benzylamide

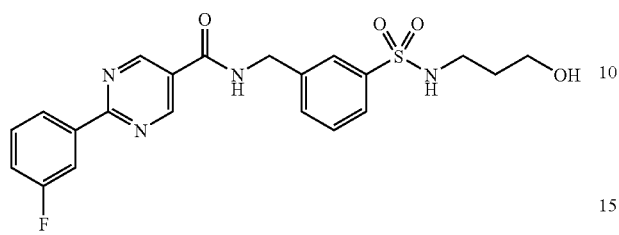

Following general procedures Y, Z, and W, but using 3-aminopropanol as the amine in procedure Y, there is prepared 2-(3-fluoro-phenyl)-pyrimidine-5-carboxylic acid 3-(3-hydroxy-propylsulfamoyl)-benzylamide (175 mg) as a powder. MS: 443 (M−H); $^1$H NMR (300 MHz, CDCl$_3$): δ 1.51 (p, 2H), 2.79 (t, 2H), CH$_2$ hidden in water peak, 4.64 (s, 2H), 7.45 (dt, 1H), 7.55-7.70 (m, 4H), 7.79 (s, 1H), 8.135 (d, 1H), 8.31 (d, 1H), 9.29 (s, N—H), 9.33 (s, 1H); IC$_{50}$=22 nM.

Example 50

2-(3-Fluoro-phenyl)-pyrimidine-5-carboxylic acid 3-(2-methoxy-ethylsulfamoyl)-benzylamide

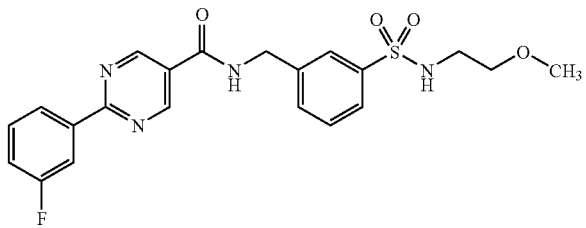

Following general procedures Y, Z, and W, but using 2-methoxyethylamine as the amine in procedure Y, there is prepared 2-(3-fluoro-phenyl)-pyrimidine-5-carboxylic acid 3-(2-methoxy-ethylsulfamoyl)-benzylamide (190 mg) as a powder. MS: 443 (M−H); $^1$H NMR (300 MHz, CDCl$_3$): δ 2.90 (t, 2H), 3.14 (s, 3H), CH$_2$ hidden under water peak, 4.63 (s, 2H), 7.45 (dt, 1H), 7.54-7.71 (m, 4H), 7.80 (s, 1H), 8.15 (d, 1H), 8.31 (d, 1H), 9.33 (s, 2H), 9.57 (bs, N—H).

Example 51

2-(3-Fluoro-phenyl)-pyrimidine-5-carboxylic acid 3-(3-methoxy-propylsulfamoyl)-benzylamide

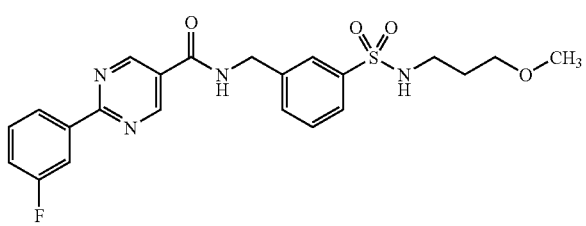

Following general procedures Y, Z, and W, but using 3-methoxypropylamine as the amine in procedure Y, there is prepared 2-(3-fluoro-phenyl)-pyrimidine-5-carboxylic acid 3-(3-methoxy-propylsulfamoyl)-benzylamide (201 mg) as a powder. MS: 457 (M−H); $^1$H NMR (300 MHz, CDCl$_3$): δ 1.57 (p, 2H), 2.77 (t, 2H), 3.13 (s, 3H), 3.24 (t, 2H), 4.63 (s, 2H), 7.45 (dt, 1H), 7.55-7.70 (m, 4H), 7.79 (s, 1H), 8.15 (d, 1H), 8.31 (d, 1H), 9.33 (s, 2H), 9.58 (bs, N—H); IC$_{50}$=37 nM.

Example 52

2-(3-Fluoro-phenyl)-pyrimidine-5-carboxylic acid 3-(4-methoxy-butylsulfamoyl)-benzylamide

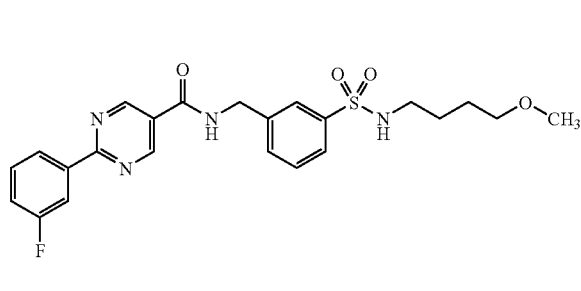

Following general procedures Y, Z, and W, but using 4-methoxybutylamine as the amine in procedure Y, there is prepared 2-(3-fluoro-phenyl)-pyrimidine-5-carboxylic acid 3-(4-methoxy-butylsulfamoyl)-benzylamide (220 mg) as a powder. MS: 471 (M−H); $^1$H NMR (300 MHz, CDCl$_3$): δ 1.01 (t, 2H), 1.57 (p, 2H), 2.78 (t, 2H), CH$_2$ and CH$_3$ hidden under water peak, 4.63 (s, 2H), 7.45 (dt, 1H), 7.55-7.70 (m, 4H), 7.79 (s, 1H), 8.16 (d, 1H), 8.31 (d, 1H), 9.33 (s, 2H), 9.59 (bs, N—H).

Example 53

2-(3-Fluoro-phenyl)-pyrimidine-5-carboxylic acid 3-cyclohexylsulfamoyl-benzylamide

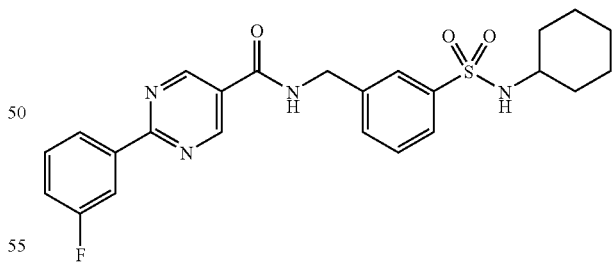

Following general procedures Y, Z, and W, but but using cyclohexylamine as the amine in procedure Y, there is prepared 2-(3-fluoro-phenyl)-pyrimidine-5-carboxylic acid 3-cyclohexylsulfamoyl-benzylamide (240 mg) as a powder. MS: 467 (M−H); $^1$H NMR (300 MHz, CDCl$_3$): δ 1.07 (t, 6H), 1.41 (bs, 1H), 1.53-1.55 (m, 4H), 2.90 (bs, 1H), 4.63 (d, 2H), 7.45 (dt, 1H), 7.53-7.72 (m, 4H), 7.80 (s, 1H), 8.15 (dd, 1H), 8.30 (d, 1H), 9.33 (s, 2H), 9.55 (t, 1H).

Example 54

2-(3-Fluoro-phenyl)-pyrimidine-5-carboxylic acid 3-(2-hydroxy-1,1-dimethyl-ethylsulfamoyl)-benzylamide

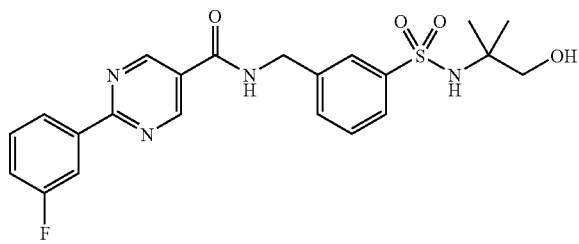

Following general procedures Y, Z, and W, but using 2-Amino-2-methyl-propan-1-ol as the amine in procedure Y, there is prepared 2-(3-fluoro-phenyl)-pyrimidine-5-carboxylic acid 3-(2-hydroxy-1,1-dimethyl-ethylsulfamoyl)-benzylamide (90 mg) as a solid. MS: 457 (M−H); $^1$H NMR (300 MHz, CDCl$_3$): δ 1.00 (s, 6H), 3.19 (d, 2H), 4.63 (d, 2H), 4.75 (t, 1H), 7.35 (s, 1H), 7.45 (dt, 1H), 7.52-7.67 (m, 3H), 7.75 (d, 1H), 7.84 (s, 1H), 8.16 (d, 1H), 8.31 (d, 1H), 9.33 (s, 2H), 9.54 (t, 1H); IC$_{50}$=60 nM.

Example 55

2-(3-Fluoro-phenyl)-pyrimidine-5-carboxylic acid 3-sulfamoyl-benzylamide

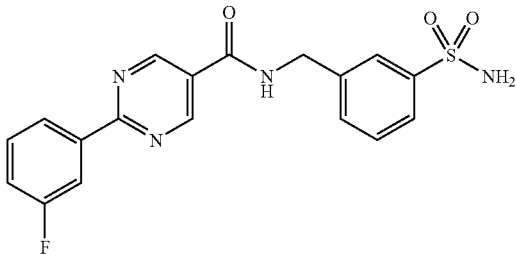

Following general procedures Y, Z, and W, but using tert-butylamine as the amine in procedure Y, there is prepared 2-(3-fluoro-phenyl)-pyrimidine-5-carboxylic acid 3-sulfamoyl-benzylamide (25 mg) as a powder. MS: 385 (M−H); $^1$H NMR (300 MHz, CDCl$_3$): δ 4.62 (d, 2H), 7.38 (s, 1H), 7.45 (t, 1H), 7.53-7.75 (m, 5H), 7.83 (s, 1H), 8.16 (d, 1H), 8.32 (d, 1H), 8.34 (s, 1H), 9.32 (s, 2H), 9.55 (t, 1H); IC$_{50}$=31 nM.

Example 56

2-(3-Fluoro-phenyl)-pyrimidine-5-carboxylic acid 3-(2-morpholin-4-yl-ethylsulfamoyl-benzylamide

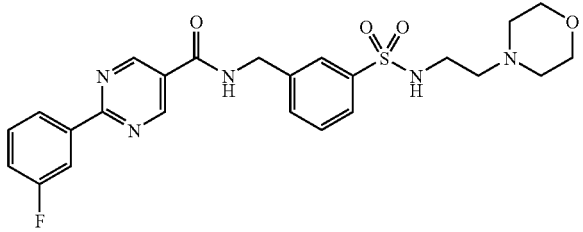

Following general procedures X, Z, and W, but using 2-morpholin-4-yl-ethylamine as the amine in procedure X, there is prepared 2-(3-fluoro-phenyl)-pyrimidine-5-carboxylic acid 3-(2-morpholin-4-yl-ethylsulfamoyl)-benzylamide (150 mg) containing small amount of TFA. MS: 500 (M+H); $^1$H NMR (300 MHz, CDCl$_3$): δ 3.0-3.4 (m, 8H), 3.5-3.75 (m, 2H), 3.85-4.1 (m, 2H), 4.64 (d, 2H), 7.45 (dt, 1H), 7.60-7.75 (m, 4H), 7.82 (s, 1H), 8.01 (s, 1H), 8.16 (d, 1H), 8.30 (d, 1H), 9.33 (s, 2H), 9.56 (t, 1H), 9.69 (m, 1H); IC$_{50}$=37 nM.

Example 57

2-(3-Fluoro-phenyl)-pyrimidine-5-carboxylic acid 3-(2-piperidin-1-yl-ethylsulfamoyl)-benzylamide

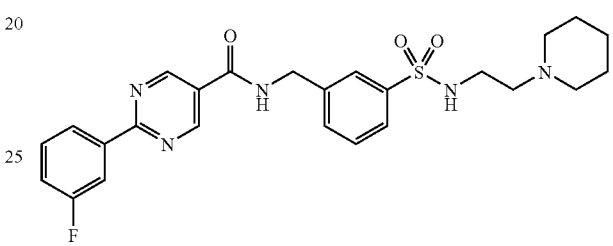

Following general procedures X, Z, and W, but using 2-piperidin-1-yl-ethylamine as the amine in procedure X, there is prepared 2-(3-fluoro-phenyl)-pyrimidine-5-carboxylic acid 3-(2-piperidin-1-yl-ethylsulfamoyl)-benzylamide (125 mg) containing small amount of TFA. MS: 498 (M+H); $^1$H NMR (300 MHz, CDCl$_3$): δ 1.2-1.8 (m, 6H), 2.8-2.95 (m, 2H), 3.11 (bs, 4H), 3.3-3.5 (m, 2H), 4.64 (d, 2H), 7.46 (dt, 1H), 7.60-7.75 (m, 4H), 7.82 (s, 1H), 8.00 (bs, 1H), 8.16 (d, 1H), 8.31 (d, 1H), 9.08 (m, 1H), 9.33 (s, 2H), 9.56 (t, 1H).

Example 58

2-(3-Fluoro-phenyl)-pyrimidine-5-carboxylic acid 3-[2-(1-methyl-pyrrolidin-2-yl)-ethylsulfamoyl]-benzylamide

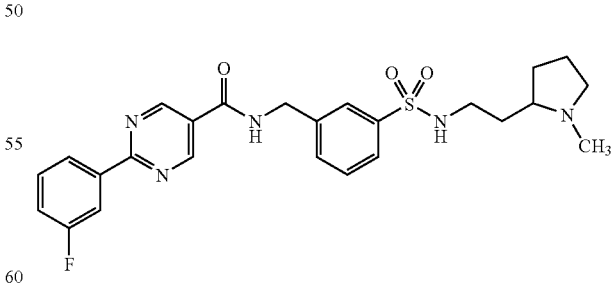

Following general procedures X, Z, and W, but using 2-(1-methyl-pyrrolidin-2-yl)-ethylamine as the amine in procedure X, there is prepared 2-(3-fluoro-phenyl)-pyrimidine-5-carboxylic acid 3-[2-(1-methyl-pyrrolidin-2-yl)- ethylsulfamoyl]-benzylamide (110 mg). MS: 498 (M+H); ¹H NMR (300 MHz, CDCl₃): δ 1.4-1.7 (m, 2H), 1.7-2.2 (m, 4H), 2.7-2.9 (m, 5H), 3.0-3.1 (m, 1H), 3.1-3.3 (m, 1H), 3.4-3.6 (m, 1H), 4.64 (d, 2H), 7.46 (dt, 1H), 7.58-7.72 (m, 4H), 7.79 (s, 1H), 8.16 (d, 1H), 8.31 (d, 1H), 9.33 (s, 2H), 9.56 (t, 1H).

Example 59

2-(3-Fluoro-phenyl)-pyrimidine-5-carboxylic acid 3-[(1-ethyl-pyrrolidin-2-ylmethyl)-sulfamoyl]-benzylamide

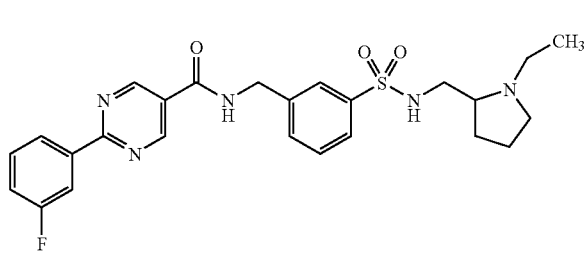

Following general procedures X, Z, and W, but using C-(1-ethyl-pyrrolidin-2-yl)-methylamine as the amine in procedure X there is prepared 2-(3-fluoro-phenyl)-pyrimidine-5-carboxylic acid 3-[(1-ethyl-pyrrolidin-2-ylmethyl)-sulfamoyl]-benzylamide (85 mg) containing small amount of TFA. MS: 498 (M+H); ¹H NMR (300 MHz, CDCl₃): δ 1.20 (t, 3H), 1.6-2.2 (m, 4H), 2.95-3.2 (m, 4H), 3.25-3.45 (m, 2H), 3.45-3.6 (m, 1H), 4.65 (d, 2H), 7.46 (dt, 1H), 7.60-7.76 (m, 4H), 7.83 (s, 1H), 8.09-8.17 (m, 2H), 8.31 (d, 1H), 9.13 (bs, 1H), 9.34 (s, 2H), 9.57 (t, 1H).

Example 60

2-(3-Fluoro-phenyl)-pyrimidine-5-carboxylic acid 3-[2-(1H-imidazol-4-yl)-ethylsulfamoyl]-benzylamide

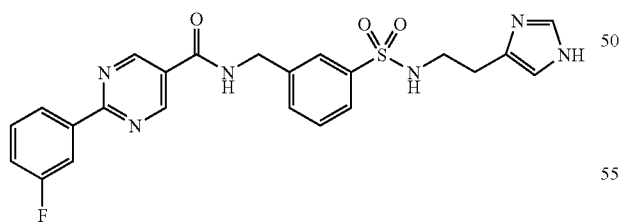

Following general procedures X, Z, and W, but using 2-(1H-imidazol-4-yl)-ethylamine as the amine in procedure X, there is prepared 2-(3-fluoro-phenyl)-pyrimidine-5-carboxylic acid 3-[2-(1H-imidazol-4-yl)-ethylsulfamoyl]-benzylamide (30 mg) as a solid. MS: 481 (M+H); ¹H NMR (300 MHz, CDCl₃): δ 2.77 (t, 2H), 3.06 (t, 2H), 4.63 (d, 2H), 7.40 (s, 1H), 7.46 (t, 1H), 7.56-7.96 (m, 4H), 7.77 (s, 1H), 7.86 (t, 1H), 8.16 (d, 1H), 8.31 (d, 1H), 9.32 (s, 2H), 9.55 (t, 1H); IC₅₀=61 nM.

Example 61

2-(3-Fluoro-phenyl)-pyrimidine-5-carboxylic acid 3-[3-(2-methyl-piperidin-1-yl)-propylsulfamoyl]-benzylamide

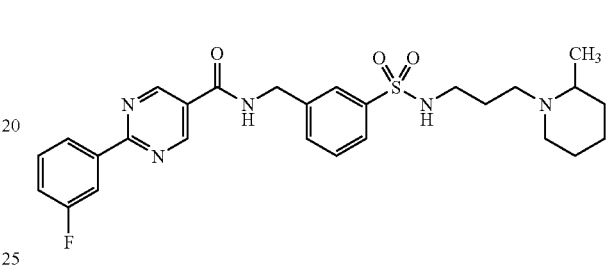

Following general procedures X, Z, and W, but using 3-(2-methyl-piperidin-1-yl)-propylamine as the amine in procedure X there is prepared 2-(3-fluoro-phenyl)-pyrimidine-5-carboxylic acid 3-[3-(2-methyl-piperidin-1-yl)-propylsulfamoyl]-benzylamide (155 mg) containing small amount of TFA. MS: 526 (M+H); ¹H NMR (300 MHz, CDCl₃): δ 1.19 (dd, 3H), 1.3-1.9 (m, 8H), 2.75-3.25 (m, 6H), 3.3-3.6 (m, 1H), 4.64 (d, 2H), 7.46 (dt, 1H), 7.58-7.72 (m, 4H), 7.79-7.85 (m, 2H), 8.16 (d, 1H), 8.31 (d, 1H), 8.9-9.2 (m, 1H), 9.34 (s, 2H), 9.57 (t, 1H).

Example 62

2-(3-Fluoro-phenyl)-pyrimidine-5-carboxylic acid 3-(3-pyrrolidin-1-yl-propylsulfamoyl)-benzylamide

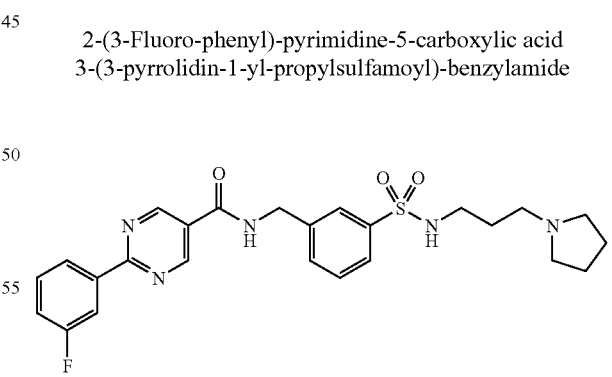

Following general procedures X, Z, and W, but using 3-pyrrolidin-1-yl-propylamine as the amine in procedure X, there is prepared 2-(3-fluoro-phenyl)-pyrimidine-5-carboxylic acid 3-(3-pyrrolidin-1-yl-propylsulfamoyl)-benzylamide (105 mg). MS: 498 (M+H); ¹H NMR (300 MHz, CDCl₃): δ 1.7-1.9 (m, 4H), 1.9-2.1 (m, 2H), 2.8-3.0 (m, 4H), 3.05-3.15 (m, 2H), 3.2-3.35 (m, 2H), 4.64 (d, 2H), 7.46 (dt, 1H), 7.58-

7.77 (m, 4H), 7.79 (m, 1H), 8.16 (d, 1H), 8.31 (d, 1H), 9.34 (s, 2H), 9.41 (bs, 1H), 9.56 (t, 1H).

Example 63

2-(3-Fluoro-phenyl)-pyrimidine-5-carboxylic acid 3-(2-dimethylamino-ethylsulfamoyl)-benzylamide

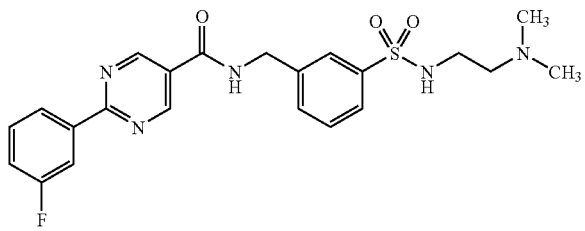

Following general procedures X, Z, and W, but using $N^1,N^1$-dimethyl-ethane-1,2-diamine as the amine in procedure X there is prepared 2-(3-fluoro-phenyl)-pyrimidine-5-carboxylic acid 3-(2-dimethylamino-ethylsulfamoyl)-benzylamide (38 mg) as a solid. MS: 458 (M+H); $^1$H NMR (300 MHz, CDCl$_3$): δ 2.78 (s, 6H), 3.0-3.2 (m, 4H), 4.65 (d, 2H), 7.46 (dt, 1H), 7.60-7.76 (m, 4H), 8.01 (t, 1H), 8.16 (d, 1H), 8.31 (d, 1H), 9.33 (bs, 3H), 9.56 (t, 1H); IC$_{50}$=45 nM.

Example 64

2-(3-Fluoro-phenyl)-pyrimidine-5-carboxylic acid 3-(2-diethylamino-ethylsulfamoyl)-benzylamide

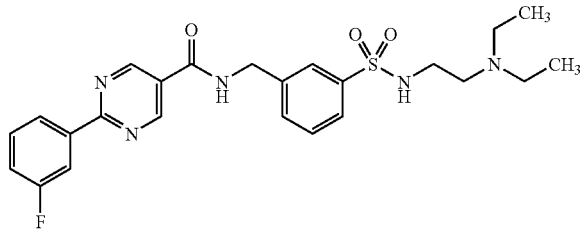

Following general procedures X, Z, and W, but using $N^1,N^1$-diethyl-ethane-1,2-diamine as the amine in procedure X there is prepared 2-(3-fluoro-phenyl)-pyrimidine-5-carboxylic acid 3-(2-diethylamino-ethylsulfamoyl)-benzylamide (128 mg) containing small amount of TFA. MS: 486 (M+H); $^1$H NMR (300 MHz, CDCl$_3$): δ 1.16 (t, 6H), 3.0-3.2 (m, 8H), 4.65 (d, 2H), 7.46 (dt, 1H), 7.60-7.76 (m, 4H), 7.83 (s, 1H), 8.02 (t, 1H), 8.16 (d, 1H), 8.31 (d, 1H), 9.17 (bs, 1H), 9.33 (s, 2H), 9.57 (t, 1H).

Example 65

2-(3-Fluoro-phenyl)-pyrimidine-5-carboxylic acid 3-(3-dimethylamino-2,2-dimethyl-propylsulfamoyl)-benzylamide

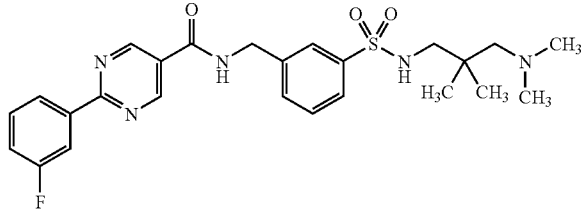

Following general procedures X, Z, and W, but using 2,2,$N^1,N^1$-Tetramethyl-propane-1,3-diamine as the amine in procedure X there is prepared 2-(3-fluoro-phenyl)-pyrimidine-5-carboxylic acid 3-(3-dimethylamino-2,2-dimethyl-propylsulfamoyl)-benzylamide (190 mg) containing small amount of TFA. MS: 500 (M+H); $^1$H NMR (300 MHz, CDCl$_3$): δ 0.95 (s, 6H), 2.68 (d, 2H), 2.84 (d, 6H), 3.03 (d, 2H), 4.64 (d, 2H), 7.46 (dt, 1H), 7.58-7.74 (m, 4H), 7.80 (s, 1H), 7.85 (t, 1H), 8.16 (d, 1H), 8.31 (d, 1H), 8.85 (bs, 1H), 9.34 (s, 2H), 9.57 (t, 1H); IC$_{50}$=35 nM.

Example 66

2-(3-Fluoro-phenyl)-pyrimidine-5-carboxylic acid 3-(5-dimethylamino-pentylsulfamoyl)-benzylamide

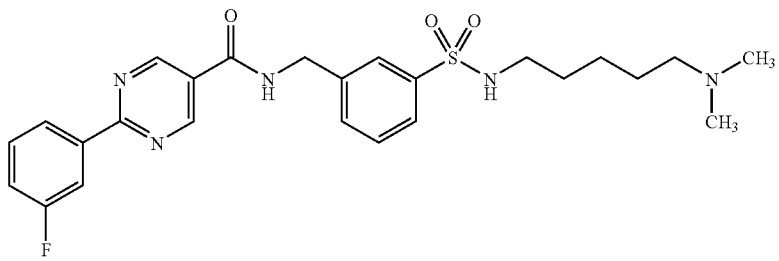

Following general procedures X, Z, and W, but using $N^1,N^1$-dimethyl-pentane-1,5-diamine as the amine in procedure X there is prepared 2-(3-fluoro-phenyl)-pyrimidine-5-carboxylic acid 3-(5-dimethylamino-pentylsulfamoyl)-benzylamide (175 mg). MS: 500 (M+H); $^1$H NMR (300 MHz, CDCl$_3$): δ 1.22-1.27 (m, 2H), 1.34-1.44 (m, 2H), 1.44-1.57 (m, 2H), 2.70-2.74 (m, 8H), 2.92-2.99 (m, 2H), 4.63 (d, 2H), 7.46 (dd, 1H), 7.56-7.70 (m, 4H), 7.78 (s, 1H), 8.16 (d, 1H), 8.31 (d, 1H), 9.33 (s, 2H), 9.56 (t, 1H).

Example 67

2-(3-Fluoro-phenyl)-pyrimidine-5-carboxylic acid 3-(2-diisopropylamino-ethylsulfamoyl)-benzylamide

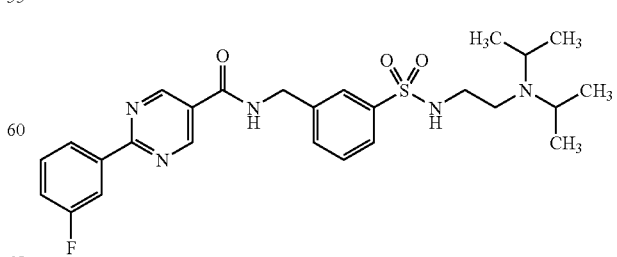

Following general procedures X, Z, and W, but using $N^1,N^1$-diisopropyl-ethane-1,2-diamine as the amine in procedure X there is prepared 2-(3-fluoro-phenyl)-pyrimidine-5-carboxylic acid 3-(2-diisopropylamino-ethylsulfamoyl)-benzylamide (150 mg). MS: 514 (M+H); $^1$H NMR (300 MHz, CDCl$_3$): δ 1.21 (t, 12H), 3.06-0.308 (m, 4H), 3.58-3.65 (m, 2H), 4.64 (d, 2H), 7.46 (dd, 1H), 7.60-7.75 (m, 4H), 7.82 (s, 1H), 8.07 (t, 1H), 8.16 (d, 1H), 8.31 (d, 1H), 9.34 (s, 2H), 9.59 (t, 1H).

Example 68

2-(3-Fluoro-phenyl)-4-methyl-pyrimidine-5-carboxylic acid 3-(methanesulfonylamino-methyl)-benzylamide

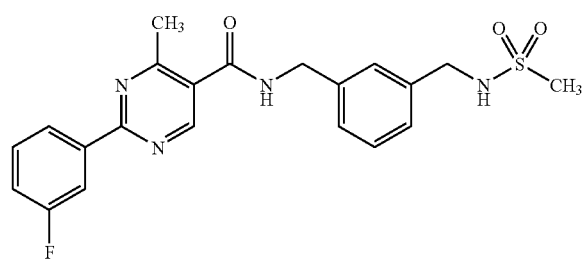

Step 1. Na° (0.66 g, 28.6 mmol) is added to anhydrous EtOH (100 mL) and stirred at room temperature for 15 min. 3-Fluorobenzamidine hydrochloride (4.87 g, 27.8 mmol) is added and the solution is stirred for 15 min. 2-Dimethylaminomethylene-3-oxo-butyric acid ethyl ester (5.3 g, 28.6 mmol,) is added and the reaction mixture is heated at reflux under N$_2$ for 1 hours. The reaction is cooled to room temperature and concentrated in vacuo. The residue is dissolved in EtOAc (300 mL), washed with brine (2×100 mL), dried (Na$_2$SO$_4$), filtered, and concentrated to afford 2-(3-fluoro-phenyl)-4-methyl-pyrimidine-5-carboxylic acid ethyl ester (6.8 g, 99%). MS: 261 (M+H); $^1$H NMR (300 MHz, CDCl$_3$): δ 1.43 (t, J=7.0 Hz, 3H), 2.92 (s, 3H), 4.42 (q, J=7.0 Hz, 2H), 7.24 (m, 1H), 7.45 (m, 1H), 8.27 (m, 1H), 8.37 (m, 1H), 9.21 (s, 1H).

Step 2. A solution of 2-(3-fluoro-phenyl)-4-methyl-pyrimidine-5-carboxylic acid ethyl ester (6.7 g, 27.2 mmol) and NaOH (2.1 g, 54.4 mmol) in a 1:1:1 solution of THF, MeOH and water (300 mL) is heated at reflux for 45 min. The THF/MeOH is evaporated, and the aqueous solution is treated with 3 N HCl to adjust the pH to between 2 and 3. The solid is filtered off, washed with water and dried in vacuo to yield 2-(3-fluoro-phenyl)-4-methyl-pyrimidine-5-carboxylic acid (5.4 g, 91%) as a solid. MS: 233 (M+H); $^1$H NMR (300 MHz, CD$_3$OD): δ 2.85 (s, 3H), 7.24 (m, 1H), 7.50 (m, 1H), 8.17 (m, 1H), 8.32 (m, 1H), 9.20 (s, 1H).

Step 3. To a solution of 2-(3-fluoro-phenyl)-4-methyl-pyrimidine-5-carboxylic acid (0.195 g, 0.89 mmol) in THF (5 mL) is added carbonyl diimidazole (0.18 g, 1.1 mmol) and heated at 60° C. for 2 hours. The mixture is cooled to room temperature. (3-Aminomethyl-benzyl)-carbamic acid tert-butyl ester (0.25 mL, 1.1 mmol) is added and the mixture is stirred for 12 hours. The mixture is diluted with EtOAc (100 mL), washed with brine (2×50 mL), dried with Na$_2$SO$_4$, filtered and concentrated in vacuo. The residue is purified by flash chromatography eluting with 20%-80% EtOAc/heptane to afford [3-({[2-(3-fluoro-phenyl)-4-methyl-pyrimidine-5-carbonyl]-amino}-methyl)-benzyl]-carbamic acid tert-butyl ester (0.32 g, 80%) as a solid. MS: 451 (M+H); $^1$H NMR (300 MHz, DMSO-d$_6$): δ 1.38 (s, 9H), 2.65 (s, 3H), 4.14 (d, J=6.1 Hz, 2H), 4.50 (d, J=5.6 Hz, 2H), 7.15 (m, 1H), 7.24 (m, 1H), 7.31 (m, 1H), 7.43 (m, 1H), 7.62 (m, 1H), 8.13 (m, 1H), 8.28 (m, 1H), 8.89 (s, 1H), 9.23 (m, 1H).

Step 4. To a solution of [3-({[2-(3-fluoro-phenyl)-4-methyl-pyrimidine-5-carbonyl]-amino}-methyl)-benzyl]-carbamic acid tert-butyl ester (0.05 g, 0.111 mmol) in DCM (2 mL) at 0° C. is added TFA (0.013 mL. 0.111 mmol) and the mixture is stirred for 2.5 hours. The mixture is concentrated in vacuo. The residue is dissolved in THF (2 mL). Et$_3$N (0.05 mL, 0.333 mmol) and methanesulfonyl chloride (0.010 mL, 0.133 mmol) are added and the mixture is stirred for 12 hours. The mixture is diluted with EtOAc (100 mL), washed with saturated aqueous NH$_4$Cl (2×50 mL), dried with Na$_2$SO$_4$, filtered, and concentrated in vacuo. The residue is purified by flash chromatography eluting with 20%-80% EtOAc/heptane to afford 2-(3-fluoro-phenyl)-4-methyl-pyrimidine-5-carboxylic acid 3-(methanesulfonylamino-methyl)-benzylamide (0.03 g, 64%) as a powder. MS: 429 (M+H); $^1$H NMR (300 MHz, DMSO-d$_6$): δ 2.65 (s, 3H), 2.86 (s, 3H), 4.18 (d, J=6.3 Hz, 2H), 4.50 (d, J=5.9 Hz, 2H), 7.27-7.45 (m, 3H), 7.62 (m, 2H), 8.13 (m, 1H), 8.28 (m, 1H), 8.90 (s, 1H), 9.25 (m, 1H); IC$_{50}$=48.5 nM.

Example 69

2-(3-Fluoro-phenyl)-4-methyl-pyrimidine-5-carboxylic acid 3-[(propane-2-sulfonylamino)-methyl]-benzylamide

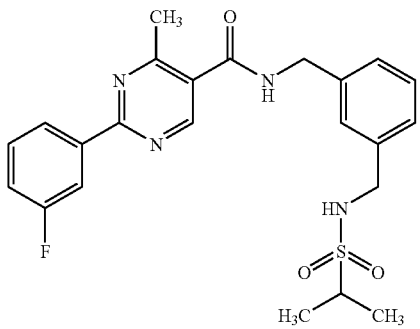

Following procedures similar to those of Example 68 (step 3) but substituting isopropanesulfonyl chloride (0.57 mmol) for (3-aminomethyl-benzyl)-carbamic acid tert-butyl ester there is prepared 2-(3-fluoro-phenyl)-4-methyl-pyrimidine-5-carboxylic acid 3-[(propane-2-sulfonylamino)-methyl]-benzylamide (100 mg) as a solid. MS: 456 (M+H); $^1$H NMR (300 MHz, DMSO-d$_6$): δ 1.22 (d, J=6.8 Hz, 6H), 2.65 (s, 3H), 3.10 (m, 1H), 4.18 (d, J=6.2 Hz, 2H), 4.51 (s, 2H), 7.27-7.45 (m, 3H), 7.62 (m, 2H), 8.14 (m, 1H), 8.26 (m, 1H), 8.90 (s, 1H), 9.25 (m, 1H).

Example 70

2-(3-Fluoro-phenyl)-4-methyl-pyrimidine-5-carboxylic acid 3-methylsulfamoylmethyl-benzylamide

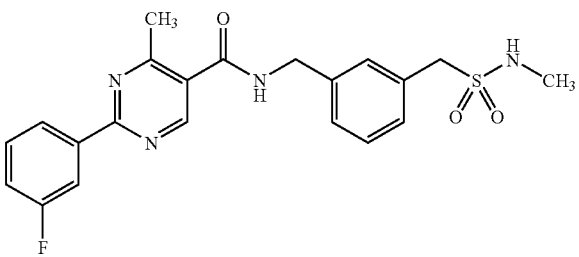

Step 1: A solution of 3-bromomethyl-benzonitrile (2 g, 10.2 mmol) in EtOH (50 mL) is treated with a solution of Na$_2$SO$_3$ (1.3 g, 10.3 mmol) in H$_2$O (50 mL) and heated at reflux for 4 hours. The mixture is concentrated in vacuo. The residue is suspended in DCM (100 mL) and DMF (1 mL), cooled to 0° C. and treated with oxalyl chloride (8 mL, 43.4 mmol). The mixture is warmed to room temperature and stirred for 3 hours. The mixture is diluted with brine, extracted with DCM (2×100 mL), dried with Na$_2$SO$_4$, filtered, and concentrated in vacuo. The residue is dissolved in THF (25 mL), methylamine (2 M, 12.5 mL, 25 mmol) is added and the mixture is stirred for 12 hours. The mixture is diluted with EtOAc (100 mL), washed with saturated aqueous NH$_4$Cl (2×100 mL), dried with Na$_2$SO$_4$, filtered, and concentrated in vacuo. The residue is purified by flash chromatography eluting with 20%-80% EtOAc/heptane to afford C-(3-cyano-phenyl)-N-methyl-methanesulfonamide (1.5 g, 69%) as a powder. MS: 209 (M+H); $^1$H NMR (300 MHz, DMSO-d$_6$): δ 2.60 (d, J=4.8 Hz, 3H), 4.44 (s, 2H), 7.02 (m, 1H), 7.61 (m, 1H), 7.74 (m, 1H), 7.85 (m, 2H).

Step 2: To a solution of C-(3-cyano-phenyl)-N-methyl-methanesulfonamide (42 mg, 0.2 mmol) in THF (4 mL) is added a solution of BH$_3$$^-$THF in THF (1 M, 1 mL). The mixture is sealed and heated in a microwave reactor at 100° C. for 120 seconds. The mixture is poured into 1 M HCl (20 mL), basified with 3 M NaOH to pH ~10, extracted with DCM (2×50 mL), dried with Na$_2$SO$_4$, filtered, and concentrated in vacuo to afford C-(3-aminomethyl-phenyl)-N-methyl-methanesulfonamide, which is used directly in the next without further purification.

Step 3: Following procedures similar to those of Example 68 (step 3) but substituting C-(3-aminomethyl-phenyl)-N-methyl-methanesulfonamide (2.3 mmol) for (3-aminomethyl-benzyl)-carbamic acid tert-butyl ester there is prepared 2-(3-fluoro-phenyl)-4-methyl-pyrimidine-5-carboxylic acid 3-methylsulfamoylmethyl-benzylamide (30 mg) as a solid. MS: 429 (M+H); $^1$H NMR (300 MHz, DMSO-d$_6$): δ 2.58 (d, J=4.8 Hz, 3H), 2.65 (s, 3H), 4.34 (s, 2H), 4.53 (d, J=5.7 Hz, 2H), 6.92 (m, 1H), 7.27-7.45 (m, 3H), 7.62 (m, 2H), 8.14 (m, 1H), 8.28 (m, 1H), 8.90 (s, 1H), 9.23 (m, 1H).

Example 71

2-(3-Fluoro-phenyl)-4-methyl-pyrimidine-5-carboxylic acid 3-(isopropylsulfamoyl-methyl)-benzylamide

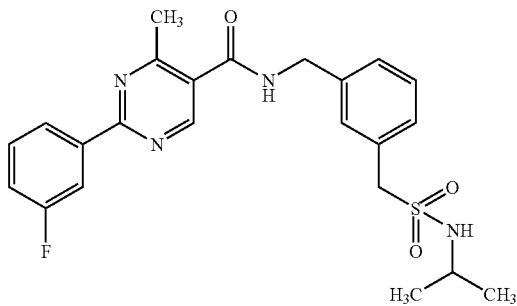

Step 1: To a solution of 3-bromomethyl-benzonitrile (2 g, 10.2 mmol) in EtOH (50 mL) is added a solution of Na$_2$SO$_3$ (1.3 g, 10.3 mmol) in H$_2$O (50 mL) and the mixture is heated at reflux for 4 hours. The mixture is concentrated in vacuo. The residue is suspended in DCM (100 mL) and DMF (1 mL), cooled to 0° C. and treated with oxalyl chloride (4.5 mL, 24.4 mmol). The mixture is warmed to room temperature for 3 hours. The mixture is diluted with brine (100 mL), extracted with DCM (2×100 mL), dried with Na$_2$SO$_4$, filtered, and concentrated in vacuo. The residue is dissolved in THF (100 mL), and treated with isopropyl amine (3.5 mL, 40.8 mmol). The mixture is stirred for 12 h, diluted with EtOAc (200 mL), washed with saturated aqueous NH$_4$Cl (2×100 mL), dried with Na$_2$SO$_4$, filtered, and concentrated in vacuo. The residue is purified by flash chromatography eluting with 20%-80% EtOAc/heptane to afford C-(3-cyano-phenyl)-N-isopropyl-methanesulfonamide as a powder. MS: 237 (M+H); $^1$H NMR (300 MHz, DMSO-d$_6$): δ 1.10 (d, J=6.6 Hz, 6H), 3.36 (m, 1H), 4.42 (s, 2H), 7.09 (m, 1H), 7.57 (m, 1H), 7.74 (m, 1H), 7.85 (m, 2H).

Step 2: To a solution of C-(3-cyano-phenyl)-N-isopropyl-methanesulfonamide (0.5 g, 2.06 mmol) in THF (10 mL) is added a solution of BH$_3$$^-$THF in THF (1 M, 10.3 mL). The mixture is sealed and heated in a microwave reactor at 100° C. for 120 seconds. The mixture is poured into 1 M HCl (50 mL), basified with 3 M NaOH to pH ~10, extracted with DCM, dried with Na$_2$SO$_4$, filtered, and concentrated in vacuo to afford C-(3-aminomethyl-phenyl)-N-isopropyl-methanesulfonamide, which is used directly in the next step without further purification.

Step 3: Following procedures similar to those of Example 68 (step 3) but substituting C-(3-aminomethyl-phenyl)-N-isopropyl-methanesulfonamide (2 mmol) for (3-aminomethyl-benzyl)-carbamic acid tert-butyl ester there is prepared 2-(3-fluoro-phenyl)-4-methyl-pyrimidine-5-carboxylic acid 3-(isopropylsulfamoyl-methyl)-benzylamide (160 mg) as a solid. MS: 457 (M+H); $^1$H NMR (300 MHz, DMSO-d$_6$): δ 1.09 (d, J=6.4, 6H), 2.65 (s, 3H), 3.37 (m, 1H), 4.31 (s, 2H), 4.53 (d, J=5.8, 2H), 6.99 (d, J=7.1 Hz, 1H), 7.27-7.45 (m, 3H), 7.62 (m, 1H), 8.13 (m, 1H), 8.28 (m, 1H), 8.90 (s, 1H), 9.24 (m, 1H); IC$_{50}$=34 nM.

Example 72

2-(3-Fluoro-phenyl)-pyrimidine-5-carboxylic acid 3-(methanesulfonylamino-methyl)-benzylamide

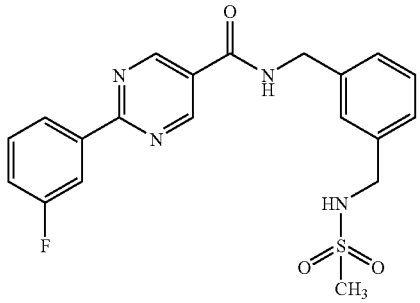

Step 1. To a solution of 2-(3-fluoro-phenyl)-pyrimidine-5-carboxylic acid (0.5 g, 2.25 mmol) in THF (25 mL) is added carbonyl diimidazole (0.5 g, 2.7 mmol) and heated at 60° C. for 2 hours. The mixture is cooled to room temperature and (3-aminomethyl-benzyl)-carbamic acid tert-butyl ester (0.67 mL, 2.7 mmol) is added. The mixture is stirred for 12 h, diluted with EtOAc (100 mL), washed with brine (2×50 mL), dried with Na$_2$SO$_4$, filtered and concentrated in vacuo. The residue is purified by flash chromatography eluting with 20%-80% EtOAc/heptane to afford [3-({[2-(3-fluoro-phenyl)-pyrimidine-5-carbonyl]-amino}-methyl)-benzyl]-carbamic acid tert-butyl ester (0.8 g, 80%) as a solid. MS: 437 (M+H); $^1$H NMR (300 MHz, DMSO-d$_6$): δ 1.35 (s, 9H), 4.13 (d, J=6.1 Hz, 2H), 4.54 (d, J=5.9 Hz, 2H), 7.27-7.48 (m, 4H), 7.62 (m, 1H), 8.16 (m, 1H), 8.31 (m, 1H), 9.32 (s, 2H), 9.43 (m, 1H).

Step 2. To [3-({[2-(3-fluoro-phenyl)-pyrimidine-5-carbonyl]-amino}-methyl)-benzyl]-carbamic acid tert-butyl ester (0.28 g, 0.64 mmol) at 0° C. is added HCl in dioxane (6.5 mL, 4 N) and the mixture is stirred for 2.5 hours. The mixture is concentrated in vacuo. The residue is dissolved in DCM (3 mL) and Et$_3$N (0.21 mL, 0.1.5 mmol) and methanesulfonyl chloride (0.105 mL, 0.1.3 mmol) are added. The mixture is stirred for 12 hours, diluted with EtOAc (100 mL), washed with saturated aqueous NH$_4$Cl (2×50 mL), dried with Na$_2$SO$_4$, filtered, and concentrated in vacuo. The residue is purified by flash chromatography eluting with 20%-80% EtOAc/heptane to afford 2-(3-fluoro-phenyl)-pyrimidine-5-carboxylic acid 3-(methanesulfonylamino-methyl)-benzylamide (0.25 g, 94%) as a powder. MS: 459 (M+H); $^1$H NMR (300 MHz, DMSO-d$_6$): δ 2.85 (s, 3H), 4.17 (d, J=6.2 Hz, 2H), 4.56 (d, J=5.9 Hz, 2H), 7.27-7.62 (m, 5H), 8.17 (m, 1H), 8.32 (m, 1H), 9.32 (s, 2H), 9.45 (m, 1H).

Example 73

2-(3-fluoro-phenyl)-pyrimidine-5-carboxylic acid 3-[(propane-2-sulfonylamino)-methyl]-benzylamide

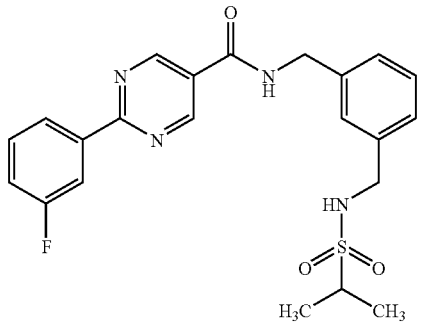

Following procedures similar to those of Example 72 (step 2) but substituting isopropanesulfonyl chloride (1.3 mmol) for methanesulfonyl chloride there is prepared 2-(3-fluoro-phenyl)-4-methyl-pyrimidine-5-carboxylic acid 3-[(propane-2-sulfonylamino)-methyl]-benzylamide (7 mg) as a solid. MS: 443 (M+H); $^1$H NMR (300 MHz, DMSO-d$_6$): δ 1.20 (d, J=6.8 Hz, 6H), 3.05 (m, 1H), 4.17 (d, J=6.4 Hz, 2H), 4.55 (d, J=5.9 Hz, 2H), 7.27-7.62 (m, 5H), 8.17 (m, 1H), 8.32 (m, 1H), 9.32 (s, 2H), 9.45 (m, 1H).

Example 74

2-(3-Fluoro-phenyl)-pyrimidine-5-carboxylic acid 3-methylsulfamoylmethyl-benzylamide

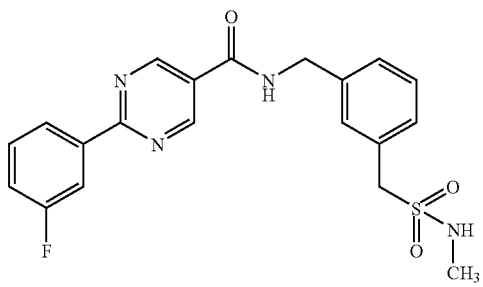

Following procedures similar to those of Example 72 (step 1) but substituting C-(3-aminomethyl-phenyl)-N-methyl-methanesulfonamide (1.17 mmol) for (3-aminomethyl-benzyl)-carbamic acid tert-butyl ester there is prepared 2-(3-fluoro-phenyl)-pyrimidine-5-carboxylic acid 3-methylsulfamoylmethyl-benzylamide (105 mg) as a solid. MS: 415 (M+H); $^1$H NMR (300 MHz, DMSO-d$_6$): δ 2.57 (d, J=4.8 Hz, 3H), 4.32 (s, 2H), 4.57 (d, J=5.9 Hz, 2H), 6.92 (m, 1H), 7.28-7.67 (m, 5H), 8.17 (m, 1H), 8.32 (m, 1H), 9.32 (s, 2H), 9.46 (m, 1H).

Example 75

2-(3-Fluoro-phenyl)-pyrimidine-5-carboxylic acid 3-(isopropylsulfamoyl-methyl)-benzylamide

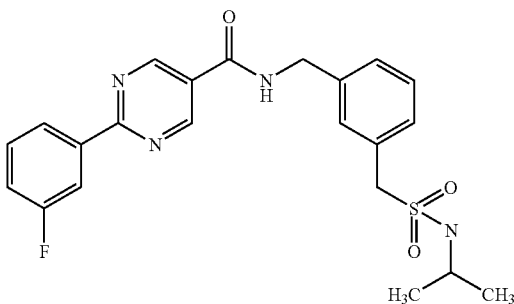

Following procedures similar to those of Example 72 (step 1) but substituting C-(3-aminomethyl-phenyl)-N-isopropyl-methanesulfonamide (1.45 mmol) for (3-aminomethyl-benzyl)-carbamic acid tert-butyl ester there is prepared 2-(3-fluoro-phenyl)-pyrimidine-5-carboxylic acid 3-(isopropylsulfamoyl-methyl)-benzylamide (140 mg) as a solid. MS: 443 (M+H); $^1$H NMR (300 MHz, DMSO-d$_6$): δ 1.07 (d, J=6.4, 6H), 3.39 (m, 1H), 4.29 (s, 2H), 4.56 (d, J=5.9, 2H), 6.99 (d, J=7.1 Hz, 1H), 7.28-7.45 (m, 3H), 7.62 (m, 1H), 8.17 (m, 1H), 8.32 (m, 1H), 9.32 (s, 2H), 9.45 (m, 1H).

Example 76

2-(3-Fluoro-phenyl)-pyrimidine-5-carboxylic acid (2-methanesulfonylamino-pyridin-4-ylmethyl)-amide

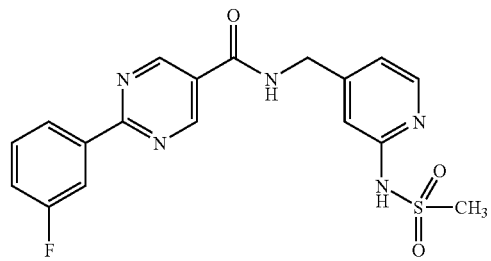

Step 1: A solution of 2-amino-isonicotinonitrile (1 g, 8.4 mmol) and methanesulfonyl chloride (0.716 mL, 9.2 mmol) in pyridine (10 mL) is stirred at room temperature for 12 hours. The mixture is poured onto ice and stirred for 20 min. The mixture is filtered and washed with water (100 mL), followed by diethyl ether (100 mL). The solid is dried in vacuo to afford N-(4-cyanopyridin-2-yl)-methanesulfonamide (1.1 g, 66%). MS: 198 (M+H); $^1$H NMR (300 MHz, DMSO-d$_6$): δ 3.32 (s, 3H), 7.27 (s, 1H), 7.48 (d, J=5.1 Hz, 1H), 8.53 (d, J=5.3 Hz, 1H).

Step 2: N-(4-Cyano-pyridin-2-yl)-methanesulfonamide (0.15 g, 0.76 mmol) is dissolved in MeOH (4 mL) and concentrated HCl (2 mL) and is treated with Pd/C (10%, 150 mg). The mixture is stirred under H$_2$ for 12 hours, filtered and concentrated in vacuo to afford N-(4-aminomethyl-pyridin-2-yl)-methanesulfonamide (0.15 g, 97%), which is used directly in the next step without further purification.

Step 3: Following procedures similar to those of Example 72 (step 1) but substituting N-(4-aminomethyl-pyridin-2-yl)-methanesulfonamide (0.75 mmol) for (3-aminomethyl-benzyl)-carbamic acid tert-butyl ester there is prepared 2-(3-fluoro-phenyl)-pyrimidine-5-carboxylic acid (2-methanesulfonylamino-pyridin-4-ylmethyl)-amide (320 mg) as a solid. MS: 402 (M+H); $^1$H NMR (300 MHz, DMSO-d$_6$): δ 3.24 (s, 3H), 4.53 (d, J=5.7 Hz, 2H), 6.97 (s, br, 2H), 7.43 (m, 1H), 7.63 (m, 1H), 8.18 (m, 2H), 8.33 (m, 1H), 9.33 (s, 2H), 9.52 (m, 1H).

Example 77

2-(5-Methyl-[1,2,4]oxadiazole-3-yl)-pyrimidine-5-carboxylic acid (tetrahydro-pyran-4-yl)-amide,

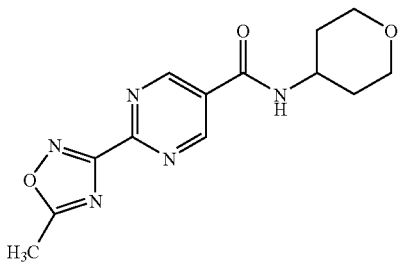

Step 1. To a solution of 2-methylsulfanyl-pyrimidine-5-carboxylic acid methyl ester 1 (1 g, 5.43 mmol) in DCM (60 mL) is added MCPBA (2.81 g, 16.29 mmol) portion wise at room temperature. The resulting solution is stirred at room temperature overnight. A solution of Na$_2$S$_2$O$_3$ (1.6 g) in water (60 mL) is added. The mixture is stirred at room temperature for 20 min. The layer is separated, and the water layer is extracted with DCM (2×20 mL). The combined DCM layer is washed with saturated NaHCO$_3$ (3×20 mL), dried (Na$_2$SO$_4$), filtered and concentrated in vacuo to afford 2-methanesulfonyl-pyrimidine-5-carboxylic acid methyl ester as a solid (1.05 g, 90%). MS: 217 (M+H); $^1$H NMR (300 MHz, CDCl$_3$): δ 3.41 (s, 3H), 4.06 (s, 3H), 9.44 (s, 2H).

Step 2. To a solution of 2-methanesulfonyl-pyrimidine-5-carboxylic acid methyl ester 2 (2.5 g, 11.56 mmol) in DCM (30 mL) is added a solution of tetrabutylammonium cyanide (3.1 g, 11.56 mmol) in water (30 mL) slowly at room temperature. The mixture is stirred for 80 min. The mixture is washed with water (2×20 mL), dried (Na$_2$SO$_4$), filtered and concentrated in vacuo. The residue is purified by column chromatography eluting with 5-60% EtOAc in heptane to afford 2-cyano-pyrimidine-5-carboxylic acid methyl ester (1.16 g, 61%) as a solid. MS: 164 (M+H); $^1$H NMR (300 MHz, CDCl$_3$): δ 4.05 (s, 3H), 9.37 (s, 2H).

Step 3. To a solution of 2-cyano-pyrimidine-5-carboxylic acid methyl ester 3 (1 g, 6.13 mmol) in MeOH (20 mL) at room temperature is added hydroxylamine hydrochloride (0.64 g, 9.2 mmol) and sodium acetate (0.76 g, 9.2 mmol). The resulting mixture is heated to reflux for 2 hours. The mixture is cooled to room temperature and concentrated in vacuo. Water (30 mL) is added to the residue, and the solid is filtered, and washed with water twice. The solid is dried in vacuum oven overnight to afford 2-(N-hydroxycarbamimidoyl)-pyrimidine-5-carboxylic acid methyl ester (1.09 g, 91%) as a solid. MS: 197 (M+H).

Step 4. To a solution of 2-(N-hydroxycarbamimidoyl)-pyrimidine-5-carboxylic acid methyl ester (900 mg, 4.59 mmol) in pyridine (15 mL) is added acetyl chloride (432 mg, 5.5 mmol) dropwise. The resulting solution is stirred at room temperature for 1 hour, and heated to reflux for 3 h. The solution is cooled to room temperature and concentrated in vacuo. Water (30 mL) is added to the residue, and the mixture is extracted with EtOAc (3×20 mL). The combined organic layer is washed with saturated NaHCO$_3$, dried (Na$_2$SO$_4$), filtered and concentrated in vacuo to afford 2-(5-methyl-[1,2,3]oxadiazo-3-yl)-pyrimidine-5-carboxylic acid methyl ester (900 mg, 89%) as a solid. MS: 221 (M+H).

Step 5. To a solution of 2-(5-methyl-[1,2,3]oxadiazo-3-yl)-pyrimidine-5-carboxylic acid methyl ester (900 mg) in MeOH (20 mL) is added a solution of LiOH (100 mg) in water (20 mL) at 0° C. The ice-bath is removed, and the mixture is stirred for another 10 min. The solvent is evaporated, and water (20 mL) is added. The water solution is washed with ether (2×20 mL), and acidified with 2 N HCl to pH ~3. The resulting precipitate is filtered, washed with water and dried in vacuum oven overnight to afford 2-(5-methyl-[1,2,4]oxadiazol-3-yl)-pyrimidine-5-carboxylic acid (350 mg, 37%) as a solid. MS: 207 (M+H); $^1$H NMR (300 MHz, DMSO-d$_6$): δ 2.73 (s, 3H), 9.39 (s, 2H).

Step 6. To a solution of 2-(5-methyl-[1,2,4]oxadiazol-3-yl)-pyrimidine-5-carboxylic acid (50 mg, 0.24 mmol) in DCM (10 mL) is added 1-[3-(dimethylamino)propyl-3-ethylcarbodiimide (50 mg, 0.26 mmol) and N-hydroxybenzotriazole (35 mg, 0.26 mmol) at room temperature. The mixture is stirred for 10 min, and tetrahydro-pyran-4-ylamine (27 mg, 0.26 mmol) is added. The mixture is stirred overnight, washed with 2N HCl (1×5 mL), saturated NaHCO$_3$, (1×5 mL), water (lx 5 mL), dried (Na$_2$SO$_4$), filtered and concentrated in vacuo. The residue is purified by column chromatography eluting with 5% MeOH in DCM to afford 2-(5-methyl-[1,2,4]oxadiazole-3-yl)-pyrimidine-5-carboxylic acid (tetrahydro-pyran-4-yl)-amide (33 mg) as a solid. MS: 290 (M+H); $^1$H NMR (300 MHz, CDCl$_3$): δ 1.70 (m, 2H), 2.04 (m, 2H), 2.76 (s, 3H), 3.59 (m, 2H), 4.06 (m, 2H), 4.28 (m, 1H), 9.26 (s, 2H); IC$_{50}$=513.5 nM.

Example 78

2-(5-Methyl-[1,2,4]oxadiazole-3-yl)-pyrimidine-5-carboxylic acid 4-sulfamoyl-benzeneamide

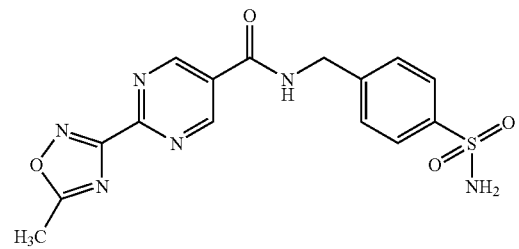

Following procedures similar to those of Example 77 (step 6) but substituting 4-aminomethyl-benzenesulfonamide for tetrahydro-pyran-4-ylamine there is prepared 2-(5-methyl-[1,2,4]oxadiazole-3-yl)-pyrimidine-5-carboxylic acid 4-sulfamoyl-benzeneamide as a solid. MS: 375 (M+H); $^1$H NMR (300 MHz, DMSO-d$_6$): δ 2.72 (s, 3H), 4.61 (d, 2H), 7.33 (s, 2H), 7.56 (d, 2H), 7.80 (d, 2H), 9.39 (s, 2H).

Example 79

2-(5-Methyl-[1,2,4]oxadiazol-3-yl)-pyrimidine-5-carboxylic acid (3-phenyl-[1,2,4]thiadiazol-5-yl)-amide

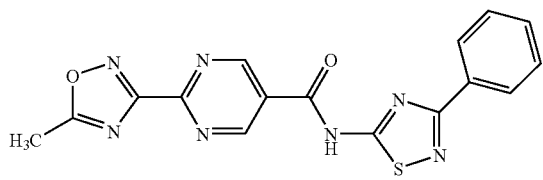

Following procedures similar to those of Example 77 (step 6) but substituting 3-phenyl-[1,2,4]thiadiazol-5-ylamine for tetrahydro-pyran-4-ylamine there is prepared 2-(5-methyl-[1,2,4]oxadiazol-3-yl)-pyrimidine-5-carboxylic acid (3-phenyl-[1,2,4]thiadiazol-5-yl)-amide as a solid. MS: 366 (M+H); $^1$H NMR (300 MHz, DMSO-d$_6$): δ 2.74 (s, 3H), 7.56 (m, 3H), 8.24 (m, 2H), 9.63 (s, 2H).

Example 80

2-(3-Fluoro-phenyl)-pyrimidine-5-carboxylic acid 3-(morpholine-4-sulfonyl)-benzylamide

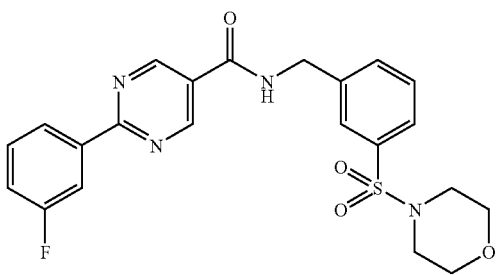

Following procedures similar to those of Example 5 but substituting 3-(morpholinosulfonyl)-benzylamine for aniline, there is prepared 2-(3-fluoro-phenyl)-pyrimidine-5-carboxylic acid 3-(morpholine-4-sulfonyl)-benzylamide as a solid. MS: 457 (M+H); $^1$H NMR (300 MHz, CDCl$_3$): δ 2.88-3.10 (m, 4H), 3.65-3.85 (m, 4H), 4.78 (d, 2H), 6.88-7.05 (bs, N—H), 7.18-7.35 (m, H), 7.40-7.60 (m, 2H), 7.60-7.80 (m, 3H), 8.10-8.35 (q, 4H), 9.21 (s, 2H).

Example 81

2-Pheny-pyrimidine-5-carboxylic acid 3,4-dimethoxyl-benzylamide

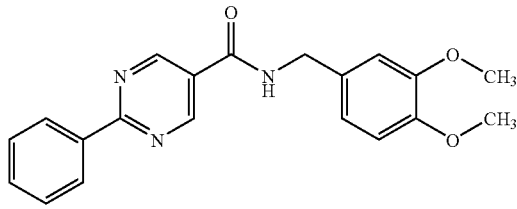

Following procedures similar to those of Example 8 but substituting 3,4-dimethoxyl-benzylamine (0.3 mmol) for 2,2-dioxo-2,3-dihydro-1H-2lamda*6*-benzo[c]isothiazol-5-ylamine, there is prepared 2-phenyl-pyrimidine-5-carboxylic acid 3,4-dimethoxyl-benzylamide as a solid. MS: 350 (M+H).

Example 82

2-Phenyl-pyrimidine-5-carboxylic acid (2-benzo[133]dioxol-5-yl-ethyl)-amide

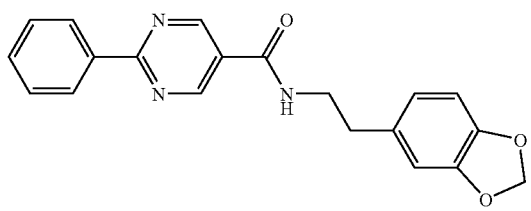

Following procedures similar to those of Example 8 but substituting 2-benzo[1,3]dioxol-5-yl-ethylamine hydrochloride (0.3 mmol) for 2,2-dioxo-2,3-dihydro-1H-2lamda*6*-benzo[c]isothiazol-5-ylamine, there is prepared 2-phenyl-pyrimidine-5-carboxylic acid (2-benzo[1,3]dioxol-5-yl-ethyl)-amide as a solid. MS: 348 (M+H); $^1$H NMR (300 MHz, CDCl$_3$): δ 2.91 (t, 2H), 3.74 (m, 2H), 5.98 (s, 2H), 6.20 (bs, N—H), 6.65-6.83 (m, 3H), 7.54 (m, 3H), 8.49 (m, 2H), 9.08 (s, 2H); IC$_{50}$=2 nM.

Example 83

2-Pheny-pyrimidine-5-carboxylic acid (1H-indazol-5-yl)-amide

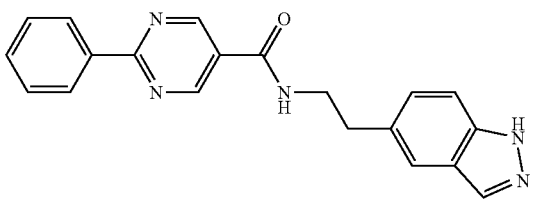

Following procedures similar to those of Example 8 but substituting 1H-indazol-5-amine (0.3 mmol) for 2,2-dioxo-2,3-dihydro-1H-2lamda*6*-benzo[c]isothiazol-5-ylamine, there is prepared 2-phenyl-pyrimidine-5-carboxylic acid (1H-indazol-5-yl)-amide as a solid. MS: 316 (M+H); $^1$H NMR (300 MHz, CDCl$_3$): δ 6.99 (d, H), 7.06 (q, H), 7.52-7.63 (m, 4H), 8.10 (s, H), 8.38 (d, H), 8.57 (m, 3H), 9.53 (s, H); IC$_{50}$=23 nM.

Example 84

2-Phenyl-pyrimidine-5-carboxylic acid 4-[1,2,3]thiadiazol-5-yl)-benzylamide

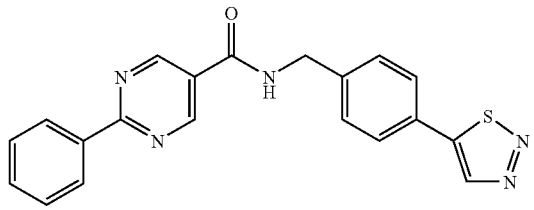

Following procedures similar to those of Example 8 but substituting 4-[1,2,3]thiadiazol-5-yl-benzylamine (0.3 mmol) for 2,2-dioxo-2,3-dihydro-1H-2lamda*6*-benzo[c]isothiazol-5-ylamine, there is prepared 2-phenyl-pyrimidine-5-carboxylic acid 4-[1,2,3]thiadiazol-5-yl)-benzylamide as a solid. MS: 374 (M+H); $^1$H NMR (300 MHz, DMSO-d$_6$): δ 4.25 (d, 2H), 7.52-7.60 (m, 5H), 8.12 (d, 2H), 8.45 (m, 2H), 9.31 (s, 2H), 9.46 (bs, N—H), 9.59 (s, H); IC$_{50}$=6.5 nM.

Example 85

2-(3-Fluoro-phenyl)-4-methyl-pyrimidine-5-carboxylic acid 3-methylsulfamoyl-benzylamide

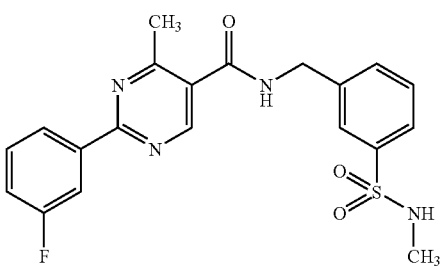

Following procedures similar to those of Example 5, but substituting 2-(3-fluoro-phenyl)-4-methyl-pyrimidine-5-carboxylic acid for 2-(3-fluoro-phenyl)-pyrimidine-5-carboxylic acid, and substituting 3-aminomethyl-N-methyl-benzenesulfonamide hydrochloride for aniline, there is prepared 2-(3-fluoro-phenyl)-4-methyl-pyrimidine-5-carboxylic acid 3-methylsulfamoyl-benzylamide as a solid. MS: 415 (M+H); $^1$H NMR (300 MHz, CDCl$_3$): δ 2.73 (s, 3H), 4.72 (d, 2H), 6.70 (bs, N—H), 7.15-7.26 (m, H), 7.41-7.65 (m, 3H), 7.77 (d, H), 7.85 (s, N—H), 8.15 (d, H), 8.24 (d, H), 9.76 (s, H). IC$_{50}$=106 nM.

Example 86

4-Methyl-2-pyridin-2-yl-pyrimidine-5-carboxylic acid 3-methylsulfamoyl-benzylamide

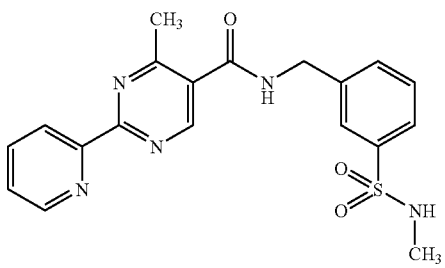

Following procedures similar to those of Example 5 but substituting 4-methyl-2-pyridin-2-yl-pyrimidine-5-carboxylic acid for 2-(3-fluoro-phenyl)-pyrimidine-5-carboxylic acid, and substituting 3-aminomethyl-N-methyl-benzenesulfonamide for aniline, there is prepared 4-methyl-2-pyridin-2-yl-pyrimidine-5-carboxylic acid 3-methylsulfamoyl-benzylamide as a solid. MS: 398 (M+H); $^1$H NMR (300 MHz, CDCl$_3$): δ 2.54 (s, 3H), 2.59 (s, 3H), 4.62 (d, 2H), 7.23-7.42 (m, 3H), 7.48-7.60 (m, H), 7.61-7.68 (d, H), 7.78-7.93 (m, 2H), 8.37-8.44 (d, H), 8.51-8.62 (m, H), 8.67 (s, H).

Example 87

2-Pheny-pyrimidine-5-carboxylic acid 4-morpholin-4-ylbenzylamide

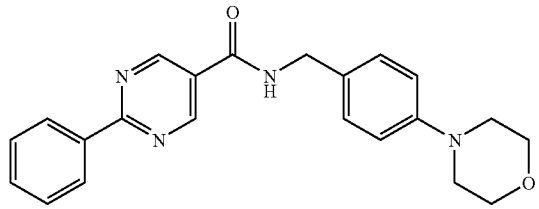

Following procedures similar to those of Example 8 but substituting 4-morpholin-4-yl-benzylamine for 2,2-dioxo-2,3-dihydro-1H-2lamda*6*-benzo[c]isothiazol-5-ylamine, there is prepared 2-phenyl-pyrimidine-5-carboxylic acid 4-morpholin-4-ylbenzylamide as a solid. MS: 375 (M+H); $^1$H NMR (300 MHz, CDCl$_3$): δ 3.18 (t, 4H), 3.88 (t, 4H), 4.62 (d, 2H), 6.48 (bs, N—H), 6.92 (m, 2H), 7.29 (m, 2H), 7.47-7.58 (m, 3H), 8.50 (m, 2H), 9.16 (s, 2H); IC$_{50}$=12 nM.

Example 88

6-[(2-Phenyl-pyrimidin-5-carbonyl)-amino]-1H-benzoimidazole-2-carboxylic acid methyl ester

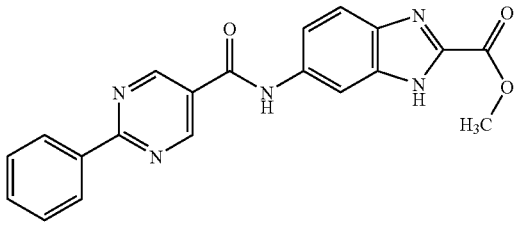

Following procedures similar to those of Example 8 but substituting 6-amino-1H-benzoimidazole-2-carboxylic acid methyl ester for 2,2-dioxo-2,3-dihydro-1H-2lamda*6*-benzo[c]isothiazol-5-ylamine, there is prepared 6-[(2-phenyl-pyrimidin-5-carbonyl)-amino]-1H-benzoimidazole-2-carboxylic acid methyl ester as a solid. MS: 374 (M+H); $^1$H NMR (300 MHz, DMSO-d$_6$): δ 3.95 (s, 3H), 7.52-7.63 (m, 5H), 7.70-7.82 (m, H), 8.29 (s, H), 9.38 (s, 2H), 10.68 (d, H).

Example 89

6-[(2-Phenyl-pyrimidin-5-carbonyl)-amino]-1H-benzoimidazole-2-carboxylic acid

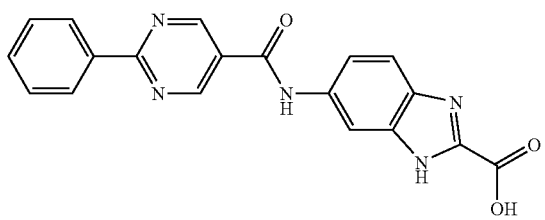

A solution of 6-[(2-phenyl-pyrimidin-5-carbonyl)-amino]-1H-benzoimidazole-2-carboxylic acid methyl ester (0.44 mmol) and LiOH (4.40 mmol) in MeOH/water/tetrahydrofuran (1:1:1, 60 mL) is stirred at room temperature overnight. MeOH and THF are evaporated in vacuo and the aqueous mixture is acidified with 5% HCl to pH ~2. The resulting precipitate is filtered, washed with water (10 mL) and dried to give 6-[(2-phenyl-pyrimidin-5-carbonyl)-amino]-1H-benzoimidazole-2-carboxylic acid as a solid (115 mg). MS: 360 (M+H); $^1$H NMR (300 MHz, DMSO-d$_6$): δ 7.52-7.70 (m, 5H), 8.30 (s, H), 8.48 (m, 3H), 9.28 (S, H), 9.38 (s, 2H), 10.73 (s, N—H).

Example 90

2-Pheny-pyrimidine-5-carboxylic acid (benzofuran-5-ylmethyl)-amide

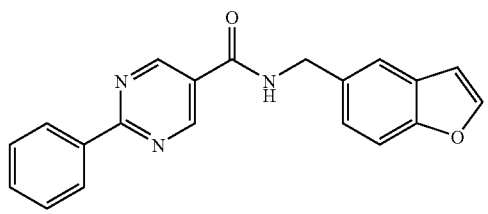

Following procedures similar to those of Example 5 but substituting 2-phenyl-pyrimidine-5-carboxylic acid for 2-(3-fluoro-phenyl)-pyrimidine-5-carboxylic acid, and substituting C-benzofuran-5-ylmethylamine for aniline, there is prepared 2-phenyl-pyrimidine-5-carboxylic acid (benzofuran-5-ylmethyl)-amide as a solid. MS: 330 (M+H); $^1$H NMR (300 MHz, CDCl$_3$): δ 4.79 (d, 2H), 6.58 (bs, N—H), 6.78 (m, H), 7.32 (q, H), 7.49-7.56 (m, 4H), 7.64 (s, H), 7.66 (d, 2H), 8.48 (m, 2H), 9.18 (s, 2H); IC$_{50}$=7 nM.

Example 91

2-Pheny-pyrimidine-5-carboxylic acid 4-methanesulfonylamino-benzylamide

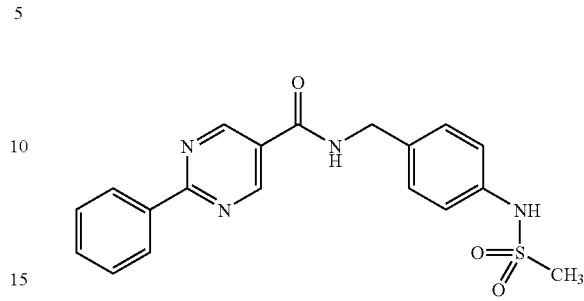

Following procedures similar to those of Example 5 but substituting 2-phenyl-pyrimidine-5-carboxylic acid for 2-(3-fluoro-phenyl)-pyrimidine-5-carboxylic acid, and substituting N-(4-aminomethyl-phenyl)-methanesulfonamide for aniline, there is prepared 2-phenyl-pyrimidine-5-carboxylic acid 4-methanesulfonylamino-benzylamide as a solid. MS: 383 (M+H); $^1$H NMR (300 MHz, DMSO-d$_6$): δ 2.96 (s, 3H), 4.89 (d, 2H), 7.18 (d, 2H), 7.33 (d, 2H), 7.51-7.63 (m, 3H), 78.43 (m, 2H), 8.27 (s, 2H), 9.36 (bs, N—H).

Example 92

2-Pheny-pyrimidine-5-carboxylic acid 4-carbamoyl-benzylamide

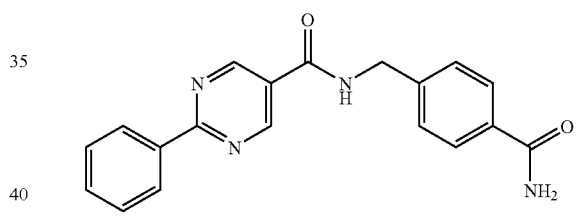

Following procedures similar to those of Example 5 but substituting 2-phenyl-pyrimidine-5-carboxylic acid for 2-(3-fluoro-phenyl)-pyrimidine-5-carboxylic acid, and substituting 4-aminomethyl-benzamide for aniline there is prepared 2-phenyl-pyrimidine-5-carboxylic acid 4-carbamoyl-benzylamide as a solid. MS: 333 (M+H); $^1$H NMR (300 MHz, DMSO-d$_6$): δ 4.59 (d, 2H), 7.32 (s, N—H), 7.43 (d, 2H), 7.50-7.63 (m, 4H), 7.85 (d, 2H), 7.94 (s, H), 8.47 (m, 2H), 9.37 (s 2H), 9.43 (t, N—H); IC$_{50}$=16 nM.

Example 93

2-Pheny-pyrimidine-5-carboxylic acid 3-(2-hydroxy-ethylsulfamoyl)-benzylamide

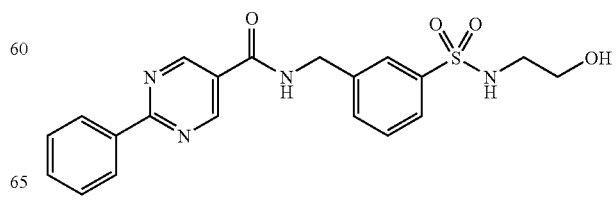

Following procedures similar to those of Example 5 but substituting 2-phenyl-pyrimidine-5-carboxylic acid for 2-(3-fluoro-phenyl)-pyrimidine-5-carboxylic acid, and substituting 3-aminomethyl-N-(2-hydroxy-ethyl)-benzenesulfonamide hydrochloride for aniline, there is prepared 2-phenyl-pyrimidine-5-carboxylic acid 3-(2-hydroxy-ethylsulfamoyl)-benzylamide as a solid. MS: 413 (M+H); $^1$H NMR (300 MHz, CD$_3$OD): δ 2.96 (t, 2H), 3.53 (t, 2H), 4.78 (d, 2H), 7.42-7.91 (m, 9H), 8.46 (m, 2H), 9.22 (s, 2H), 9.40 (bs, N—H).

Example 94

2-Pheny-pyrimidine-5-carboxylic acid 4-(morpholin-4-sulfonyl)-benzylamide

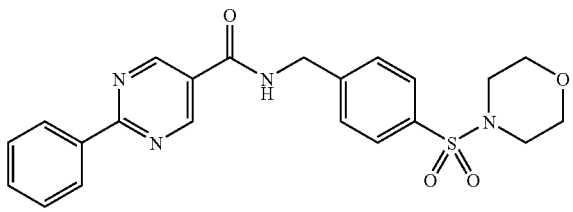

Following procedures similar to those of Example 5 but substituting 2-phenyl-pyrimidine-5-carboxylic acid (0.35 mmol) for 2-(3-fluoro-phenyl)-pyrimidine-5-carboxylic acid, and substituting 4-(morpholin-4-sulfonyl)-benzylamine hydrochloride for aniline, there is prepared 2-phenyl-pyrimidine-5-carboxylic acid 4-(morpholin-4-sulfonyl)-benzylamide as a solid. MS: 439 (M+H); $^1$H NMR (300 MHz, CD$_3$OD): δ 2.96 (t, 4H), 3.70 (t, 4H), 4.73 (s, 2H), 7.53 (m, 3H), 7.65 (d, 2H), 7.77 (d, 2H), 8.49 (d, 2H), 9.26 (s, 2H).

Example 95

2-Pheny-pyrimidine-5-carboxylic acid 3-methylsulfamoyl-benzylamide

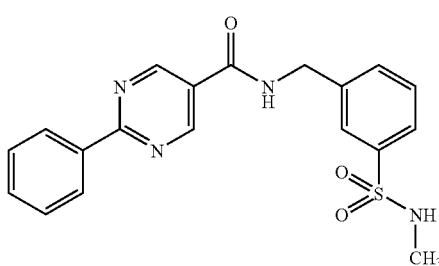

Following procedures similar to those of Example 5 but substituting 2-phenyl-pyrimidine-5-carboxylic acid for 2-(3-fluoro-phenyl)-pyrimidine-5-carboxylic acid, and substituting 3-aminomethyl-N-methyl-benzenesulfonamide hydrochloride for aniline, there is prepared 2-phenyl-pyrimidine-5-carboxylic acid 3-methylsulfamoyl-benzylamide as a solid. MS: 383 (M+H); $^1$H NMR (300 MHz, CD$_3$OD): δ 2.53 (s, 3H), 4.71 (s, 2H), 7.26 (m, H), 7.46-7.80 (m, 7H), 7.87 (s, H), 8.49 (m, 2H), 9.24 (s, 2H).

Example 96

2-Pheny-pyrimidine-5-carboxylic acid [2-(2-amino-4-methyl-thiazol-5-yl)-ethyl]-amide

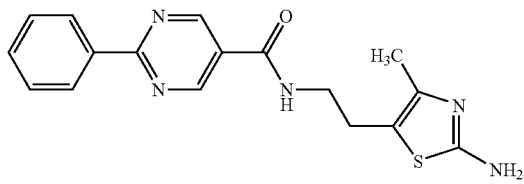

Following procedures similar to those of Example 5 but substituting 2-phenyl-pyrimidine-5-carboxylic acid (0.12 mmol) for 2-(3-fluoro-phenyl)-pyrimidine-5-carboxylic acid, and substituting 5-(2-amino-ethyl-thiazol-2-ylamine dihydrobromide for aniline, there is prepared 2-phenyl-pyrimidine-5-carboxylic acid [2-(2-amino-4-methyl-thiazol-5-yl)-ethyl]-amide as a solid. MS: 340 (M+H); $^1$H NMR (300 MHz, CDCl$_3$): δ 2.11 (s, 3H), 2.92 (t, 2H), 3.61 (q, 2H), 6.70 (bs, N—H), 7.40-7.58 (m, 3H), 8.37-8.54 (m, 2H), 9.12 (s, 2H).

Example 97

2-(3-Fluoro-phenyl)-pyrimidine-5-carboxylic acid 3-methylsulfamoyl-benzylamide

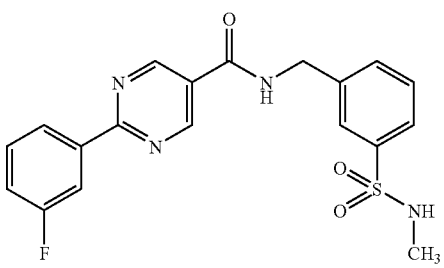

Step 1: A flask containing DCM (90 mL) and methylamine in water (40 wt %, 7.5 mmol) is chilled in an ice water bath with magnetic stirring. 3-Cyano-benzenesulfonyl chloride (5 g, 2.49 mmol) is added along with DCM (10 mL) to wash down the sides of the flask. After 30 min, concentrated HCl in water is added at 0° C., until the reaction is acidic (pH<4). Water (50 mL) is added and DCM is removed in vacuo. The residue is filtered to afford 3-cyano-N-methyl-benzenesulfonamide as a solid (99%). MS: 195 (M+H); $^1$H NMR (300 MHz, CDCl$_3$): δ 2.76 (d, 3H), 4.48 (broad-s, N—H), 7.7 (t, 1H), 7.9 (d, 1H), 8.13 (d, 1H), 8.19 (s, 1H).

Step 2: To a solution of 3-cyano-N-methyl-benzenesulfonamide (4.88 g, 2.49 mmol) in MeOH (160 mL) is added concentrated HCl in water (16 mL) followed by the addition of Palladium on Carbon (10 wt %, 50 wt % water, 1.6 g). With magnetic stirring, the reaction is alternately placed under vacuum and 1 atmosphere of hydrogen (balloon) for three cycles. The reaction is then left under 1 atmosphere of hydrogen with stirring for 2 days. The reaction is filtered through celite and fresh Palladium on Carbon (10 wt %, 50 wt % water, 1.6 g) is added. The reaction is stirred for 24 hours under 1 atmosphere of hydrogen. The reaction is filtered through celite and the filtrate is concentrated in vacuo to provide 3-aminomethyl-N-methyl-benzenesulfonamide hydrochloride, as a solid (99%). MS: 201 (M+H); $^1$H NMR (300 MHz, DMSO-d$_6$): δ 2.41 (d, 3H), 4.12 (d, 2H), 7.23-7.57 (m, 2H), 7.70 (d, 1H), 7.81 (d, 1H), 8.49 (broad-s, 3H).

Step 3: To a mixture of 2-(3-fluoro-phenyl)-pyrimidine-5-carboxylic acid (545 mg, 2.5 mmol) and DCM (35 mL) is added oxalyl chloride (635 mg, 5 mmol) followed by the addition of DMF (20 μL). The reaction is stirred at room temperature for 3 hours. Anhydrous toluene (10 mL) is added and the reaction mixture is concentrated in vacuo. The residue is dissolved in EtOAc (30 mL). The resulting solution is added to a mixture of 3-aminomethyl-N-methyl-benzenesulfonamide hydrochloride (590 mg, 2.5 mmol), sodium carbonate (530 mg, 5 mmol) and water (10 mL) at 0° C. The resulting reaction mixture is warmed to room temperature and stirred overnight. Approximately 80% of EtOAc is removed in vacuo, and heptane is added to precipitate the product. The precipitate is collected by filteration, and recrystallized twice in EtOAc to afford 2-(3-fluoro-phenyl)-pyrimidine-5-carboxylic acid 3-methylsulfamoyl-benzylamide (400 mg). The mother liquors are concentrated and the residue is purified by flash chromatography to afford additional 2-(3-fluoro-phenyl)-pyrimidine-5-carboxylic acid 3-methylsulfamoyl-benzylamide (130 mg) as a powder. MS: 401 (M+H); $^1$H NMR (300 MHz, DMSO-d$_6$): δ 2.41 (d, 3H), 4.64 (d, 2H), 7.42-7.50 (m, 2H), 7.57-7.70 (m, 4H), 7.78 (s, 1H), 8.16 (d, 1H), 8.31 (d, 1H), 9.33 (s, 2H), 9.53 (t, 1H). IC$_{50}$=9.5 nM.

Example 98

{4-{[(2-Phenyl-pyrimidine-5-carbonyl)-amino]-benzyl}-phosphonic acid diethyl ester

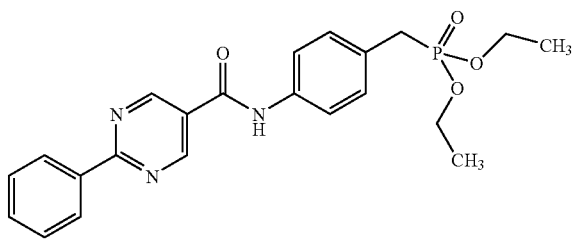

Following procedures similar to those of Example 5 but substituting 2-phenyl-pyrimidine-5-carboxylic acid for 2-(3-fluoro-phenyl)-pyrimidine-5-carboxylic acid, and substituting (4-amino-benzyl)-phosphonic acid diethyl ester for aniline, there is prepared (4-{[(2-phenyl-pyrimidine-5-carbonyl)-amino]-methyl}-benzyl)-phosphonic acid diethyl ester as a solid. MS: 426 (M+H); $^1$H NMR (300 MHz, CDCl$_3$): δ 1.13 (t, 3H), 1.32 (t, 3H), 3.79 (q, H), 3.99 (q, H), 4.20 (m, 2H), 5.91 (q, 4.62 (d, H), 7.27 (d, 3H), 7.48 (s, 3H), 7.67 (d, 2H), 8.42 (d, 2H), 9.28 (s, H), 9.53 (s, H); IC$_{50}$=38 nM.

Example 99

{4-[(2-Phenyl-pyrimidine-5-carbonyl)-amino]-butyl)-phosphonic acid diethyl ester

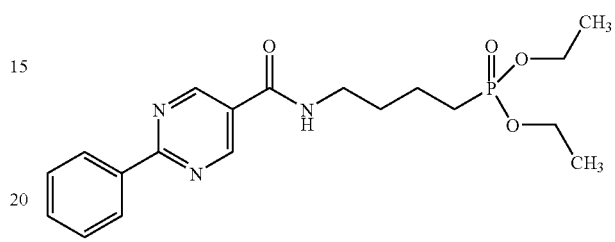

Following procedures similar to those of Example 5 but substituting 2-phenyl-pyrimidine-5-carboxylic acid for 2-(3-fluoro-phenyl)-pyrimidine-5-carboxylic acid, and substituting (4-aminobutyl)-phosphonic acid diethyl ester oxalate for aniline, there is prepared 14-[(2-phenyl-pyrimidine-5-carbonyl)-amino]-butyl)-phosphonic acid diethyl ester as a solid. MS: 392 (M+H); $^1$H NMR (300 MHz, CDCl$_3$): δ 1.31 (t, 6H), 1.77 (m, 6H), 3.48 (q, 2H), 3.97-4.19 (m, 4H), 7.40-7.58 (m, 3H), 7.84 (bs, N—H), 8.40-8.57 (m, 2H), 9.23 (s, 2H); IC$_{50}$=23.5 nM.

Example 100

14-[(2-Phenyl-pyrimidine-5-carbonyl)-amino]-ethyl)-phosphoric acid diethyl ester

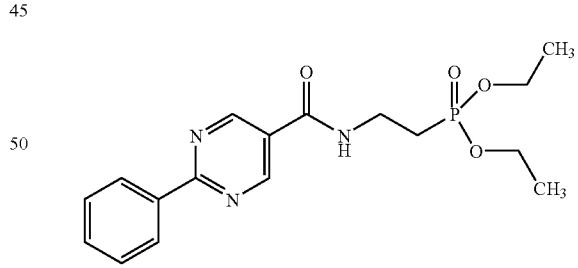

Following procedures similar to those of Example 5 but substituting 2-phenyl-pyrimidine-5-carboxylic acid for 2-(3-fluoro-phenyl)-pyrimidine-5-carboxylic acid, and substituting (4-aminoethyl)-phosphonic acid diethyl ester oxalate for aniline, there is prepared {4-[(2-phenyl-pyrimidine-5-carbonyl)-amino]-ethyl)-phosphonic acid diethyl ester as a solid. MS: 364 (M+H); $^1$H NMR (300 MHz, CDCl$_3$): δ 1.38 (t, 6H), 2.16 (m, 2H), 3.78 (m, 2H), 4.03-4.22 (m, 4H), 7.50 (m, 3H), 8.09 (bs, N—H), 8.48 (m, 2H), 9.24 (s, 2H).

Example 101

{Phenyl-[(2-phenyl-pyrimidine-5-carbonyl)-amino]-methyl)-phosphonic acid diethyl ester

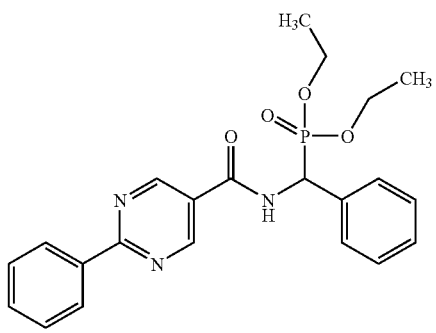

Following procedures similar to those of Example 5 but substituting 2-phenyl-pyrimidine-5-carboxylic acid for 2-(3-fluoro-phenyl)-pyrimidine-5-carboxylic acid, and substituting (amino-phenyl-methyl)-phosphonic acid diethyl ester hydrochloride for aniline, there is prepared {phenyl-[(2-phenyl-pyrimidine-5-carbonyl)-amino]-methyl}-phosphonic acid diethyl ester as a solid. MS: 426 (M+H); $^1$H NMR (300 MHz, CDCl$_3$): δ 1.13 (t, 3H), 1.32 (t, 3H), 3.70-3.90 (m, H), 3.90-4.08 (m, H), 4.09-4.31 (m, 2H), 5.88 (q, H), 7.27 (m, 3H), 7.47 (m, 3H), 7.65 (d, H), 8.43 (m, 2H), 9.27 (s, 2H), 9.35 (d, N—H); IC$_{50}$=48 nM.

Example 102

2-(3-Fluoro-phenyl)-pyrimidine-5-carboxylic acid 3-methanesulfonyl)-benzylamide

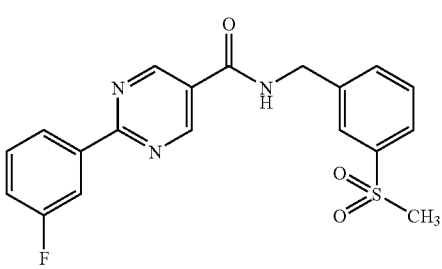

Following procedures similar to those of Example 5 but substituting 3-methanesulfonyl-benzylamine for aniline, there is prepared 2-(3-fluoro-phenyl)-pyrimidine-5-carboxylic acid 3-methanesulfonyl)-benzylamide as a solid. MS: 386 (M+H); $^1$H NMR (300 MHz, CD$_3$OD): δ 3.12 (s, 3H), 4.93 (d, 2H), 7.24-7.37 (m, H), 7.48-7.70 (m, 2H), 7.77 (d, H), 7.88 (d, H), 7.98 (s, H), 8.20 (d, H), 8.34 (d, H), 9.25 (S, 2H).

Example 103

2-(3-Fluoro-phenyl)-pyrimidine-5-carboxylic acid (1-methanesulfonyl-piperidin-3-ylmethyl)amide

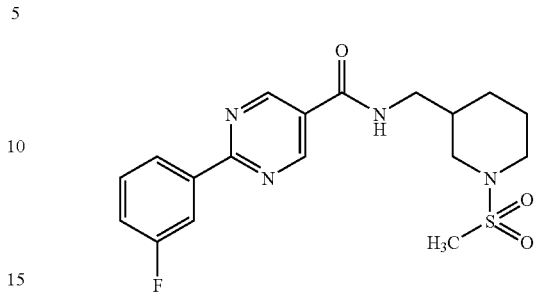

Step 1: To a solution of potassium carbonate (13.94 mmol) and 3-aminomethyl-piperidine-1-carboxylic acid tert-butyl ester (4.65 mmol) in ethyl acetate (30 mL) and water (20 mL) is added a solution of 2-(3-fluoro-phenyl)-pyrimidine-5-carboxylic acid chloride (4.65 mmol) in ethyl acetate (20 mL). The mixture is stirred at room temperature overnight. The reaction mixture is extracted with ethyl acetate, washed with water, dried (Na$_2$SO$_4$) and concentrated in vacuo to give 3-({[2-(3-fluoro-phenyl)-pyrimidine-5-carbonyl]-amino}-methyl)-piperidine-1-carboxylic acid tert-butyl ester as a solid. MS 415 (M+H); $^1$H NMR (300 MHz, CDCl$_3$): δ 1.47 (s, 9H), 1.55-2.22 (m, 5H), 2.90-4.90 (m, 6H), 7.15-7.25 (m, H), 7.41-7.53 (m, H), 7.56 (bs, NH), 8.18 (d, H), 8.29 (d, H), 9.21 (s, 2H).

Step 2: Hydrogen chloride gas is bubbled into a solution of 3-({[2-(3-fluoro-phenyl)-pyrimidine-5-carbonyl]-amino}-methyl)-piperidine-1-carboxylic acid tert-butyl ester (3.76 mmol) in DCM (20 mL) and the reaction is stirred at room temperature for 2 hours. The mixture is concentrated in vacuo to afford 2-(3-fluoro-phenyl)-pyrimidine-5-carboxylic acid (piperidin-3-ylmethyl)-amide hydrochloride as a solid. MS 415 (M+H); $^1$H NMR (300 MHz, CD$_3$OD): δ 1.22-1.50 (m, 2H), 1.68-1.90 (m, H), 1.90-2.06 (bs, 2H), 2.06-2.17 (bs, 6H), 2.73-3.04 (m, 2H), 3.24-3.50 (m, H), 7.24-7.35 (m, H), 7.48-7.60 (m, H), 8.19 (d, H), 8.34 (d, H), 9.23 (s, 2H).

Step 3: Methanesulfonyl chloride (0.523 mmol) is added to a stirred solution of 2-(3-fluoro-phenyl)-pyrimidine-5-carboxylic acid (piperidin-3-ylmethyl)-amide hydrochloride (0.523 mmol) and triethylamine (2.62 mmol) in DCM (20 mL) at 0° C. The mixture is stirred at 0° C. for an hour, and then stirred at room temperature overnight. The reaction mixture is washed with water (20 mL). The organic layer is separated, dried (MgSO$_4$), filtered and concentrated in vacuo. The residue is purified by silica gel column chromatography eluting with EtOAc to afford 2-(3-fluoro-phenyl)-pyrimidine-5-carboxylic acid (1-methanesulfonyl-piperidin-3-ylmethyl)-amide as a solid. MS: 393 (M+H); $^1$H NMR (300 MHz, CD$_3$OD): δ 1.43-1.95 (m, 4H), 2.10-2.23 bs, H), 3.04-3.50 (m, 5H), 3.60-3.78 (m, H), 6.71-6.90 (bs, N—H), 7.18-7.23 (m, H), 7.42-7.57 (m, H), 8.18-8.37 (q, 2H), 9.20 (s, 2H).

Example 104

2-(3-Fluoro-phenyl)-pyrimidine-5-carboxylic acid (1-dimethanesulfamoyl-piperidin-3-ylmethyl)-amide

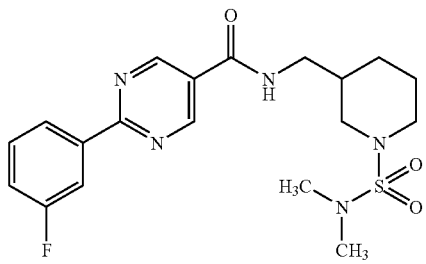

Dimethanesulfamoyl chloride (0.632 mmol) is added to a stirred solution of 2-(3-fluoro-phenyl)-pyrimidine-5-carboxylic acid (piperidin-3-ylmethyl)-amide trihydrochloride (0.632 mmol) and triethylamine (3.16 mmol) in DCM (20 mL) at 0° C. The mixture is stirred at 0° C. for an hour, and then stirred at room temperature overnight. The reaction mixture is diluted with DCM (10 mL) and washed with water (30 mL). The organic layer is separated, dried (Na₂SO₄), filtered and concentrated in vacuo. The residue is triturated with EtOAc to afford 2-(3-fluoro-phenyl)-pyrimidine-5-carboxylic acid (1-dimethanesulfamoyl-piperidin-3-ylmethyl)-amide (245 mg) as a solid. MS: 422 (M+H); ¹H NMR (300 MHz, CDCl₃): δ 1.37-1.69 (m, 2H), 1.74-1.92 (m, 2H), 2.03-2.17 (bs, H), 2.81 (s, 6H), 3.09-3.20 (m, H), 3.21-3.50 (m, 4H), 3.60-3.75 (m, H), 6.83-6.98 (bs, N—H), 7.16-7.28 (m, H), 7.42-7.55 (m, H), 8.16-8.33 (q, 2H), 9.20 (s, 2H).

Example 105

2-(Phenyl)-pyrimidine-5-carboxylic acid 3-methanesulfonylamino-benzylamide

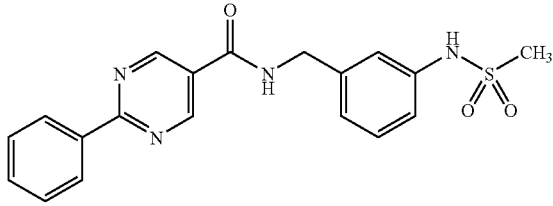

Methanesulfonyl chloride (0.553 mmol) is added to a stirred solution of 2-phenyl-pyrimidine-5-carboxylic acid 3-amino-benzylamide (Example 115, 0.526 mmol) and triethylamine (1.05 mmol) in DCM (20 mL) at 0° C. The mixture is stirred at room temperature for an hour. The reaction mixture is quenched with 5% HCl and extracted with DCM (20 mL). The organic layer is separated, washed with water (20 mL) and brine (20 mL), dried (Na₂SO₄), filtered and concentrated in vacuo. The residue is purified by silica gel column chromatography eluting with 0-5% MeOH in DCM to afford 2-(phenyl)-pyrimidine-5-carboxylic acid 3-methanesulfonylamino-benzylamide (200 mg) as a solid. MS: 383 (M+H); ¹H NMR (300 MHz, CDCl₃): δ 3.41 (s, 3H), 4.76-4.72 (m, 2H), 7.00 (bs, N—H), 7.05-7.23 (m, 2H), 7.27-7.60 (m, 5H), 8.40-8.53 (m, 2H), 9.16 (s, 2H).

Example 106

2-(3-Fluoro-phenyl)-pyrimidine-5-carboxylic acid 3-acetylsulfamoyl-benzylamide

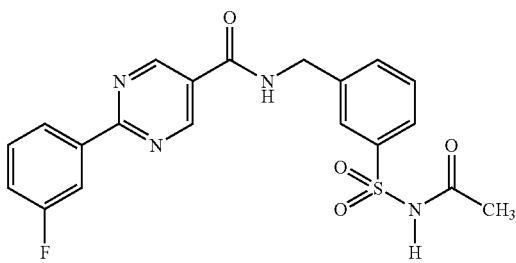

To a solution of potassium carbonate (1.22 mmol) and N-acetyl-3-aminomethyl-benzenesulfonamide (1.22 mmol) in EtOAc (10 mL) and water (10 mL) is added a solution of 2-(3-fluoro-phenyl)-pyrimidine-5-carboxylic acid chloride (1.22 mmol) in acetate (10 mL) at 0° C., and the mixture is stirred at room temperature overnight. The mixture is acidified with 5% HCl to pH ~2-3 and extracted with EtOAc. The organic layer is separated, washed with water and brine, dried (MgSO₄), filtered and concentrated in vacuo. The residue is purified by silica gel column chromatography eluting with EtOAc to afford 2-(3-fluoro-phenyl)-pyrimidine-5-carboxylic acid 3-acetylsulfamoyl-benzylamide as a solid. MS: 429 (M+H); ¹H NMR (300 MHz, CD₃OD): δ 3.95-4.00 (d, 3H), 4.85 (s, 3H), 7.22-7.34 (m, H), 7.41-7.62 (m, H), 7.66-7.83 (d, 2H), 7.88-7.95 (d, H), 8.04 (s, H), 8.12-8.23 (m, H), 8.26-8.37 (d, H), 9.26-9.34 (m, 2H).

Example 107

2-(3-Fluoro-phenyl)-pyrimidine-5-carboxylic acid 3-(3-oxo-piperazine-1-sulfonyl)-benzylamide

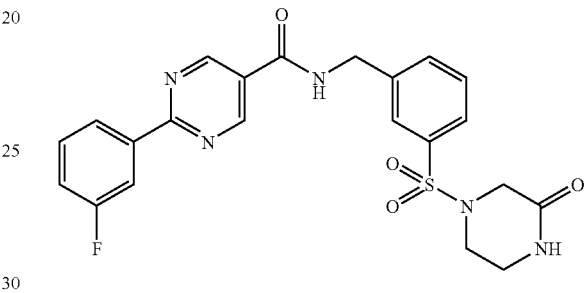

Following procedures similar to those of Example 106, but substituting 4-(3-aminomethyl-benzenesulfonyl)-piperazin-2-one for N-acetyl-3-aminomethyl-benzenesulfonamide, there is prepared 2-(3-fluoro-phenyl)-pyrimidine-5-carboxylic acid 3-(3-oxo-piperazine-1-sulfonyl)-benzylamide as a solid. MS: 470 (M+H); ¹H NMR (300 MHz, DMSO-d₆): δ 3.16 (s, 4H), 3.57 (s, 2H), 4.63 (d, 2H), 7.34-7.47 (m, H), 7.56-7.77 (m, 4H), 7.80 (s, N—H), 8.01-8.18 (m, 2H), 8.28 (d, H), 9.29 (S, 2H), 9.45 (t, N—H).

Example 108

2-Pheny-pyrimidine-5-carboxylic acid (2-sulfamoyl-ethyl)-amide

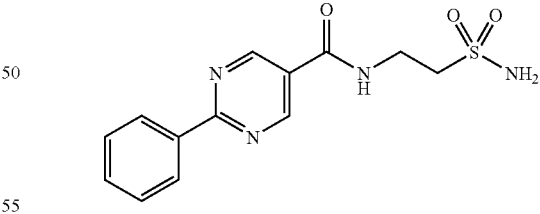

To a solution of 2-phenyl-pyrimidine-5-carboxylic acid chloride (1.51 mmol) and 2-amino-ethanesulfonic acid amide (1.51 mmol) in DCM (15 mL) is added diisopropylethylamine (4.53 mmol). The mixture is stirred at room temperature overnight. The mixture is concentrated in vacuo. The residue is washed with water and DCM to afford 2-phenyl-pyrimidine-5-carboxylic acid (2-sulfamoyl-ethyl)-amide as a solid. MS: 307 (M+H); ¹H NMR (300 MHz, DMSO-d₆): δ 3.25 (q, 2H), 3.67 (m, 2H), 6.93 (s, N—H), 7.47-7.60 (m, 3H), 8.36-8.48 (m, 2H), 8.92-9.15 (m, N—H), 9.16-9.36 (m, 2H); IC₅₀=55 nM.

Example 109

2-Pheny-pyrimidine-5-carboxylic acid (2-dimethylsulfamoyl-ethyl)-amide

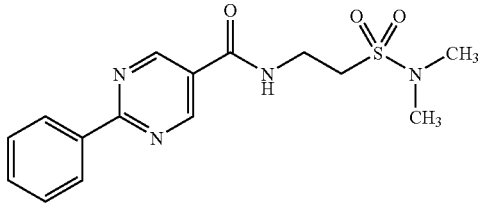

Following procedures similar to those of Example 108 but substituting 2-dimethylamino-ethanesulfonic acid amide for 2-amino-ethanesulfonic acid amide, there is prepared 2-phenyl-pyrimidine-5-carboxylic acid (2-dimethylsulfamoyl-ethyl)-amide as a solid. MS: 334 (M+H); $^1$H NMR (300 MHz, DMSO-$d_6$): δ 2.76 (s, 6H), 3.29 (t, 2H), 3.62-3.73 (m, 2H), 7.45-7.60 (m, 3H), 8.42 (m, 2H), 9.06 (bs, N—H), 9.20 (s, 2H); $IC_{50}$=82 nM.

Example 110

2-Phenyl-pyrimidine-5-carboxylic acid (3-phenyl-[1, 2,4]thiadiazol-5-yl)-amide

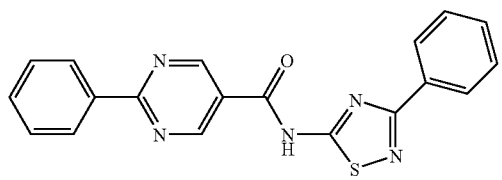

To a suspension of 2-phenyl-pyrimidine-5-carboxylic acid (400 mg, 2 mmol) in DCM (10 mL), oxalyl chloride (0.2 mL, 2.3 mmol) is added at 0° C. followed by DMF (0.23 mL, 3 mmol). The mixture is stirred at 0° C. for 20 minutes, warmed to room temperature and stirred for 20 additional min. The mixture is concentrated in vacuo. The residue is dissolved in DCM and 3-phenyl-[1,2,4]thiadiazol-5-ylamine (248 mg, 1.4 mmol) is added followed by NMP (0.5 mL). The mixture is stirred at room temperature for two hours, and concentrated in vacuo. The residue is triturated in DCM to afford 2-phenyl-pyrimidine-5-carboxylic acid (3-phenyl-[1,2,4]thiadiazol-5-yl)-amide (300 mg) as a solid. MS: 360 (M+H); $IC_{50}$=30 nM.

Example 111

4-Methyl-2-phenyl-pyrimidine-5-carboxylic acid (3-phenyl-[1, 2,4]thiadiazol-5-yl)-amide

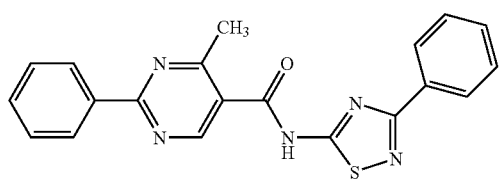

Following procedures similar to those of Example 110 but substituting 4-methyl-2-phenyl-pyrimidine-5-carboxylic acid for 2-phenyl-pyrimidine-5-carboxylic acid, there is prepared 4-methyl-2-phenyl-pyrimidine-5-carboxylic acid (3-phenyl-[1,2,4]thiadiazol-5-yl)-amide MS: 374 (M+H); $^1$H NMR (300 MHz, DMSO-$d_6$): δ 2.77 (s, 3H), 7.54-7.60 (m, 6H), 8.23 (d, 2H), 8.48 (d, 2H), 9.22 (s, 1H), 13.88 (s, 1H).

Example 112

2-(3-Fluoro-phenyl)-pyrimidine-5-carboxylic acid (3-phenyl-[1, 2,4]thiadiazol-5-yl)amide

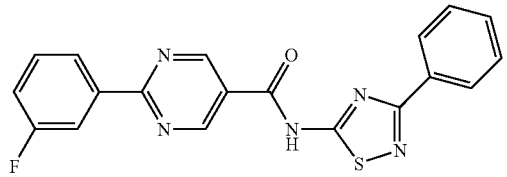

Following procedures similar to those of Example 110 but substituting 2-(3-fluoro-phenyl)pyrimidine-5-carboxylic acid for 2-phenyl-pyrimidine-5-carboxylic acid, there is prepared 2-(3-fluoro-phenyl)-pyrimidine-5-carboxylic acid (3-phenyl-[1,2,4]thiadiazol-5-yl)amide. MS: 378 (M+H).

Example 113

2-(3-Fluoro-phenyl)-pyrimidine-5-carboxylic acid (tetrahydro-pyran-4-yl)-amide

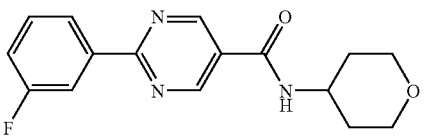

Following procedures similar to those of Example 110 but substituting 2-(3-fluoro-phenyl)pyrimidine-5-carboxylic acid for 2-phenyl-pyrimidine-5-carboxylic acid, and substituting tetrahydro-pyran-4-ylamine for 3-phenyl-[1,2,4]thiadiazol-5-ylamine, there is prepared 2-(3-fluoro-phenyl)-pyrimidine-5-carboxylic acid (tetrahydro-pyran-4-yl)-amide. MS: 302 (M+H); $^1$H NMR (300 MHz, $CD_3OD$): δ 1.60-1.64 (m, 2H), 1.81-1.84 (d, 2H), 3.33 (s, 2H), 3.38-3.45 (t, 2H), 3.88-3.92 (d, 2H), 4.02-4.06 (m, 1H), 7.46 (t, 1H) 7.62 (q, 1H), 8.14 (d, 1H), 8.29 (d, 1H), 8.70 (d, 1H), 9.27 (s, 2H).

Example 114

2-Cyclohexyl-pyrimidine-5-carboxylic acid phenylamide

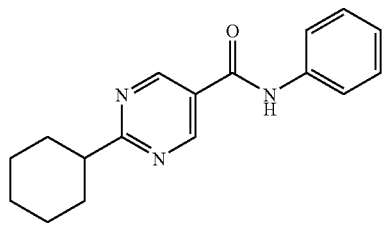

Step 1. To a solution of cyclohexanecarboxamidine hydrochloride (1 g, 7.9 mmol) in anhydrous DMF (15 mL) is added sodium 3,3-dimethoxy-2-carbomethoxyprop-1-en-1-oxide (1.82 g, 9.2 mmol) and the reaction mixture is heated at 100° C. under $N_2$ for 3 hours. The reaction is cooled to room temperature and water (59 mL) is added. The mixture is extracted with EtOAc. The organic layer is washed with saturated aqueous brine, dried ($MgSO_4$), filtered and concentrated in vacuo to afford 2-cyclohexyl-pyrimidine-5-carboxylic acid methyl ester (0.5 g, 29%) as a solid. MS: 221 (M+H).

Step 2. A solution of 2-cyclohexyl-pyrimidine-5-carboxylic acid methyl ester (0.97 g, 4.39 mmol) and aqueous LiOH (1 M, 4.39 mL) MeOH (6 mL) is stirred at room temperature overnight. MeOH is evaporated in vacuo, and the aqueous solution is treated with 3 N HCl to adjust the pH to between 2 and 3. The resulting precipitate is filtered off, washed with water and dried in vacuo to afford 2-cyclohexyl-pyrimidine-5-carboxylic acid (0.2 g, 22%) as a solid. MS: 207 (M+H).

Step 3. A mixture of 2-cyclohexyl-pyrimidine-5-carboxylic acid (100 mg, 0.48 mmol), 1-hydroxybenzotriazole (74.2 mg, 0.55 mmol), and PS-DCC (505 mg, 1.28 mmol/g, 0.65 mmol) in DMF (8 mL) is shaken at room temperature for 15 minutes, and aniline (30 mg, 0.32 mmol) is added. The mixture is shaken at room temperature for 18 hours, PS-trisamine (388 mg, 3.75 mmol/g, 1.45 mmol) is added and the mixture is continually shaken at room temperature for 18 hours. The solid is filtered and washed with DCM. The filtrate is concentrated in vacuo to afford 2-cyclohexyl-pyrimidine-5-carboxylic acid phenylamide (45.6 mg, 51%) as a solid. MS: 282 (M+H); $IC_{50}$=4960 nM.

Example 115

2-Phenyl-pyrimidine-5-carboxylic acid 3-amino-benzylamide

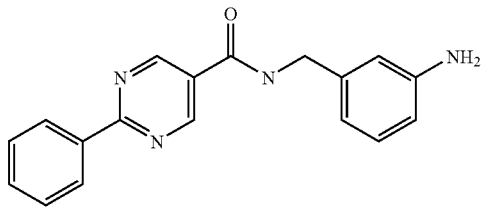

Following procedures similar to those of Example 8, but substituting 3-amino-benzylamine for 2,2-dioxo-2,3-dihydro-1H-2lamda*6*-benzo[c]isothiazol-5-ylamine there is prepared 2-phenyl-pyrimidine-5-carboxylic acid 3-aminobenzylamide as a solid. MS: 305 (M+H); $^1$H NMR (300 MHz, $CD_3OD$): δ 4.52 (s, 2H), 6.60-6.75 (m, 2H), 6.77 (bs, N—H), 7.07 (t, H), 7.47-7.59 (m, 3H), 8.44-8.53 (m, 2H), 9.23 (s, 2H).

Example 116

2-(3-Pyridyl)-pyrimidine-5-carboxylic acid-3-methylsulfamoyl-benzylamide

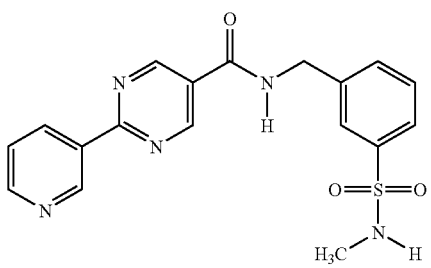

A mixture of 2-(3-pyridyl)-pyrimidine-5-carboxylic acid hydrochloride (237 mg 1 mmol) and O-(7-azabenzotriazol-1-yl)-N,N,N,N-tetramethyluronium hexafluorophosphate (380 mg, 1 mmol) in dry DMF (15 mL) is treated with diisopropylethylamine (0.36 mL) and stirred at room temperature for 30 min. 3-Methylsulfamoylbenzylamine hydrochloride (355 mg, 1.5 mmol) is added and the mixture is stirred at room temperature for 24 hours. The solvent is removed and the residue is partitioned between EtOAc and saturated aqueous $NaHCO_3$. The organic phase is separated, washed with water and brine, dried ($MgSO_4$), filtered and concentrated in vacuo. The residue is triturated with EtOAc. The resulting solid is filtered, washed with ether to afford 2-(3-pyridyl)-pyrimidine-5-carboxylic-acid-3-methylsulfamoyl-benzylamide (185 mg, 48%). MS: 384 (M+H); $^1$H NMR (300 MHz, DMSO-$d_6$): δ 2.43 (d, 3H), 4.65 (d, 2H), 7.45-7.55 (q, 1H), 7.60-7.75 (m, 3H), 7.80 (s, 1H), 8.72-8.80 (m, 2H), 9.35 (s, 2H), 9.55 (m, 2H).

Example 117

2-Pyrazol-1-yl-pyrimidine-5-carboxylic acid 4-sulfamoyl-benzylamide

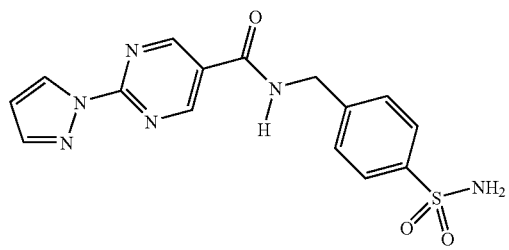

Following procedures similar to those of Example 116 but substituting 2-pyrazol-1-yl-pyrimidine-5-carboxylic acid for 2-(3-pyridyl)pyrimidine-5-carboxylic acid hydrochloride, and substituting 4-aminomethyl-benzenesulfonamide hydrochloride for 3-methylsulfamoylbenzylamine hydrochloride there is prepared 2-pyrazol-1-yl-pyrimidine-5-carboxylic acid 4-sulfamoyl-benzylamide as a solid. MS: 359 (M+H); $IC_{50}$=266 nM.

Example 118

2-(2-Methyl-thiazol-4-yl)-pyrimidine-5-carboxylic acid (tetrahydro-pyran-4-yl)-amide

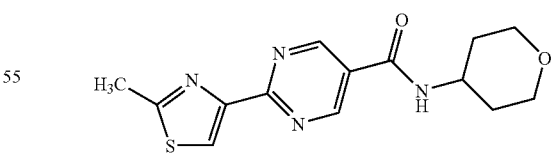

Following procedures similar to those of Example 116 but substituting 2-(2-methyl-thiazol-4-yl)-pyrimidine-5-carboxylic acid for 2-(3-pyridyl)pyrimidine-5-carboxylic acid hydrochloride, and substituting tetrahydro-pyran-4-ylamine for 3-methylsulfmoylbenzylamine hydrochloride there is prepared 2-(2-methyl-thiazol-4-yl)-pyrimidine-5-carboxylic acid (tetrahydro-pyran-4-yl)-amide as a solid. MS: 305 (M+H); $IC_{50}$=82 nM.

Following the general procedures described in the above examples, the following compounds can be made:

2-Phenyl-pyrimidine-5-carboxylic acid (thiophen-2-ylmethyl)-amide,
2-Phenyl-pyrimidine-5-carboxylic acid (4-methyl-oxazol-2-yl)-amide,
Methoxyimino-{2-[(2-phenyl-pyrimidine-5-carbonyl)-amino]-thiazol-4-yl}-acetic acid ethyl ester,
2-Phenyl-pyrimidine-5-carboxylic acid (5-methylsulfanyl-[1,3,4]thiadiazol-2-yl)-amide,
2-[(2-Phenyl-pyrimidine-5-carbonyl)-amino]-benzothiazole-5-carboxylic acid ethyl ester,
(R)-2-Phenyl-pyrimidine-5-carboxylic acid (1-phenyl-ethyl)-amide,
2-Phenyl-pyrimidine-5-carboxylic acid [3-(1H-tetrazol-5-yl)-phenyl]-amide,
2-Phenyl-pyrimidine-5-carboxylic acid (1-carbamimidoyl-piperidin-4-ylmethyl)-amide,
5-[(2-Phenyl-pyrimidine-5-carbonyl)-amino]-1H-indole-3-carboxylic acid amide,
2-Phenyl-pyrimidine-5-carboxylic acid [3-(2-amino-thiazol-4-yl)-phenyl]-amide,
2-Phenyl-pyrimidine-5-carboxylic acid {4-[2-(1,3-dioxo-1,3-dihydro-isoindol-2-yl)-ethyl]-thiazol-2-yl}-amide,
2-(3-Fluoro-phenyl)-pyrimidine-5-carboxylic acid [2-(pyrrolidine-1-sulfonyl)-ethyl]-amide,
[3-({[2-(3-Fluoro-phenyl)-4-methyl-pyrimidine-5-carbonyl]-amino}-methyl)-benzyl]-carbamic acid tert-butyl ester,
2-(3-Fluoro-phenyl)-pyrimidine-5-carboxylic acid 3-[(pyridin-2-ylmethyl)-sulfamoyl]-benzylamide,
2-(3-Fluoro-phenyl)-pyrimidine-5-carboxylic acid 3-(3-hydroxy-2,2-dimethyl-propylsulfamoyl)-benzylamide,
2-(3-Fluoro-phenyl)-pyrimidine-5-carboxylic acid 3-(2-hydroxy-2-methyl-propylsulfamoyl)-benzylamide,
2-(3-Fluoro-phenyl)-pyrimidine-5-carboxylic acid 3-[(tetrahydro-pyran-4-ylmethyl)-sulfamoyl]-benzylamide,
2-(3-Fluoro-phenyl)-pyrimidine-5-carboxylic acid 3-(4-hydroxy-butylsulfamoyl)-benzylamide,
2-(3-Fluoro-phenyl)-pyrimidine-5-carboxylic acid 3-[2-(2-hydroxy-ethoxy)-ethylsulfamoyl]-benzylamide,
2-(3-Fluoro-phenyl)-pyrimidine-5-carboxylic acid 3-[(tetrahydro-furan-2-ylmethyl)-sulfamoyl]-benzylamide,
2-(3-Fluoro-phenyl)-pyrimidine-5-carboxylic acid 3-isobutylsulfamoyl-benzylamide,
2-(3-Fluoro-phenyl)-pyrimidine-5-carboxylic acid (5-isopropylsulfamoyl-pyridin-3-ylmethyl)-amide,
2-(3-Fluoro-phenyl)-pyrimidine-5-carboxylic acid (5-methylsulfamoyl-pyridin-3-ylmethyl)-amide,
2-(3-Fluoro-phenyl)-pyrimidine-5-carboxylic acid (2-methylsulfamoyl-pyridin-4-ylmethyl)-amide,
2-(3-Fluoro-phenyl)-4-methyl-pyrimidine-5-carboxylic acid (2-methylsulfamoyl-pyridin-4-ylmethyl)-amide, and
2-(3-Fluoro-phenyl)-4-methyl-pyrimidine-5-carboxylic acid (5-isopropylsulfamoyl-pyridin-3-ylmethyl)-amide.

In Vitro Assay Protocols to Identify Inhibitors of Hematopoietic PGD2 Synthase

The compounds of the present invention can be tested for enzymatic inhibiting activity against PGD2 Synthase according to either one of the following assays.

Assay 1: Fluorescence Polarization Assay
As described in PCT publication WO 2004/016223, Example II.

Assay 2: Enzyme Immunoassay (EIA) Method
I. Assay solutions
  a. Preparation of 0.1M $K_2HPO_4/KH_2PO_4$ buffer (pH ~7.4)
    Prepare 0.1 M $KH_2PO_4$ from 1M $KH_2PO_4$ (Sigma, Cat# P-8709)
    Prepare 0.1 M $K_2HPO_4$ from powder of $K_2HPO_4$ (Fisher, BP363-500)
    Mix 0.1 M $K_2HPO_4$ with 0.1 M $KH_2PO_4$ to adjust pH to 7.4.
  b. Preparation of 0.5% γ-globulin
    Add 0.1 g of γ-globulin (Sigma, Cat# G-5009) to 20 mL 0.1 M $K_2HPO_4/KH_2PO_4$ buffer (pH ~7.4) and make 1-ml/vial aliquots and store in −80° C.
  c. Preparation of 100 mM GSH
    Add 307 mg of GSH (Sigma, Cat# G-6529) to 10 mL 0.1 M $K_2HPO_4/KH_2PO_4$ buffer (pH ~7.4) and store at −80° C.
  d. Preparation of Reaction buffer:
    198 mL of 0.1M $K_2HPO_4/KH_2PO_4$ buffer (pH ~7.4)
    2 mM GSH—Prepared from 100 mM GSH
    0.4 g Glycerol
    2 mL of 0.5% γ-globulin
    Add 0.4 g of glycerol and 2 mL of 0.5% γ-globulin to 198 mL of 0.1 M $K_2HPO_4/KH_2PO_4$ buffer (pH7.4).
    Add 0.4 mL of 100 mM GSH to 19.6 ml reaction buffer before the assay (enough for two 96-well plates).
  e. Preparation of $FeCl_2$/citric acid stopping solution: (8 mg/mL $FeCl_2$, 0.1 M citric acid)
    Add 40 mg fresh $FeCl_2$ (IGN, Cat# 158046) to 5 ml 0.1 M citric acid (Sigma, Cat# C0759).
  f. Preparation of MOX reagent:
    10% EtOH-Add 1 mL of EtOH to 9 mL of ultra pure $H_2O$
    Dissolve 0.1 g of methoxylamine (Cayman, Cat# 400036/) in 10% EtOH (10 mL).
    Add 0.82 g of sodium acetate (Cayman, Cat#400037) to MOX solution and dissolve.
II. Materials and Method
  Dimethylsulfoxide (DMSO; Sigma; Cat# D2650)
  Prostaglandin D2-MOX express EIA kit (Caymen Chemical, Catalog No. 500151)
  Before the assay, cool down 10 mL of acetone in polypropylene tubes and empty 96 well plates in ice. All the procedures except compound dilution are performed on ice.
III. Compound Dilution
  1. Dilute Compound in DMSO

| Vol of DMSO stock solution (μL) | DMSO (μL) | Compound concentration (mM) |
|---|---|---|
| 4 μL of 10 mM | 6 μL | 4 |
| 3 μL of 4 mM | 6 μL | 1.3333 |
| 3 μL of 1.33 mM | 6 μL | 0.4444 |
| 3 μL of 0.44 mM | 6 μL | 0.1481 |
| 3 μL of 0.148 mM | 6 μL | 0.0494 |
| 3 μL of 0.049 mM | 6 μL | 0.0165 |
| 3 μL of 0.016 mM | 6 μL | 0.0055 |

2. Dilute 2 μL of each above concentration of compound to 38 μL of reaction buffer in 96-well plates and mix.
IV. Enzyme and Substrate Solution Preparation
  1. Preparation of 0.39 ng/μL enzyme solution (0.35 ng/μL at final after compound addition).
    Mix 4 μL of 4 mg/mL human h-PGDS with 396 μL of reaction buffer (to give enzyme concentration 40

μg/mL). Add 46.8 μL of 40 μg/mL h-PGDS to 4.753 mL of reaction buffer to give a total volume of 4.8 mL 2. Preparation of Substrate Solution (PGH2): Add 0.375 mL of 0.1 mg/mL of PGH2 to 1.625 mL acetone.

V. Enzyme Reaction:
1. Add 60 μL of enzyme solution to compound well and positive control (without compound) in U-bottom polypropylene plate on ice.
2. Add 60 μL of reaction buffer and 6.6 μL of 5% DMSO in reaction buffer into negative control wells in the plate.
3. Add 6.6 μL of diluted compound in reaction buffer to the compound wells and mix.
4. Add 6.6 μL of 5% DMSO in reaction buffer to the positive control well.
5. Incubate the plate in ice for at least 30 min.
6. Add 20 μL of substrate (PGH2) solution to compound, negative and positive control wells in the U-bottom 96 well plate on ice.
7. Dry the plate in cold room for about 25-28 min.
8. Pipette 45 μL of enzyme solution (above) into 96-wells with dried PGH2 and mix 3 times. Incubate on the ice for 1 min.
9. Add 45 μL of $FeCl_2$ solution into each wells and mix.
10. Add 90 μL of MOX solution and mix.
11. Incubate for 30 min at 60° C.
12. Dilute the samples 2500× with EIA buffer.

VI. EIA assay
Perform the assay according to the procedure in EIA kit provided by Cayman. Total PGD2 levels (pg/mL) were determined in the samples by EIA kits (Caymen Chemical, Catalog No. 500151)
Calculate amount of PGD2 as below
Calculated % Positive control according to the equation below;

% Positive control=(Compound value−Negative control)/(Positive value-Negative control value)× 100.

% Positive control=(Compound value-Negative control)×100(Positive Value-Negative Control Value)

Compound value=PGD2 levels (pg/mL) obtained from the standard curve in EIA assay for the samples with compound
Negative control value=PGD2 levels (pg/mL) obtained from the standard curve in EIA assay for the samples without enzyme
Positive control value=PGD2 levels (pg/mL) obtained from the standard curve in EIA assay for the samples with enzyme but without compound
$IC_{50}$s are determined by excel fit to get the x value when y=½Ymax using 4 parameter logistic model for the $IC_{50}$ curves.

Results
Compounds within the scope of the invention produce 50% inhibition in the Fluorescence Polarization Assay or the EIA assay at concentrations within the range of about 1 nanomolar to about 30 micromolar, The $IC_{50}$s for Examples 8, 9, 33, 34, 82, 83, 84 and 114 obtained by the Fluorescence Polarization Assay, and the $IC_{50}$s for Examples 1, 30, 38, 40, 45, 48, 49, 51, 54, 55, 56, 63, 65, 68, 71, 85, 93, 97, 108, 109, 110, 117 and 118 obtained by the EIA assay are reported in the "EXAMPLE" section herein.

The present invention may be embodied in other specific forms without departing from the spirit or essential attributes thereof.

We claim:
1. A compound of formula (I):

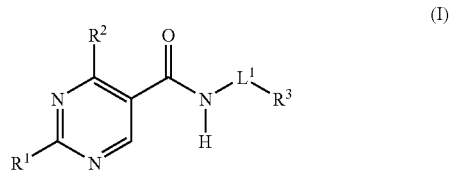

wherein:
$R^1$ is aryl, heteroaryl, or $(C_5-C_6)$-cycloalkyl, each of which is optionally substituted by halo, $(C_1-C_6)$-alkyl, hydroxy, $(C_1-C_6)$-alkoxy, $(C_1-C_4)$-haloalkyl or $(C_1-C_4)$-haloalkoxy;
$R^2$ is hydrogen or $(C_1-C_4)$-alkyl;
$R^3$ is —P(=O)-(alkoxy)$_2$, $Y^1Y^2N$—$SO_2$—, cycloalkyl, cycloalkenyl, aryl, heteroaryl, heterocyclyl, or heterocyclenyl, each of which is optionally substituted by:
acyl, cyano, nitro, halo, hydroxy, carboxy, amidino, $R^5$—O—C(=O)—C(=N—$OR^4$)—, $Y^1Y^2N$—, $Y^1Y^2N$—C(=O)—, $Y^1Y^2N$—C(=O)—O—, $Y^1Y^2N$—$SO_2$—,
$R^7$—$SO_2$—$NR^6$—, $R^7$—C(=O)—$NR^6$—, $Y^1Y^2N$—$(C_1-C_4)$-alkylene-$SO_2$—$(C_1-C_4)$-alkylene-,
alkyl, alkenyl, alkynyl, alkoxy, alkoxycarbonyl, alkylthio, alkylsulfinyl, or alkylsulfonyl, each of which is optionally substituted by:
halo, alkoxy, haloalkoxy, hydroxy, carboxy, alkoxycarbonyl, —P(=O)—(alkoxy)$_2$, $Y^1Y^2N$—, $Y^1Y^2N$—$SO_2$—,$R^7$—$NR^6$—,
aryl or heteroaryl, each of which is optionally substituted by alkyl, halo, haloalkyl, alkoxy, haloalkoxy, hydroxy, amino, alkylamino, dialkylamino, carboxy, or alkoxycarbonyl, or
heterocyclyl or arylheterocyclyl, each of which is optionally substituted by oxo or alkyl, or
aryl, heteroaryl, aroyl, heteroaroyl, aryloxy, heteroaryloxy, or heterocyclyl, each of which is optionally substituted by alkyl, haloalkyl, halo, alkoxy, haloalkoxy, hydroxy, carboxy, alkoxycarbonyl, —P(=O)-(alkoxy)$_2$, $Y^1Y^2N$—, or $Y^1Y^2N$—$SO_2$—, and
when $R^3$ is cycloalkyl, cycloalkenyl, heterocyclyl or heterocyclenyl, it is also optionally substituted by oxo;
$L^1$ is a bond, or $(C_1-C_6)$-alkylene optionally substituted by hydroxyl, or when $R^3$ is optionally substituted cycloalkyl, cycloalkenyl, aryl, heteroaryl, heterocyclyl or heterocyclenyl, then the $(C_1-C_6)$-alkylene is also optionally substituted by —P(=O)—(alkoxy)$_2$;
$R^4$, $R^5$ and $R^6$ are each independently hydrogen or alkyl;
$R^7$ is alkyl optionally substituted by hydroxy, halo or alkoxy, or
aryl, heteroaryl, arylalkyl or heteroarylalkyl, wherein the aryl, heteroaryl, or the aryl or heteroaryl moiety of the arylalkyl or heteroarylalkyl is optionally substituted by alkyl, haloalkyl, hydroxy, carboxy, alkoxycarbonyl, amino, alkylamino, dialkylamino, halo, alkoxy or haloalkoxy; and
$Y^1$ and $Y^2$ are each independently:
hydrogen,
alkyl optionally substituted by:
hydroxy, carboxy, halo, amino, alkylamino, dialkylamino, cycloalkylamino,
aminocarbonyl, alkylaminocarbonyl, dialkylaminocarbonyl, cycloalkylaminocarbonyl,
alkoxy optionally substituted with hydroxy,
cycloalkyl, heterocyclyl, aryl or heteroaryl, each of which is optionally substituted by alkyl, halo or haloalkyl, or
cycloalkyl optionally substituted by carboxy, or $Y^1$ and $Y^2$ together with the nitrogen atom to which they are attached form a heterocyclyl optionally containing another heteroatom selected from oxygen, nitrogen or sulfur, wherein the heterocyclyl is optionally substituted by alkyl or oxo;

provided that when $L^1$ is a bond, then $R^3$ is not optionally substituted phenyl, optionally substituted naphthyl, optionally substituted benzimidazolyl, optionally substituted benzothiazolyl, optionally substituted tetrazolyl, optionally substituted indazolyl, optionally substituted benzotriazolyl, optionally substituted benzisoxazolyl, or optionally substituted benzoxazolyl, or N-oxide thereof, or a pharmaceutically acceptable salt thereof.

2. The compound according to claim 1, wherein $R^1$ is phenyl, five or six-membered heteroaryl, or $(C_5-C_6)$-cycloalkyl, each of which is optionally substituted by halo, $(C_1-C_6)$-alkyl, hydroxy, $(C_1-C_6)$-alkoxy, $(C_1-C_4)$-haloalkyl or $(C_1-C_4)$-haloalkoxy, or N-oxide thereof, or a pharmaceutically acceptable salt thereof.

3. The compound according to claim 1, wherein $R^1$ is phenyl or five or six membered heteroaryl, each of which is optionally substituted by halo, $(C_1-C_6)$-alkyl, hydroxy, $(C_1-C_6)$-alkoxy, $(C_1-C_4)$-haloalkyl or $(C_1-C_4)$-haloalkoxy, or N-oxide thereof, or a pharmaceutically acceptable salt thereof.

4. The compound according to claim 1, wherein $R^1$ is phenyl or five or six membered heteroaryl, each of which is optionally substituted by halo, $(C_1-C_6)$-alkyl, hydroxy, $(C_1-C_6)$-alkoxy, $(C_1-C_4)$-haloalkyl or $(C_1-C_4)$-haloalkoxy, or N-oxide thereof, or a pharmaceutically acceptable salt thereof, provide that when $R^1$ is phenyl or six membered heteroaryl, then it is only optionally substituted at the ortho or meta position.

5. The compound according to claim 1, wherein $R^1$ is phenyl, pyridyl, thiazolyl, or imidazolyl, oxadiazolyl, each of which is optionally substituted by halo, $(C_1-C_6)$-alkyl, hydroxy, $(C_1-C_6)$-alkoxy, $(C_1-C_4)$-haloalkyl or $(C_1-C_4)$-haloalkoxy, or N-oxide thereof, or a pharmaceutically acceptable salt thereof.

6. The compound according to claim 1, wherein $R^1$ is phenyl or pyridyl, each of which is optionally substituted at the ortho or meta position by halo, $(C_1-C_6)$-alkyl, hydroxy, $(C_1-C_6)$-alkoxy, $(C_1-C_4)$-haloalkyl or $(C_1-C_4)$-haloalkoxy, or N-oxide thereof, or a pharmaceutically acceptable salt thereof.

7. The compound according to claim 1, wherein $R^1$ is phenyl optionally substituted by halo, $(C_1-C_6)$-alkyl, hydroxy, $(C_1-C_6)$-alkoxy, $(C_1-C_4)$-haloalkyl or $(C_1-C_4)$-haloalkoxy, or N-oxide thereof, or a pharmaceutically acceptable salt thereof.

8. The compound according to claim 1, wherein $R^1$ is phenyl optionally substituted at the ortho or meta position by halo, $(C_1-C_6)$-alkyl, hydroxy, $(C_1-C_6)$-alkoxy, $(C_1-C_4)$-haloalkyl or $(C_1-C_4)$-haloalkoxy, or N-oxide thereof, or a pharmaceutically acceptable salt thereof.

9. The compound according to claim 1, wherein $R^1$ is phenyl optionally substituted by halo, or N-oxide thereof, or a pharmaceutically acceptable salt thereof.

10. The compound according to claim 1, wherein $R^1$ is phenyl optionally substituted at the ortho or meta position by halo, or N-oxide thereof, or a pharmaceutically acceptable salt thereof.

11. The compound according to claim 1, wherein $R^1$ is 2-fluorophenyl or 3-fluorophenyl, or N-oxide thereof, or a pharmaceutically acceptable salt thereof.

12. The compound according to claim 1, wherein $R^2$ is hydrogen, or N-oxide thereof, or a pharmaceutically acceptable salt thereof.

13. The compound according to claim 1, wherein $R^2$ is methyl, or N-oxide thereof, or a pharmaceutically acceptable salt thereof.

14. The compound according to claim 1, wherein $L^1$ is a bond, or N-oxide thereof, or a pharmaceutically acceptable salt thereof.

15. The compound according to claim 1, wherein $L^1$ is $(C_1-C_3)$-alkylene, or N-oxide thereof, or a pharmaceutically acceptable salt thereof.

16. The compound according to claim 1, wherein $L^1$ is —$CH_2$—, or N-oxide thereof, or a pharmaceutically acceptable salt thereof.

17. The compound according to claim 1, wherein
$R^3$ is cycloalkyl, cycloalkenyl, aryl, heteroaryl, heterocyclyl, or heterocyclenyl, each of which is optionally substituted by:
acyl, cyano, nitro, halo, hydroxy, carboxy, amidino, $R^5O$—$C(=O)$—$C(=N$—$OR^4)$—, $Y^1Y^2N$—, $Y^1Y^2N$—$C(=O)$—, $Y^1Y^2N$—$C(=O)$—$O$—, $Y^1Y^2N$—$SO_2$—,
$R^7$—$SO_2$—$NR^6$—, $R^7$—$C(=O)$—$NR^6$—, $Y^1Y^2N$—$(C_1-C_4)$-alkylene-$SO_2$—$(C_1-C_4)$-alkylene-, or alkyl, alkenyl, alkynyl, alkoxy, alkoxycarbonyl, alkylthio, alkylsulfinyl, or alkylsulfonyl, each of which is optionally substituted by:
halo, alkoxy, haloalkoxy, hydroxy, carboxy, alkoxycarbonyl,
—$P(=O)$-$(alkoxy)_2$, $Y^1Y^2N$—, $Y^1Y^2N$—$SO_2$—, $R^7$—$SO_2$—$NR^6$—,
aryl or heteroaryl, each of which is optionally substituted by alkyl, halo, haloalkyl, alkoxy, haloalkoxy, hydroxy, amino, alkylamino, dialkylamino, carboxy, or alkoxycarbonyl, or
heterocyclyl or arylheterocyclyl, each of which is optionally substituted by oxo or alkyl, or
aryl, heteroaryl, aroyl, heteroaroyl, aryloxy, heteroaryloxy, or heterocyclyl, each of which is optionally substituted by alkyl, haloalkyl, halo, alkoxy, haloalkoxy, hydroxy, carboxy, alkoxycarbonyl, —$P(=O)$-$(alkoxy)_2$, $Y^1Y^2N$—, or $Y^1Y^2N$—$SO_2$—, and
when $R^3$ is cycloalkyl, cycloalkenyl, heterocyclyl, or heterocyclenyl, it is also optionally substituted by oxo, or N-oxide thereof, or a pharmaceutically acceptable salt thereof.

18. The compound according to claim 1, wherein $R^3$ is phenyl, pyridyl, thiazolyl, imidazolyl, oxadiazolyl, imidazolyl, pyrimidinyl, thiophenyl, oxazolyl, cycloalkyl, benzoxazolyl, 1,2,4-thiadiazolyl, 1,3,4-thiadiazolyl, tetrahydropyranyl, piperidinyl, furanyl, benzothiazolyl, imidazolidinyl, indazolyl, benzimidazolyl, indolyl, or benzofuranyl, each of which is optionally substituted by:
acyl, cyano, nitro, halo, hydroxy, carboxy, amidino, $R^5O$—$C(=O)$—$C(=N$—$OR^4)$—, $Y^1Y^2N$—, $Y^1Y^2N$—$C(=O)$—, $Y^1Y^2N$—$C(=O)$—$O$—, $Y^1Y^2N$—$SO_2$—, $R^7$—$SO_2$—$NR^6$—, $R^7$—$C(=O)$—$NR^6$—, $Y^1Y^2N$—$(C_1-C_4)$-alkylene-$SO_2$—$(C_1-C_4)$-alkylene-, or alkyl, alkenyl, alkynyl, alkoxy, alkoxycarbonyl, alkylthio, alkylsulfinyl, or alkylsulfonyl,
each of which is optionally substituted by:
halo, alkoxy, haloalkoxy, hydroxy, carboxy, alkoxycarbonyl, —P(=O)-(alkoxy)$_2$, $Y^1Y^2N$—, $Y^1Y^2N$—SO$_2$—, $R^7$—SO$_2$—NR$^6$—,
aryl or heteroaryl, each of which is optionally substituted by alkyl, halo, haloalkyl, alkoxy, haloalkoxy, hydroxy, amino, alkylamino, dialkylamino, carboxy, or alkoxycarbonyl, or
heterocyclyl or arylheterocyclyl, each of which is optionally substituted by oxo or
alkyl, or
aryl, heteroaryl, aroyl, heteroaroyl, aryloxy, heteroaryloxy, or heterocyclyl, each of which is optionally substituted by alkyl, haloalkyl, halo, alkoxy, haloalkoxy, hydroxy, carboxy, alkoxycarbonyl, —P(=O)-(alkoxy)$_2$, $Y^1Y^2N$—, or $Y^1Y^2N$—SO$_2$—, and
when R$^3$ is cycloalkyl, tetrahydropyranyl, piperidinyl, imidazolidinyl, or 1,3-dihydro-benzo[c]isothiazolyl, it is also optionally substituted by oxo,
or N-oxide thereof, or a pharmaceutically acceptable salt thereof.

19. The compound according to claim 1, wherein:
R$^3$ is phenyl, pyridyl, thiazolyl, imidazolyl, oxadiazolyl, imidazolyl, pyrimidinyl, thiophenyl, oxazolyl, cycloalkyl, benzoxazolyl, 1,2,4-thiadiazolyl, 1,3,4-thiadiazolyl, tetrahydropyranyl, piperidinyl, furanyl, benzothiazolyl, imidazolidinyl, indazolyl, benzimidazolyl $Y^1Y^2N$—SO$_2$—, $R^7$—SO$_2$—NR$^6$—, $R^7$—C(=O)—NR$^6$-, alkoxy, alkoxycarbonyl, alkylthio,
alkylsulfonyl, aryl, heteroaryl, or
alkyl optionally substituted by:
halo, carboxy, alkoxycarbonyl, aryl or heteroaryl, —P(=O)-(alkoxy)$_2$, $Y^1Y^2N$—, $Y^1Y^2N$—SO$_2$—, $R^7$—SO$_2$—NR$^6$—, or
heterocyclyl or arylheterocyclyl, each of which is optionally substituted by oxo,
or
heterocyclyl optionally substituted by $Y^1Y^2N$—, and
when R$^3$ is cycloalkyl, tetrahydropyranyl, piperidinyl, or imidazolidinyl, it is also optionally substituted by oxo; and
$Y^1$ and $Y^2$ are each independently hydrogen, cycloalkyl, or alkyl optionally substituted by hydroxy, alkoxy, amino, alkylamino, dialkylamino, heteroaryl, or heterocyclyl optionally substituted by alkyl,
or N-oxide thereof, or a pharmaceutically acceptable salt thereof.

20. The a compound according to claim 1, wherein R$^3$ is phenyl optionally substituted by:
acyl, cyano, nitro, halo, hydroxy, carboxy, amidino, $R^5O$—C(=O)—C(=N—OR$^4$)—, $Y^1Y^2N$—, $Y^1Y^2N$—C(=O)—, $Y^1Y^2N$—C(=O)—O—, $Y^1Y^2N$—SO$_2$—, $R^7$—SO$_2$—NR$^6$—, $R^7$—C(=O)—NR$^6$—, $Y^1Y^2N$—(C$_1$-C$_4$)-alkylene-SO$_2$-(C$_1$-C$_4$)-alkylene-, or
alkyl, alkenyl, alkynyl, alkoxy, alkoxycarbonyl, alkylthio, alkylsulfinyl, or alkylsulfonyl,
each of which is optionally substituted by:
halo, alkoxy, haloalkoxy, hydroxy, carboxy, alkoxycarbonyl, —P(=O)-(alkoxy)$_2$, $Y^1Y^2N$—, $Y^1Y^2N$—SO$_2$—, $R^7$—SO$_2$—NR$^6$—,
aryl or heteroaryl, each of which is optionally substituted by alkyl, halo, haloalkyl, alkoxy, haloalkoxy, hydroxy, amino, alkylamino, dialkylamino, carboxy, or alkoxycarbonyl, or
heterocyclyl or arylheterocyclyl, each of which is optionally substituted by oxo or
alkyl, or
aryl, heteroaryl, aroyl, heteroaroyl, aryloxy, heteroaryloxy, or heterocyclyl, each of which is optionally substituted by alkyl, haloalkyl, halo, alkoxy, haloalkoxy, hydroxy, carboxy, alkoxycarbonyl, —P(=O)-(alkoxy)$_2$, $Y^1Y^2N$—, or $Y^1Y^2N$—SO$_2$—,
or N-oxide thereof, or a pharmaceutically acceptable salt thereof.

21. The compound according to claim 1, wherein:
R$^3$ is phenyl optionally substituted by:
nitro, halo, hydroxy, carboxy, amidino, $R^5O$—C(=O)—C(=N—OR$^4$)—, $Y^1Y^2N$—, $Y^1Y^2N$—C(=O)—, $Y^1Y^2N$—SO$_2$—, $R^7$—SO$_2$NR$^6$—, $R^7$—C(=O)—NR$^6$—, alkoxy, alkoxycarbonyl,
alkylthio, alkylsulfonyl, aryl, heteroaryl, or
alkyl optionally substituted by:
halo, carboxy, alkoxycarbonyl, aryl or heteroaryl, —P(=O)-(alkoxy)$_2$, $Y^1Y^2N$—, $Y^1Y^2N$—SO$_2$—, $R^7$—SO$_2$—NR$^6$—, or
heterocyclyl or arylheterocyclyl, each of which is optionally substituted by oxo,
or
heterocyclyl optionally substituted by $Y^1Y^2N$—, and
$Y^1$ and $Y^2$ are each independently hydrogen, cycloalkyl, or alkyl optionally substituted by hydroxy, alkoxy, amino, alkylamino, dialkylamino, heteroaryl, or heterocyclyl optionally substituted by alkyl,
or N-oxide thereof, or a pharmaceutically acceptable salt thereof.

22. The compound according to claim 1, wherein R$^3$ is phenyl optionally substituted by:
$Y^1Y^2N$—So$_2$—, $R^7$—So$_2$—NR$^6$-, alkylsulfonyl, or
alkyl substituted by $Y^1Y^2N$—SO$_2$—, $R^7$—SO$_2$—NR$^6$—,
or N-oxide thereof, or a pharmaceutically acceptable salt thereof.

23. The compound according to claim 1, wherein:
R$^3$ is phenyl optionally substituted by:
$Y^1Y^2N$—SO$_2$—, $R^7$—SO$_2$—NR$^6$—, alkylsulfonyl, or alkyl substituted by $Y^1Y^2N$—SO$_2$—, $R^7$—SO$_2$—NR$^6$—; and
$Y^1$ and $Y^2$ are each independently hydrogen, cycloalkyl, or alkyl optionally substituted by hydroxy, alkoxy, amino, alkylamino, dialkylamino, heteroaryl, or heterocyclyl optionally substituted by alkyl,
or N-oxide thereof, or a pharmaceutically acceptable salt thereof.

24. A compound, which is
2-Phenyl-pyrimidine-5-carboxylic acid benzylamide,
2-Pyridin-4-yl-pyrimidine-5-carboxylic acid phenylamide,
2-Pyridin-3-yl-pyrimidine-5-carboxylic acid phenylamide,
2-Pyridin-2-yl-pyrimidine-5-carboxylic acid phenylamide,
2-(3-Fluoro-phenyl)-pyrimidine-5-carboxylic acid phenylamide,
2-(4-Fluoro-phenyl)-pyrimidine-5-carboxylic acid phenylamide,
2-(2-Fluoro-phenyl)-pyrimidine-5-carboxylic acid phenylamide,
2-Phenyl-pyrimidine-5-carboxylic acid [1-(1H-imidazol-2-ylmethyl-piperidin-4-yl]-amide, 2-Phenyl-pyrimidine-5-carboxylic acid (6-dimethylamino-pyridin-3-ylmethyl)-amide,
2-Phenyl-pyrimidine-5-carboxylic acid [2-(2-pyrrolidin-1-yl-ethyl)-benzooxazol-6yl]-amide,
2-Phenyl-pyrimidine-5-carboxylic acid 4-sulfamoyl-benzylamide,
2-Phenyl-pyrimidine-5-carboxylic acid [2-(4-sulfamoyl-phenyl)-ethyl]-amide,
(R)-2-Phenyl-pyrimidine-5-carboxylic acid [4-(2-oxo-oxazolidin-4-ylmethyl)-phenyl]-amide,
2-Phenyl-pyrimidine-5-carboxylic acid (6-acetylamino-pyridin-3-yl)-amide,
2-Phenyl-pyrimidine-5-carboxylic acid (3-carbamoyl-phenyl)-amide,
2-Phenyl-pyrimidine-5-carboxylic acid (3-methylcarbamoyl-phenyl)-amide,
2-Phenyl-pyrimidine-5-carboxylic acid (4-hydroxy-cyclohexyl)-amide,
4-methyl-2-[(2-phenyl-pyrimidin-5-carbonyl)-amino]-thiazole-5-carboxylic acid ethyl ester,
{2-[(2-phenyl-pyrimidine-5-carbonyl)-amino]-thiazol-4-yl}-acetic acid ethyl ester,
4-methyl-2-[(2-phenyl-pyrimidine-5-carbonyl)-amino]-thiazole-5-carboxylic acid,
{2-[(2-phenyl-pyrimidine-5-carbonyl)-amino]-thiazol-4-yl}-acetic acid,
2-Phenyl-pyrimidine-5-carboxylic acid 4-methylsulfamoyl-benzylamide,
2-Phenyl-pyrimidine-5-carboxylic acid 4-dimethylsulfamoyl-benzylamide,
2-Phenyl-pyrimidine-5-carboxylic acid (3,5-difluoro-phenyl)-amide,
2-Phenyl-pyrimidine-5-carboxylic acid pyridin-2-ylamide,
2-Phenyl-pyrimidine-5-carboxylic acid thiazol-2-ylamide,
2-Phenyl-pyrimidine-5-carboxylic acid (3-sulfamoyl-phenyl)-amide,
2-Phenyl-pyrimidine-5-carboxylic acid (2-oxo-1,2-dihydro-pyrimidin-4-yl)-amide,
2-Phenyl-pyrimidine-5-carboxylic acid (4-sulfamoyl-phenyl)-amide,
2-Phenyl-pyrimidine-5-carboxylic acid pyrimidin-4-ylamide,
2-Phenyl-pyrimidine-5-carboxylic acid (1-pyridin-3-ylmethyl-piperidin-4-yl)-amide,
2-Phenyl-pyrimidine-5-carboxylic acid [2-(2-oxo-imidazolidin-1-yl)-ethyl]-amide,
2-Phenyl-pyrimidine-5-carboxylic acid [2-(1H-imidazol-4-yl)-ethyl]-amide,
2-Phenyl-pyrimidine-5-carboxylic acid (tetrahydro-pyran-4-ylmethyl)-amide,
2-Phenyl-pyrimidine-5-carboxylic acid (3-trifluoromethyl-phenyl)-amide,
2-Phenyl-pyrimidine-5-carboxylic acid (2H-pyrazol-3-yl)-amide,
2-Phenyl-pyrimidine-5-carboxylic acid (1-methyl-piperidin-4-yl)-amide,
2-Phenyl-pyrimidine-5-carboxylic acid pyrimidin-2-ylamide,
2-(3,5-difluoro-phenyl)-pyrimidine-5-carboxylic acid 3-methylsulfamoyl-benzylamide,
2-(2,5-difluoro-phenyl)-pyrimidine-5-carboxylic acid 3-methylsulfamoyl-benzylamide,
2-(4-difluorophenyl)-4-methylpyrimidine-5-carboxylic acid-3-methylsulfamoyl-benzylamide,
2-(2-pyridyl)-pyrimidine-5-carboxylic acid-3-methylsulfamoyl-benzylamide,
2-(3-pyridyl)-4-methyl-pyrimidine-5-carboxylic acid-3-methylsulfamoyl-benzylamide,
2-(3-Fluoro-phenyl)-pyrimidine-5-carboxylic acid 3-ethylsulfamoyl-benzylamide,
2-(3-Fluoro-phenyl)-pyrimidine-5-carboxylic acid 3-(2-ethoxy-ethylsulfamoyl)-benzylamide,
2-(3-Fluoro-phenyl)-pyrimidine-5-carboxylic acid 3-(2-hydroxy-propylsulfamoyl)-benzylamide,
2-(3-Fluoro-phenyl)-pyrimidine-5-carboxylic acid 3-cyclopropylsulfamoyl-benzylamide,
2-(3-Fluoro-phenyl)-pyrimidine-5-carboxylic acid 3-(3-hydroxy-propylsulfamoyl)-benzylamide,
2-(3-Fluoro-phenyl)-pyrimidine-5-carboxylic acid 3-(2-methoxy-ethylsulfamoyl)-benzylamide,
2-(3-Fluoro-phenyl)-pyrimidine-5-carboxylic acid 3-(3-methoxy-propylsulfamoyl)-benzylamide,
2-(3-Fluoro-phenyl)-pyrimidine-5-carboxylic acid 3-(4-methoxy-butylsulfamoyl)-benzylamide,
2-(3-Fluoro-phenyl)-pyrimidine-5-carboxylic acid 3-cyclohexylsulfamoyl-benzylamide,
2-(3-Fluoro-phenyl)-pyrimidine-5-carboxylic acid 3-(2-hydroxy-1,1-dimethyl-ethylsulfamoyl)-benzylamide,
2-(3-Fluoro-phenyl)-pyrimidine-5-carboxylic acid 3-sulfamoyl-benzylamide,
2-(3-Fluoro-phenyl)-pyrimidine-5-carboxylic acid 3-(2-morpholin-4-yl-ethylsulfamoyl)-benzylamide,
2-(3-Fluoro-phenyl)-pyrimidine-5-carboxylic acid 3-(2-piperidin-1-yl-ethylsulfamoyl)-benzylamide,
2-(3-Fluoro-phenyl)-pyrimidine-5-carboxylic acid 3-[2-(1-methyl-pyrrolidin-2-yl)-ethylsulfamoyl]-benzylamide,
2-(3-Fluoro-phenyl)-pyrimidine-5-carboxylic acid 3-[(1-ethyl-pyrrolidin-2-ylmethyl)-sulfamoyl]-benzylamide,
2-(3-Fluoro-phenyl)-pyrimidine-5-carboxylic acid 3-[2-(1H-imidazol-4-yl)-ethylsulfamoyl]-benzylamide,
2-(3-Fluoro-phenyl)-pyrimidine-5-carboxylic acid 3 43-(2-methyl-piperidin-1-yl)-propylsulfamoyll-benzylamide,
2-(3-Fluoro-phenyl)-pyrimidine-5-carboxylic acid 3-(3-pyrrolidin-1-yl-propylsulfamoyl)-benzylamide,
2-(3-Fluoro-phenyl)-pyrimidine-5-carboxylic acid 3-(2-dimethylamino-ethylsulfamoyl)-benzylamide,
2-(3-Fluoro-phenyl)-pyrimidine-5-carboxylic acid 3-(2-diethylamino-ethylsulfamoyl)-benzylamide,
2-(3-Fluoro-phenyl)-pyrimidine-5-carboxylic acid 3-(3-dimethylamino-2,2-dimethyl-propylsulfamoyl)-benzylamide,
2-(3-Fluoro-phenyl)-pyrimidine-5-carboxylic acid 3-(5-dimethylamino-pentylsulfamoyl)-benzylamide,
2-(3-Fluoro-phenyl)-pyrimidine-5-carboxylic acid 3-(2-diisopropylamino-ethylsulfamoyl)-benzylamide,
2-(3-Fluoro-phenyl)-4-methyl-pyrimidine-5-carboxylic acid 3-(methanesulfonylamino-methyl)-benzylamide,
2-(3-Fluoro-phenyl)-4-methyl-pyrimidine-5-carboxylic acid 3-[(propane-2-sulfonylamino)-methyl]-benzylamide,
2-(3-Fluoro-phenyl)-4-methyl-pyrimidine-5-carboxylic acid 3-methylsulfamoylmethyl-benzylamide,
2-(3-Fluoro-phenyl)-4-methyl-pyrimidine-5-carboxylic acid 3-(isopropylsulfamoyl-methyl)-benzylamide,
2-(3-Fluoro-phenyl)- pyrimidine-5-carboxylic acid 3-(methanesulfonylamino-methyl)-benzylamide,
2-(3-Fluoro-phenyl)- pyrimidine-5-carboxylic acid 3-[(propane-2-sulfonylamino)-methyl]-benzylamide, 2-(3-Fluoro-phenyl)- pyrimidine-5-carboxylic acid 3-methylsulfamoylmethyl-benzylamide,
2-(3-Fluoro-phenyl)- pyrimidine-5-carboxylic acid 3-(isopropylsulfamoyl-methyl)-benzylamide
2-(3-Fluoro-phenyl)-pyrimidine-5-carboxylic acid (2-methanesulfonylamino-pyridin-4-ylmethyl)-amide,
2-(5-Methyl-[1,2,4]oxadiazole-3-yl)-pyrimidine-5-carboxylic acid (tetrahydro-pyran-4-yl)-amide,
2-(5-Methyl-[1,2,4]oxadiazole-3-yl)-pyrimidine-5-carboxylic acid 4 sulfamoyl-benzeneamide,
2-(5-Methyl-[1,2,4]oxadiazol-3-yl)-pyrimidine-5-carboxylic acid (3-phenyl-[1,2,4]thiadiazol-5-y1)-amide,
2-(3-Fluoro-phenyl)-pyrimidine-5-carboxylic acid 3-(morpholine-4-sulfonyl)-benzylamide,
2-Pheny-pyrimidine-5-carboxylic acid 3,4-dimethoxy-benzylamide,
2-Pheny-pyrimidine-5-carboxylic acid (1H-indazol-5-yl)-amide,
2-Phenyl-pyrimidine-5-carboxylic acid 4-[1,2,3]thiadiazol-5-yl)-benzylamide,
2-(3-Fluoro-phenyl)-4-methyl-pyrimidine-5-carboxylic acid 3-methylsulfamoyl-benzylamide,
4-Methyl-2-pyridin-2-yl-pyrimidine-5-carboxylic acid 3-methylsulfamoyl-benzylamide,
2-Pheny-pyrimidine-5-carboxylic acid 4-morpholin-4-yl-benzylamide,
6-[(2-Phenyl-pyrimidin-5-carbonyl)-amino]-1H-benzoimidazole-2-carboxylic acid methyl ester,
6-[(2-Phenyl-pyrimidin-5-carbonyl)-amino]-1H-benzoimidazole-2-carboxylic acid,
2-Pheny-pyrimidine-5-carboxylic acid (benzofuran-5-ylmethyl)-amide,
2-Pheny-pyrimidine-5-carboxylic acid 4-methanesulfonylamino-benzylamide,
2-Pheny-pyrimidine-5-carboxylic acid 4-carbamoyl-benzylamide,
2-Pheny-pyrimidine-5-carboxylic acid 3-(2-hydroxy-ethylsulfamoyl)-benzylamide,
2-Pheny-pyrimidine-5-carboxylic acid 4-(morpholin-4-sulfonyl)-benzylamide,
2-Pheny-pyrimidine-5-carboxylic acid 3-methylsulfamoyl-benzylamide,
2-Phenyl-pyrimidine-5-carboxylic acid [2-(2-amino-4-methyl-thiazol-5-yl)-ethyl]-amide,
2-(3-Fluoro-phenyl)-pyrimidine-5-carboxylic acid 3-methylsulfamoyl-benzylamide,
{4- {[(2-Phenyl-pyrimidine-5-carbonyl)-amino]-benzyl}-phosphonic acid diethyl ester,
{4-[(2-Phenyl-pyrimidine-5-carbonyl)-amino]-butyl)-phosphonic acid diethyl ester,
{4-[(2-Phenyl-pyrimidine-5-carbonyl)-amino]-ethyl)-phosphonic acid diethyl ester,
{Phenyl-[(2-phenyl-pyrimidine-5-carbonyl)-amino]-methyl)-phosphonic acid diethyl ester,
2-(3-Fluoro-phenyl)-pyrimidine-5-carboxylic acid 3-methanesulfonyl)-benzylamide,
2-(3-Fluoro-phenyl)-pyrimidine-5-carboxylic acid (1-methanesulfonyl-piperidin-3-ylmethyl)-amide,
2-(3-Fluoro-phenyl)-pyrimidine-5-carboxylic acid (1-dimethanesulfamoyl-piperidin-3-ylmethyl)-amide,
2-(Phenyl)-pyrimidine-5-carboxylic acid 3-methanesulfonylamino-benzylamide,
2-(3-Fluoro-phenyl)-pyrimidine-5-carboxylic acid 3-acetylsulfamoyl-benzylamide,
2-(3-Fluoro-phenyl)-pyrimidine-5-carboxylic acid 3-(3-oxo-piperiazine-l-sulfonyl)-benzylamide,
2-Pheny-pyrimidine-5-carboxylic acid (2-sulfamoyl-ethyl)-amide,
2-Pheny-pyrimidine-5-carboxylic acid (2-dimethylsulfamoyl-ethyl)-amide,
2-Phenyl-pyrimidine-5-carboxylic acid (3-phenyl-[1,2,4]thiadiazol-5-yl)-amide,
4-Methyl-2-phenyl-pyrimidine-5-carboxylic acid (3-phenyl-[1,2,4]thiadiazol-5-yl)-amide
2-(3-Fluoro-phenyl)-pyrimidine-5-carboxylic acid (3-phenyl-[1,2,4]thiadiazol-5-yl)amide,
2-(3-Fluoro-phenyl)-pyrimidine-5-carboxylic acid (tetrahydro-pyran-4-yl)-amide,
2-Cyclohexyl-pyrimidine-5-carboxylic acid phenylamide,
2-Phenyl-pyrimidine-5-carboxylic acid 3-amino-benzylamide,
2-(3-Pyridyl)-pyrimidine-5-carboxylic acid-3-methylsulfamoyl-benzylamide,
2-Pyrazol-1-yl-pyrimidine-5-carboxylic acid 4-sulfamoyl-benzylamide,
2-(2-Methyl-thiazol-4-yl)-pyrimidine-5-carboxylic acid (tetrahydro-pyran-4-yl)-amide,
2-Phenyl-pyrimidine-5-carboxylic acid (thiophen-2-ylmethyl)-amide,
2-Phenyl-pyrimidine-5-carboxylic acid (4-methyl-oxazol-2-yl)-amide,
Methoxyimino-{2-[(2-phenyl-pyrimidine-5-carbonyl)-amino]-thiazol-4-yl}-acetic acid ethyl ester,
2-Phenyl-pyrimidine-5-carboxylic acid (5-methylsulfanyl-[1,3,4]thiadiazol-2-yl)-amide,
2-[(2-Phenyl-pyrimidine-5-carbonyl)-amino]-benzothiazole-5-carboxylic acid ethyl ester,
(R)-2-Phenyl-pyrimidine-5-carboxylic acid (1-phenyl-ethyl)-amide,
2-Phenyl-pyrimidine-5-carboxylic acid [3-(1H-tetrazol-5-yl)-phenyl]-amide,
2-Phenyl-pyrimidine-5-carboxylic acid (1-carbamimidoyl-piperidin-4-ylmethyl)-amide,
5-[(2-Phenyl-pyrimidine-5-carbonyl)-amino]-1H-indole-3-carboxylic acid amide,
2-Phenyl-pyrimidine-5-carboxylic acid [3-(2-amino-thiazol-4-yl)-phenyl]-amide,
2-Phenyl-pyrimidine-5-carboxylic acid {4-[2-(1,3-dioxo-1,3-dihydro-isoindo1-2-yl)-ethyl]-thiazol-2-yl}-amide,
2-(3-Fluoro-phenyl)-pyrimidine-5-carboxylic acid [2-(pyrrolidine-l-sulfonyl)-ethyl]-amide,
[3 -({ [2-(3-Fluoro-phenyl)-4-methyl-pyrimidine-5-carbonyl]-amino}-methyl)-benzyl]-carbamic acid tert-butyl ester,
2-(3-Fluoro-phenyl)-pyrimidine-5-carboxylic acid 3-[(pyridin-2-ylmethyl)-sulfamoyl]-benzylamide,
2-(3-Fluoro-phenyl)-pyrimidine-5-carboxylic acid 3-(3-hydroxy-2,2-dimethyl-propylsulfamoyl)-benzylamide,
2-(3-Fluoro-phenyl)-pyrimidine-5-carboxylic acid 3-(2-hydroxy-2-methyl-propylsulfamoyl)-benzylamide,
2-(3-Fluoro-phenyl)-pyrimidine-5-carboxylic acid 3-[(tetrahydro-pyran-4-ylmethyl)-sulfamoyl]-benzylamide,
2-(3-Fluoro-phenyl)-pyrimidine-5-carboxylic acid 3-(4-hydroxy-butylsulfamoyl)-benzylamide,
2-(3-Fluoro-phenyl)-pyrimidine-5-carboxylic acid 342-(2-hydroxy-ethoxy)-ethylsulfamoyll-benzylamide,
2-(3-Fluoro-phenyl)-pyrimidine-5-carboxylic acid 3-[(tetrahydro-furan-2-ylmethyl)-sulfamoyl]-benzylamide,
2-(3-Fluoro-phenyl)-pyrimidine-5-carboxylic acid 3-isobutylsulfamoyl-benzylamide,
2-(3-Fluoro-phenyl)-pyrimidine-5-carboxylic acid (5-isopropylsulfamoyl-pyridin-3-ylmethyl)-amide, 2-(3-Fluoro-phenyl)-pyrimidine-5-carboxylic acid (5-methylsulfamoyl-pyridin-3-ylmethyl)-amide, 2-(3-Fluoro-phenyl)-pyrimidine-5-carboxylic acid (2-methylsulfamoyl-pyridin-4-ylmethyl)-amide, 2-(3-Fluoro-phenyl)-4-methyl-pyrimidine-5-carboxylic acid (2-methylsulfamoyl-pyridin-4-ylmethyl)-amide, or 2-(3-Fluoro-phenyl)-4-methyl-pyrimidine-5-carboxylic acid (5-isopropylsulfamoyl-pyridin-3-ylmethyl)-amide, or N-oxide thereof, or a pharmaceutically acceptable salt thereof.

25. A pharmaceutical composition comprising the compound according to claim 1, or N-oxide thereof, or a pharmaceutically acceptable salt thereof, and a pharmaceutically acceptable carrier.

26. A pharmaceutical composition comprising the compound according to claim 24, or N-oxide thereof, or a pharmaceutically acceptable salt thereof, and a pharmaceutically acceptable carrier.

27. A method for treating allergic rhinitis, asthma or chronic obstructive pulmonary disease, in a patient in need thereof, comprising administering to the patient a pharmaceutically effective amount of the compound according to claim 1, or N-oxide thereof, or a pharmaceutically acceptable salt thereof.

28. A method for treating allergic rhinitis, asthma or chronic obstructive pulmonary disease, in a patient in need thereof, comprising administering to the patient a pharmaceutically effective amount of the compound according to claim 24, or N-oxide thereof, or a pharmaceutically acceptable salt thereof.

* * * * *